United States Patent
Ries et al.

(10) Patent No.: US 9,095,453 B2
(45) Date of Patent: Aug. 4, 2015

(54) POSITION ADJUSTABLE TRIAL SYSTEMS FOR PROSTHETIC IMPLANTS

(75) Inventors: Michael D. Ries, Tiburon, CA (US); Mark J Mooradian, Phoenix, AZ (US)

(73) Assignee: Michael D. Ries, Reno, NV (US)

( * ) Notice: Subject to any disclaimer, the term of this patent is extended or adjusted under 35 U.S.C. 154(b) by 141 days.

(21) Appl. No.: 12/949,103

(22) Filed: Nov. 18, 2010

(65) Prior Publication Data

US 2011/0066248 A1    Mar. 17, 2011

Related U.S. Application Data

(63) Continuation-in-part of application No. 12/606,326, filed on Oct. 27, 2009, now Pat. No. 8,906,105.

(60) Provisional application No. 61/233,081, filed on Aug. 11, 2009, provisional application No. 61/262,780, filed on Nov. 19, 2009, provisional application No. 61/301,877, filed on Feb. 5, 2010, provisional application No. 61/360,733, filed on Jul. 1, 2010.

(51) Int. Cl.
*A61B 17/58* (2006.01)
*A61B 17/60* (2006.01)
(Continued)

(52) U.S. Cl.
CPC ........... *A61F 2/4684* (2013.01); *A61B 17/1764* (2013.01); *A61F 2/385* (2013.01);
(Continued)

(58) Field of Classification Search
CPC ................ A61F 2/4684; A61F 2/3868; A61F 2002/30878; A61B 17/1764
USPC ........... 606/86 R, 87–90, 99, 102; 623/20.14, 623/20.15, 20.32–20.34
See application file for complete search history.

(56) References Cited

U.S. PATENT DOCUMENTS

| 1,372,918 A | 3/1921 | Udgaard |
| 4,211,228 A | 7/1980 | Cloutier |

(Continued)

FOREIGN PATENT DOCUMENTS

| DE | 202010000037 | 3/2010 |
| EP | 1378216 | 1/2004 |

(Continued)

OTHER PUBLICATIONS

Walker; Peter s.: *Biomechanical Principles of Total Knee Replacement Design.* Basic Orthpaedic Biomechanics $2^{nd}$ edition, pp. 1-493, 1997.

(Continued)

*Primary Examiner* — Matthew Lawson
*Assistant Examiner* — Si Ming Lee
(74) *Attorney, Agent, or Firm* — Snell & Wilmer L.L.P.

(57) ABSTRACT

A trial system for an implantable joint replacement includes a guide assembly having a baseplate and a guide plate, the guide plate rotatable relative to the base plate about a rotation axis extending through the guide plate and the baseplate while directly connected to the baseplate. An adjustment mechanism is actuable to selectively control the rotational juxtaposition of the guide plate relative to the baseplate. The rotation axis may be medially offset from the center of the guide assembly. A single instrument may be used to rotate the guide plate relative to the base plate and lock the plates in the selected juxtaposition. The guide plate provides in situ positionable cutting guidance for implantation of prosthetic joint components. The system may further include an articulating insert trial mounted on the guide assembly to determine preferred joint alignment and/or optimal positioning of the guide plate.

9 Claims, 50 Drawing Sheets

(51) Int. Cl.
*A61F 2/00* (2006.01)
*A61F 2/46* (2006.01)
*A61B 17/17* (2006.01)
*A61F 2/38* (2006.01)
*A61F 2/30* (2006.01)

(52) U.S. Cl.
CPC ............ *A61F 2/3868* (2013.01); *A61F 2/3886* (2013.01); *A61F 2002/30616* (2013.01); *A61F 2002/30878* (2013.01); *A61F 2002/30884* (2013.01)

(56) References Cited

U.S. PATENT DOCUMENTS

| | | |
|---|---|---|
| 4,213,209 A | 7/1980 | Insall |
| 4,224,697 A | 9/1980 | Murray |
| 4,634,444 A | 1/1987 | Noiles |
| 4,714,472 A | 12/1987 | Khowaylo |
| 4,936,853 A | 6/1990 | Fabian et al. |
| 5,047,058 A | 9/1991 | Roberts |
| 5,071,438 A | 12/1991 | Jones |
| 5,071,738 A | 12/1991 | Mizukura |
| 5,330,533 A | 7/1994 | Walker |
| 5,330,534 A | 7/1994 | Herrington |
| 5,370,701 A | 12/1994 | Finn |
| 5,387,240 A | 2/1995 | Pottenger |
| 5,413,604 A | 5/1995 | Hodge |
| 5,480,446 A | 1/1996 | Goodfellow |
| 5,658,342 A | 8/1997 | Draganich |
| 5,702,464 A * | 12/1997 | Lackey et al. ............. 623/20.32 |
| 5,755,801 A | 5/1998 | Walker |
| 5,755,804 A | 5/1998 | Schmotzer et al. |
| 5,824,102 A | 10/1998 | Buscayret |
| 5,879,392 A | 3/1999 | McMinn |
| 5,879,394 A | 3/1999 | Ashby |
| 5,906,643 A | 5/1999 | Walker |
| 5,928,286 A | 7/1999 | Ashby |
| 5,976,147 A * | 11/1999 | LaSalle et al. ................. 606/88 |
| 6,013,103 A | 1/2000 | Kaufman |
| 6,039,764 A | 3/2000 | Pottenger |
| 6,080,195 A | 6/2000 | Colleran |
| 6,099,570 A | 8/2000 | Livet et al. |
| 6,159,216 A | 12/2000 | Burkinshaw et al. |
| 6,165,223 A | 12/2000 | Cox |
| 6,203,576 B1 | 3/2001 | Afriat |
| 6,214,052 B1 | 4/2001 | Burkinshaw |
| 6,296,666 B1 | 10/2001 | Gardner |
| 6,387,111 B1 | 5/2002 | Barber |
| 6,413,279 B1 | 7/2002 | Cox |
| 6,428,577 B1 * | 8/2002 | Evans et al. ................ 623/20.29 |
| 6,558,427 B2 | 5/2003 | Leclercq |
| 6,592,588 B1 | 7/2003 | Bobic |
| 6,620,168 B1 * | 9/2003 | Lombardo et al. ............. 606/88 |
| 6,629,999 B1 | 10/2003 | Serafin, Jr. |
| 6,645,215 B1 * | 11/2003 | McGovern et al. ........... 606/102 |
| 6,764,516 B2 | 7/2004 | Pappas |
| 6,773,461 B2 | 8/2004 | Meyers et al. |
| 6,797,005 B2 | 9/2004 | Pappas |
| 6,972,039 B2 | 12/2005 | Metzger |
| 6,974,481 B1 | 12/2005 | Carson |
| 6,986,791 B1 | 1/2006 | Metzger |
| 7,001,394 B2 | 2/2006 | Gundlapalli |
| 7,105,027 B2 | 9/2006 | Lipman |
| 7,232,465 B2 | 6/2007 | Keller |
| 7,328,634 B1 | 2/2008 | Greenberg et al. |
| 7,422,605 B2 | 9/2008 | Angibaud |
| 7,572,292 B2 | 8/2009 | Crabtree |
| 7,658,767 B2 | 2/2010 | Wyss |
| 7,691,150 B2 * | 4/2010 | Cronin et al. ............. 623/20.32 |
| 8,137,407 B2 | 3/2012 | Todd et al. |
| 2001/0003803 A1 | 6/2001 | Leclercq |
| 2003/0009229 A1 | 1/2003 | Pappas |
| 2003/0009232 A1 | 1/2003 | Hoeppner |
| 2003/0153980 A1 | 8/2003 | Brack |
| 2003/0199985 A1 | 10/2003 | Masini |
| 2004/0097951 A1 * | 5/2004 | Steffensmeier ............... 606/102 |
| 2004/0243244 A1 | 12/2004 | Ries |
| 2005/0021039 A1 | 1/2005 | Cusick et al. |
| 2005/0149045 A1 | 7/2005 | Elliott |
| 2005/0203528 A1 | 9/2005 | Couture et al. |
| 2005/0209701 A1 | 9/2005 | Kuramoto |
| 2005/0209702 A1 | 9/2005 | Todd |
| 2006/0064104 A1 * | 3/2006 | Kana et al. ...................... 606/86 |
| 2006/0149276 A1 * | 7/2006 | Grimm .......................... 606/88 |
| 2006/0161259 A1 | 7/2006 | Huang |
| 2006/0184176 A1 * | 8/2006 | Straszheim-Morley et al. .............................. 606/88 |
| 2006/0190086 A1 | 8/2006 | Clemow |
| 2007/0100462 A1 | 5/2007 | Lang |
| 2007/0100463 A1 | 5/2007 | Aram |
| 2007/0129808 A1 | 6/2007 | Justin et al. |
| 2007/0135925 A1 | 6/2007 | Walker |
| 2007/0135926 A1 | 6/2007 | Walker |
| 2007/0173848 A1 | 7/2007 | Lennox et al. |
| 2007/0173856 A1 | 7/2007 | Parker |
| 2008/0009950 A1 | 1/2008 | Richardson |
| 2008/0021566 A1 | 1/2008 | Peters |
| 2008/0027555 A1 | 1/2008 | Hawkins |
| 2008/0097616 A1 | 4/2008 | Meyers et al. |
| 2008/0114464 A1 | 5/2008 | Barnett |
| 2008/0119940 A1 | 5/2008 | Otto |
| 2008/0188943 A1 | 8/2008 | Smith |
| 2008/0195109 A1 * | 8/2008 | Hunter et al. ................... 606/87 |
| 2008/0243259 A1 | 10/2008 | Lee |
| 2008/0300690 A1 | 12/2008 | Burstein |
| 2009/0043395 A1 | 2/2009 | Takano |
| 2009/0043396 A1 | 2/2009 | Komistek |
| 2009/0088861 A1 | 4/2009 | Tuke |
| 2009/0090220 A1 | 4/2009 | Kimberly |
| 2009/0149964 A1 | 6/2009 | May |
| 2009/0210066 A1 | 8/2009 | Jasty |
| 2009/0299482 A1 | 12/2009 | Metzger et al. |
| 2009/0326665 A1 | 12/2009 | Gomaa |
| 2009/0326666 A1 | 12/2009 | Bennett |
| 2009/0326668 A1 | 12/2009 | Dun |
| 2010/0010635 A1 | 1/2010 | Straszheim-Morley et al. |
| 2010/0016978 A1 | 1/2010 | Gomaa |
| 2010/0016979 A1 | 1/2010 | Gomaa |
| 2010/0042224 A1 | 2/2010 | Garino |
| 2010/0049200 A1 * | 2/2010 | Re ................................. 606/89 |
| 2010/0312351 A1 | 12/2010 | Belcher |

FOREIGN PATENT DOCUMENTS

| | | |
|---|---|---|
| JP | 2008062030 | 3/2008 |
| WO | WO9525484 | 9/1995 |
| WO | WO9603097 | 2/1996 |
| WO | WO9613233 | 5/1996 |
| WO | WO9846171 | 10/1998 |
| WO | WO0113825 | 3/2001 |
| WO | 0182842 | 11/2001 |
| WO | WO0234156 | 5/2002 |
| WO | 03059203 | 7/2003 |
| WO | WO2006118822 A2 | 11/2006 |
| WO | WO2008045863 | 4/2008 |
| WO | 2011059759 | 5/2011 |

OTHER PUBLICATIONS

Dennis; Douglas A., et al. *A Multicenter Analysis of Axial Femorotibial Rotation after Total Knee Arthroplasty.* Clinical Orthopaedics and Related Research No. 428, pp. 180-189 (2004).

Dennis; Douglas A. et al: *Factors Affecting Flexion After Total Knee Arthroplasty.* Clinical Orthopedics and Related Research, No. 464, pp. 53-60 (2007.

Argenson; Jean-Noel A.: *In Vivo Kinematic Evaluation and Design Considerations Related to High Flexion in Total Knee Arthroplasty.* Journal of Biomechanics 38 (2005) pp. 277-284.

Halloran; Jason P. et al.: *Explicit Finite Element Modeling of Total Knee Replacement Mechanics.* Journal of Biomechanics 38 (2005) pp. 323-331.

(56) References Cited

OTHER PUBLICATIONS

Morra; Edward A., et al.: *The Influence of Contemporary Knee Design on High Flexion II: A Kinematic Comparison with the Normal Knee.* Orthopaedic Research Laboratories Cleveland, Ohio, (2009).
Greenwald; Seth A., et al.: *Mobile-Bearing Knee Systems: Ultra-High Molecular Weight Polyethylene Wear and Design Issues.* AAOS Instructional Course Lectures, vol. 54 (2005) pp. 195-205.
Vertullo; Christopher J., et al.: *Mobile Bearing in Primary Knee Arthroplasty.* Journal of the American Academy of Orthopaedic Surgeons, vol. 9, No. 6, Nov./Dec. 2001 pp. 355-364.
Morra, Edward A., et al.: *Polymer Insert Stress in Total Knee Designs During High Flexion Activities.* A Finite Element Study, Orthopaedic Research Laboratories (2005) AAOS.
Catani, Fabio, et al.: *In Vivo Kinematics of Guided Motion Total Knee Arthroplasty.* Smith & Nephew, Poster # 1987 at the 2008 ORS Annual Meeting, San Francisco, CA.
Smith & Nephew: *Bi-Cruciate Stabilized Knee System* Journey Knee (2006) www.journeyknee.com.
Biomet AGC Total Knee System: Product Brochure May 2009 http://www.biomet.com.
Biomet Europe: *ALPINA APR Total Knee Prosthesis* (2007) http://www.biomet.co.uk/index.php?id=17313.
Biomet Europe: *Oxford TML* (2007) http://www.biomet.co.uk/index.php?id=185&PHPSESSID=3b5253f8b4.
Biomet Europe: *Vanguard Complete Knee System.* Product Brochure (May 2009) http://www.biomet.co.uk.
Consensus Orthopedics: *Mobile Bearing Knee.* Product Brochure (2009) www.consensusortho.com.
Corin Group: Total Knee Replacement. Product Brochure (Jan. 20, 2011) http://www.coringroup.com/medical_professionals/products/knees/.
Depuy Orthopaedics Inc: *Finsbury; Dual Bearing Knee (DBK)* (2010) (http://www.finsbury.org/printer_friendly_version.asp?contentID=50.
DePuy: *LCS Complete Knee Systems.* (2011) pp. 1-2 http://www.depuy.com/healthcare-professionals/product-details/lcs-complete-knee-system.
Depuy Orthopaedics Inc: *Sigma Rotating Platform Knee System.* © 2008-2009 DePuy Orthopaedics, Inc. Product Brochure. (May 2009) http://www.depuy.com/healthcare-professionals/product-details.
Akagi; Masao: *A Mechanical Comparison of 2 Posterior-Stabilizing Designs; Insall/Burstein 2 Knee and Bisurface Knee.* The Journal of Arthroplasty vol. 17 No. 5 pp. 627-634 (2002).
Smith & Nephew: Journey Bi-Cruciate Stabilized Knee System. Product Brochure May 2009.
Sonstegard; DA: *The Spherocentric Knee: Biomechanical Testing and Clinical Trial.* The Journal of Bone & Joint Surgery (1977) vol. 59 pp. 602-616 Website: www.jbjs.org.
Stryker Orthopaedics: *Scorpio NRG (The Evolution of a High Performance Knee System)* Product Brochure (2007) Website: www.stryker.com.
Wright Medical: *Advance Knee System.* Family Product Brochure (2006) Website: www.wmt.com.
Zimmer: *Comprehensive Natural-Knee Family.* (2006) Website: http://www.zimmer.co.uk/z/ctl/op/global/action/1/id/7802/template/MP.
Zimmer: *Gender Solutions Natural-Knee Flex System.* Product Brochure (2007) Website: www.zimmer.com.
Zimmer: The Comprehensive Natural-Knee Family (2007) Website: http://www.zimmer.co.uk/z/ctl/op/global/action/1/id/7802/template/MP.
Zimmer: *NexGen Complete Knee Solutions.* Product Brochure: #97-5972-205 (2000-2001).
Zimmer: *NexGen LPS-Flex Mobile and LPS-Mobile Bearing Knee.* Advertisement (2008) #97-5964-017-00.
Office Action dated Jul. 11, 2014 in U.S. Appl. No. 12/606,326.
Office Action dated Aug. 25, 2014 in U.S. Appl. No. 12/914,799.
Notice of Allowance dated Oct. 27, 2014 in U.S. Appl. No. 12/606,326.
Exam Report dated Dec. 3, 2014 in European Application No. 11738916.3.
Notice of Allowance dated Jan. 21, 2015 in U.S. Appl. No. 12/914,799.
Intention to Grant dated Apr. 14, 2015 in European Application No. 11738916.3.
Restriction Requirement dated Nov. 26, 2012 in U.S. Appl. No. 12/949,073.
Office Action dated Jan. 23, 2013 in U.S. Appl. No. 12/949,073.
Notice of Allowance dated Jun. 26, 2013 in U.S. Appl. No. 12/949,073.
Restriction Requirement dated Sep. 20, 2012 in U.S. Appl. No. 12/951,832.
Office Action dated Oct. 26, 2012 in U.S. Appl. No. 12/951,832.
Notice of Allowance dated Apr. 12, 2013 in U.S. Appl. No. 12/951,832.
Restriction Requirement dated Jul. 1, 2011 in U.S. Appl. No. 12/606,326.
Office Action dated Aug. 19, 2011 in U.S. Appl. No. 12/606,326.
Office Action dated Mar. 2, 2012 in U.S. Appl. No. 12/914,799.
Final Office Action dated Aug. 15, 2012 in U.S. Appl. No. 12/914,799.
Final Office Action dated Jan. 27, 2012 in U.S. Appl. No. 12/606,326.
Restriction Requirement dated Apr. 9, 2012 in U.S. Appl. No. 12/949,153.
Office Action dated May 22, 2012 in U.S. Appl. No. 12/949,153.
Notice of Allowance dated Oct. 22, 2012 in U.S. Appl. No. 12/949,153.
Corrected Notice of Allowance dated Nov. 20, 2012 in U.S. Appl. No. 12/949,153.
Restriction Requirement dated Sep. 19, 2012 in U.S. Appl. No. 13/188,699.
Office Action dated Oct. 25, 2012 in U.S. Appl. No. 13/188,699.
Final Office Action dated Apr. 18, 2013 in U.S. Appl. No. 13/188,699.
Notice of Allowance dated Oct. 29, 2013 in U.S. Appl. No. 13/188,699.
International Search Report dated Oct. 21, 2011 in Application No. PCT/US2011/045019.
Written Opinion dated Oct. 21, 2011 in Application No. PCT/US2011/045019.
International Preliminary Report on Patentability dated Oct. 21, 2011 in Application No. PCT/US2011/045019.
International Search Report dated Feb. 14, 2011 in Application No. PCT/US2012/036289.
Written Opinion dated Feb. 14, 2011 in Application No. PCT/US2012/036289.
International Preliminary Report on Patentability dated Feb. 14, 2012 in Application No. PCT/US2012/036289.
International Search Report dated Aug. 2, 2011 in Application No. PCT/US2010/054534.
Written Opinion dated Aug. 2, 2011 in Application No. PCT/US2010/054534.
International Preliminary Report on Patentability dated May 1, 2012 in Application No. PCT/US2010/054534.
International Search Report dated Aug. 18, 2011 in Application No. PCT/US2010/057231.
Written Opinion dated Aug. 18, 2011 in Application No. PCT/US2010/057231.
International Preliminary Report on Patentability dated May 22, 2012 in Application No. PCT/US2010/057231.
International Search Report dated Aug. 22, 2011 in Application No. PCT/US2010/057642.
Written Opinion dated Aug. 22, 2011 in Application No. PCT/US2010/057642.
International Preliminary Report on Patentability dated May 30, 2012 in Application No. PCT/US2010/057642.
Orthopedics, Feature Article; Sep. (2006) vol. 29, No. 9 Supplement, pp. S17-S22.

* cited by examiner

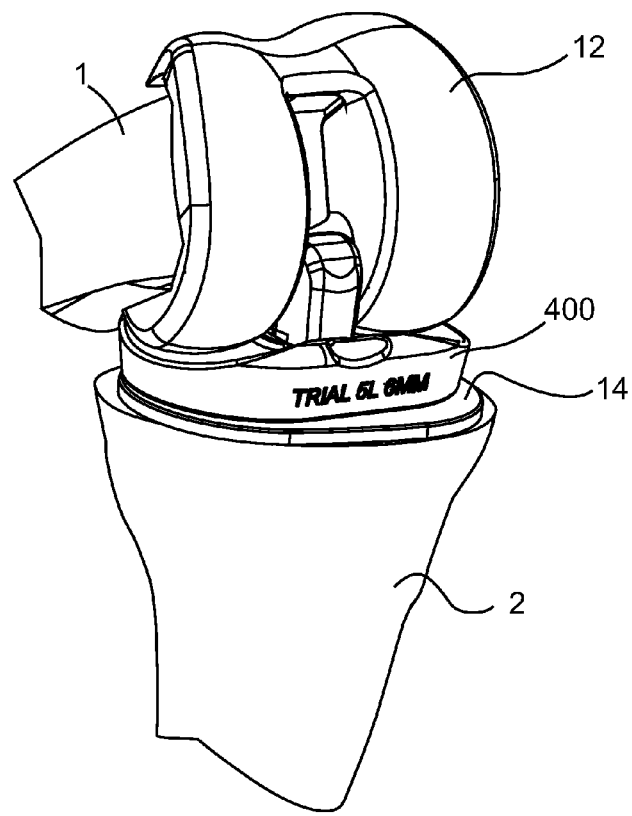
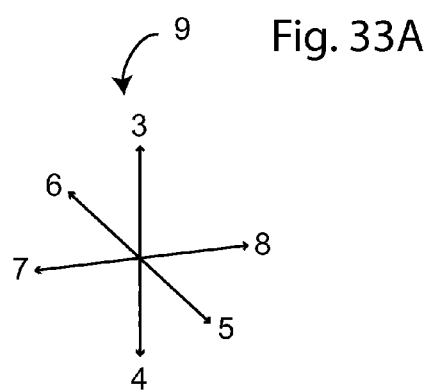
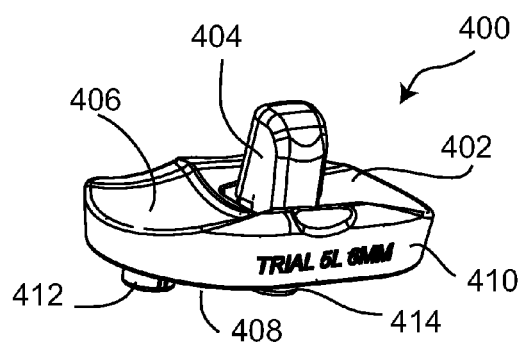
Fig. 33A
Fig. 33B

POSITION ADJUSTABLE TRIAL SYSTEMS FOR PROSTHETIC IMPLANTS

CROSS-REFERENCE TO RELATED APPLICATIONS

This application is a continuation-in-part of:

pending prior U.S. patent application Ser. No. 12/606,326 filed 27 Oct. 2009, and is entitled SYSTEMS AND METHODS FOR MOBILE BEARING PROSTHETIC KNEE, which claims the benefit of:

prior U.S. Provisional Patent Application No. 61/233,081 filed 11 Aug. 2009, and is entitled MOBILE BEARING PROSTHETIC KNEE.

This application also claims the benefit of:

prior U.S. Provisional Patent Application No. 61/262,780 filed 19 Nov. 2009, and is entitled ARTICULATING TRIAL FOR PROSTHETIC IMPLANTS;

prior U.S. Provisional Patent Application No. 61/301,877 filed 5 Feb. 2010, and is entitled ARTICULATING TRIAL FOR PROSTHETIC IMPLANTS; and prior U.S. Provisional Patent Application No. 61/360,733 filed 1 Jul. 2010, and is entitled POSITION ADJUSTABLE ARTICULATING TRIAL FOR PROSTHETIC IMPLANTS.

The above-identified documents are hereby incorporated herein by reference.

BACKGROUND

1. Technical Field

The present disclosure relates to trials for prosthetic implants, and more particularly, to providing articulating trials which are adjustable in situ to allow selection and positioning of a prosthetic joint which provides functionally correct motion similar to kinematic motion of a normal, non-prosthetic joint.

2. The Relevant Technology

One attribute of normal knee flexion is that, as the knee flexes, the contact points of the femur on the tibia move posteriorly. This posterior movement of the contact points is known as rollback. Also, normal knee rollback is much more pronounced on the lateral side of the knee than the medial side, which results in femoral external rotation during knee flexion.

Other prosthetic knees currently on the market do not use two separate fully guided motion paths, and as a consequence may not reproduce normal knee kinematics and need to use wear components made of polyethylene, or similar material, to accommodate the less-guided sliding that occurs during knee flexion. These existing methods and procedures may not be as effective as desired. There is a need to have a tibial insert of a prosthetic knee roll back on a medial pivot axis causing greater rollback on the lateral side than the medial side, like a normal, non-prosthetic knee.

Trials are used during an implantation procedure to simulate the prosthetic device to be implanted, allowing for selection of a proper prosthetic. In joint replacement procedures, there is a need for an articulating trial which simulates the articulation of the natural joint to allow more accurate selection of a properly sized and configured prosthetic. There is also a need for a guiding assembly that is adjustable in situ to precisely position the articulating trial and provide guidance for placement of the prosthetic device.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 33A is a perspective view of a knee joint in a flexed position, with a trial system positioned between a femoral component and a tibial component; FIG. 33B is a perspective view of the trial system, including a tibial insert trial and a cam post trial;

DETAILED DESCRIPTION OF THE PREFERRED EMBODIMENTS

The present invention relates to systems and methods used in orthopaedic surgery, and in particular, to total knee arthroplasty. Those of skill in the art will recognize that the systems and methods described herein may be readily adapted for any total joint arthroplasty procedure. Those of skill in the art will also recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Figure 1:
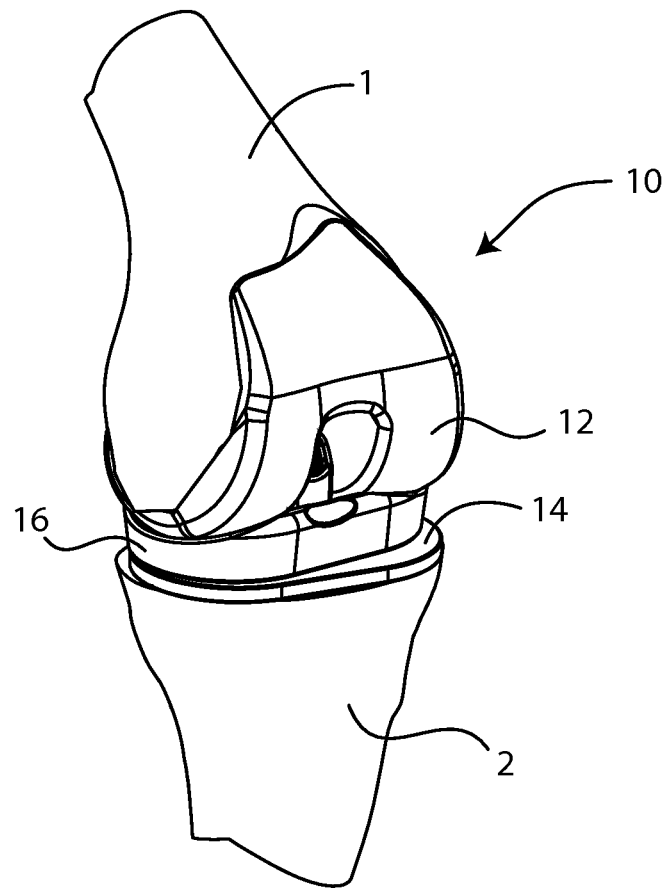
FIG. 1 illustrates a perspective view of the prosthesis, with a femur, a tibia, a tibial baseplate, a tibial insert, a femoral implant and a reference arrow diagram.
Figure 1:
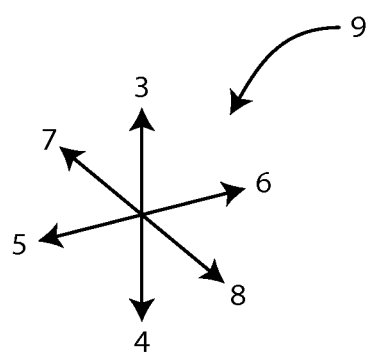

Referring to FIG. 1, a perspective view illustrates a mobile bearing knee prosthesis 10 according to one embodiment of the invention, implanted in a knee. This figure and subsequent figures may be oriented according to the reference arrow diagram 9, having a superior direction 3, an inferior direction 4, a medial direction 5, a lateral direction 6, a posterior direction 7, and an anterior direction 8. In this application, "left" and "right" are used with reference to a posterior view. "Medial" refers to a position or orientation toward a sagittal plane (i.e., plane of symmetry that separates left and right sides of the body from each other), and "lateral" refers to a position or orientation relatively further from the sagittal plane. The knee prosthesis 10 may comprise a tibial baseplate 14, a tibial insert 16 and femoral implant 12.

Figure 2:
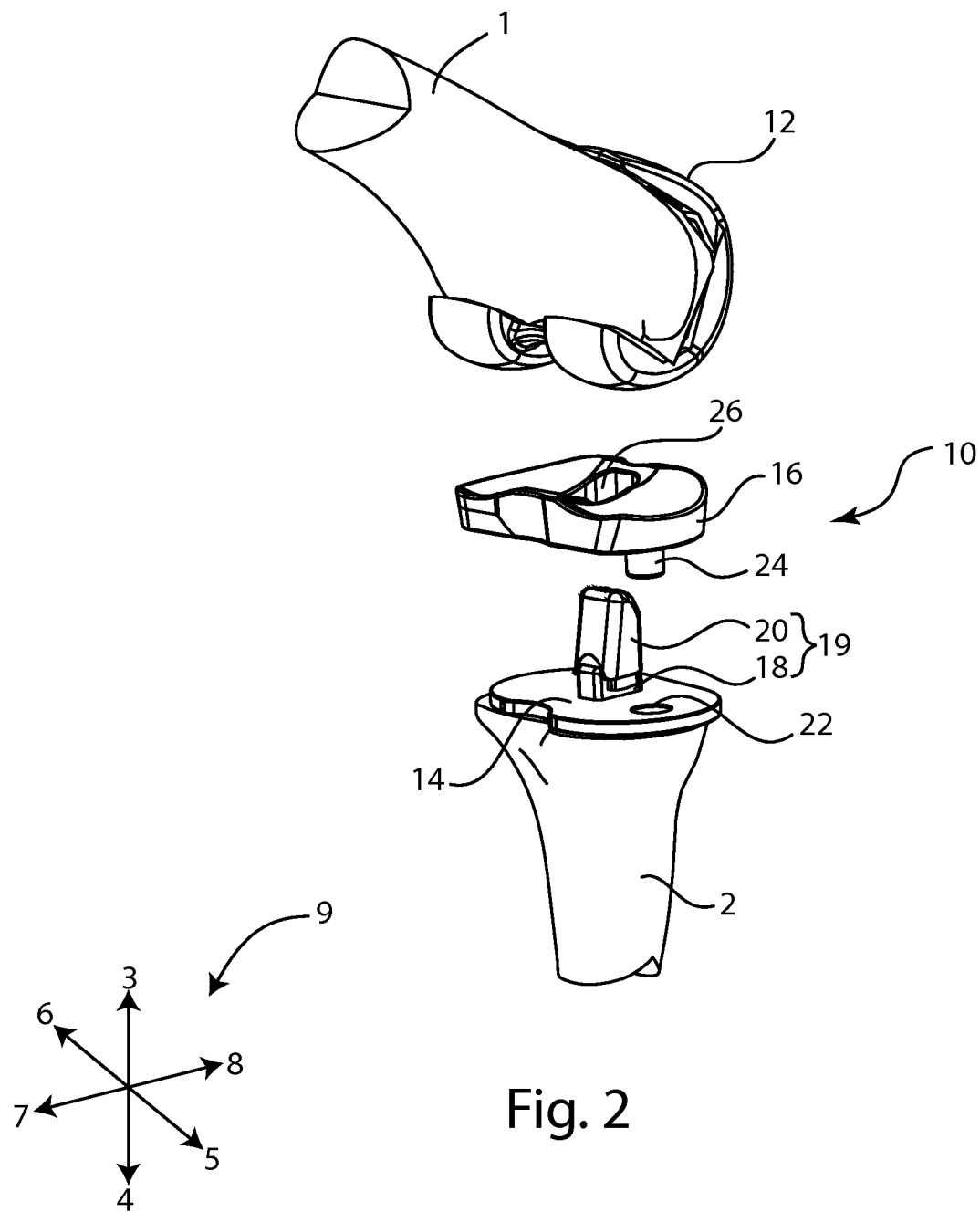
FIG. 2 illustrates an exploded perspective view of the prosthesis of FIG. 1 with the femur, the tibia, the tibial baseplate with a tibial baseplate aperture, the tibial insert with a tibial insert boss and a tibial insert hole, the femoral implant, and a cam post with an outer sleeve.
Figure 3:
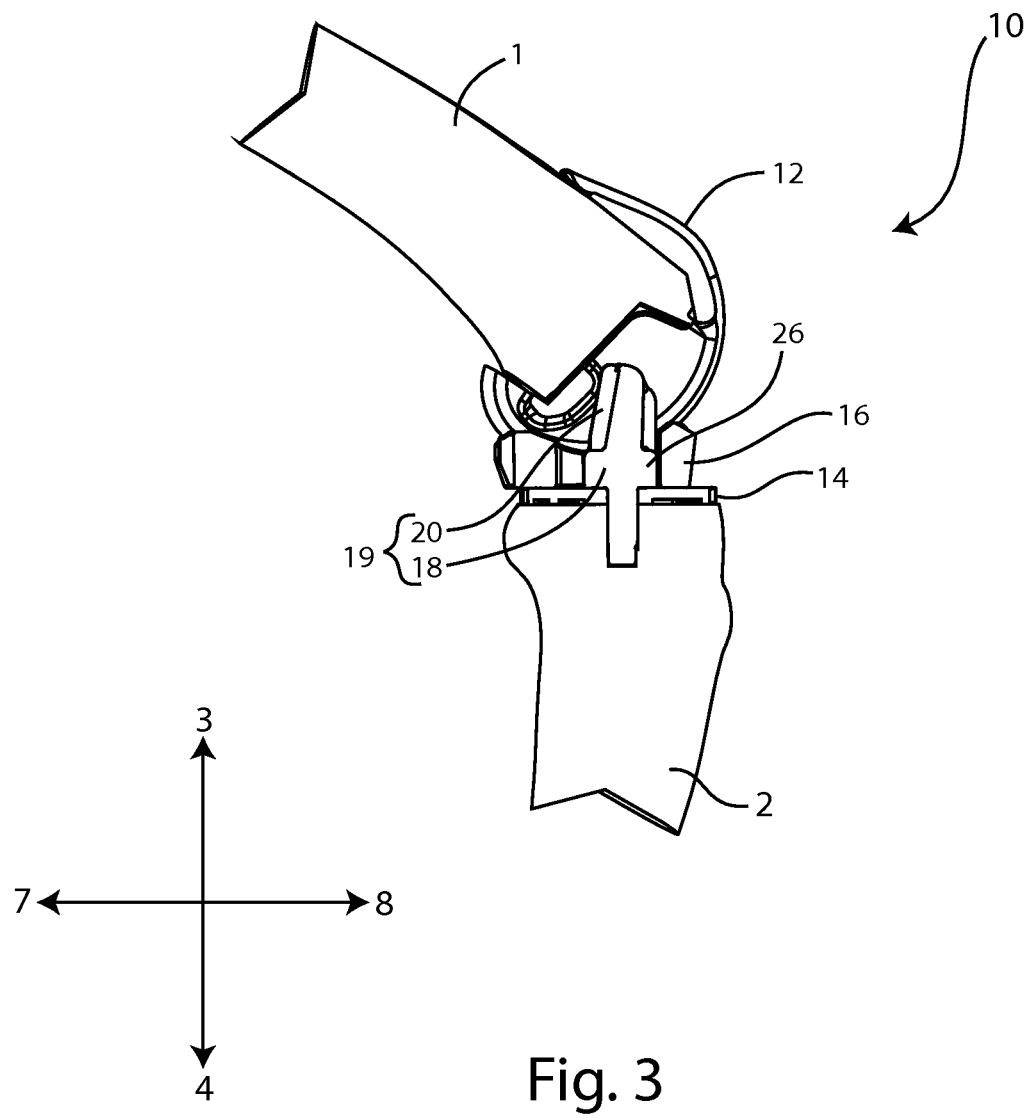
FIG. 3 illustrates a cross sectional side view of the prosthesis of FIG. 1 with the femur, tibia, tibial implant, tibial insert, femoral implant, and the cam post with the outer sleeve.

Referring to FIGS. 2 and 3, the prosthetic knee 10 comprises the tibial baseplate 14, attached to the resected tibia 2, a cam post 19 may be attached to the tibial baseplate 14 and may either be a modular or non-modular part of the baseplate. The cam post 19 helps guide the rotation of the femoral component and tibial insert 16 during flexion of the prosthetic knee 10. The cam post 19 of this embodiment is of two-piece construction, with a metallic cam post core 18 and a polymer outer wear sleeve 20. However, either the cam post core 18 or the sleeve 20 may be comprised of other biocompatible materials. A tibial insert 16 may be rotationally connected to the tibial baseplate 14, rotating about an axis within a tibial insert channel 26 which axis of rotation is medial to the midline of the tibia. A femoral implant 12 may be attached to a resected femur 1, which is supported by the tibial insert 16 and which slidably engages with the cam post 19 to guide the rotation of the tibial insert and posterior movement of the femoral component 16 during flexion of the prosthetic knee 10.

For any of the parts of the prosthetic knee any biocompatible material may be used, including but not limited to stainless steels, titanium and its alloys, cobalt-chrome and its alloys, ceramics, composite materials, and polymers.

Figure 4:
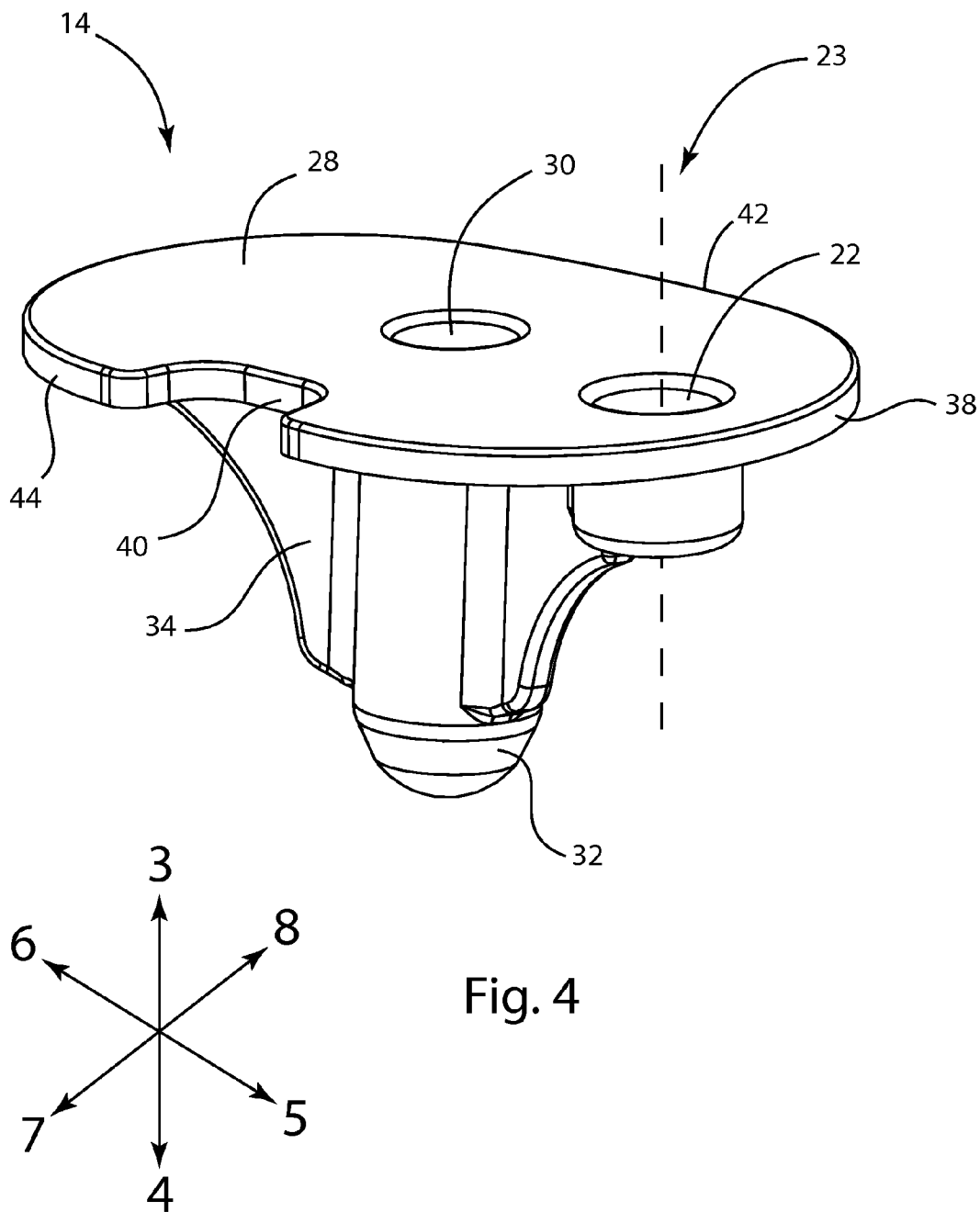
FIG. 4 illustrates a perspective top view of one embodiment of the tibial baseplate of FIG. 1 with the tibial baseplate cavity for retention of a boss of the tibial insert, and a tibial baseplate hole for passage of the cam post, on a tibial baseplate bearing surface, a keel extending into the tibia and at least one wing.
Figure 5:
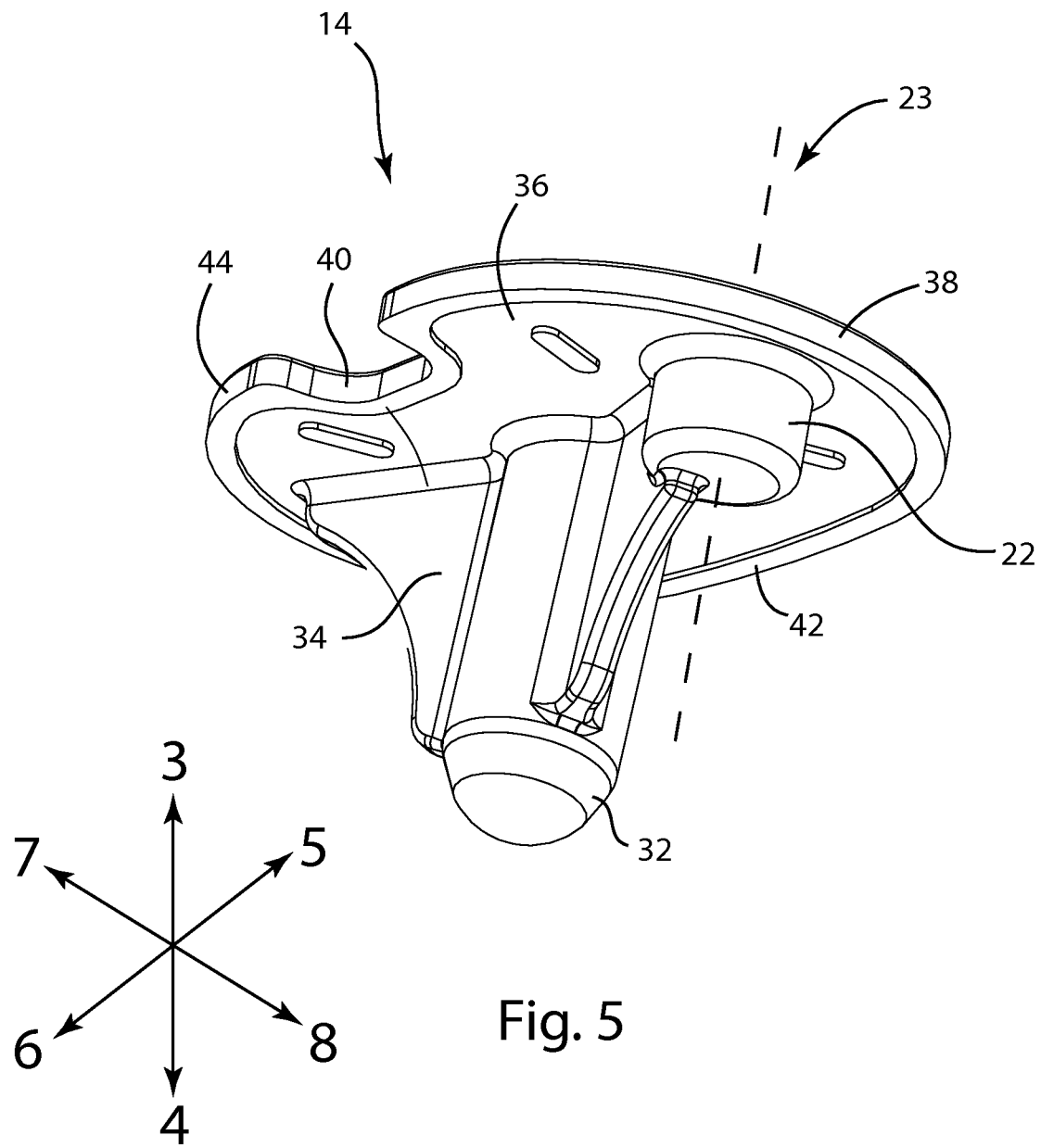
FIG. 5 illustrates a perspective bottom view of the tibial baseplate of FIG. 4 with the at least one wing, the keel, the tibial baseplate aperture and the tibial baseplate cam post aperture.

Referring to FIGS. 4 and 5, the tibial baseplate 14 may be made of a cobalt-chromium alloy. Other metals, such as titanium alloys or other composites may be used as well as polymer, ceramic, or other composite materials. In this embodiment the tibial baseplate 14 is rigidly attached to the resected tibia 2 on a tibia facing surface 36. Protruding inferiorly from the tibia facing surface is a keel 32 and at least one baseplate wing 34. The keel 32 may be driven into the core of the resected tibia 2. The at least one baseplate wing 34 extending from the tibia facing surface the length of the keel 32 and in communication with the keel may also be driven into the resected tibia 2 for added fixation and stabilization. Attachment of the tibial baseplate 14 may also be made by using cement, force fit, bone in-growth, bone screws or other method known in the art. A superior surface 28 of the tibial baseplate 14 may be substantially flat and acts as a support for the tibial insert 16. The superior surface 28 of the tibial baseplate 14 may be polished to minimize wear between the tibial baseplate 14 and the tibial insert 16. The tibial baseplate 14 includes a hole 30, for the mounting of cam post 19, which may be positioned substantially in the geometric center of the tibial baseplate 14 and is deep enough to receive at least a portion of the cam post 19. The tibial baseplate may also include a cavity 22 apart from the hole 30 and positioned substantially medial from the geometric center and apart from a periphery 38 of the tibial baseplate 14. The cavity 22 may provide a rotational medial axis 23 for the tibial insert 16 allowing for rotational movement of the tibial insert about that medial axis. In this embodiment, along a posterior side 44, opposite an anterior side 42, of the periphery 38 of the tibial baseplate 14 comprises a tibial baseplate notch 40 which may allow room for retention of the posterior cruciate ligament (PCL) or another ligament behind the plate 14.

Referring to FIG. 5, a perspective view illustrates the tibia-facing side 36 of the tibial baseplate 14. The keel 32 and the at least one baseplate wing 34 may comprise porous material that encourages bone in-growth.

Figure 6:
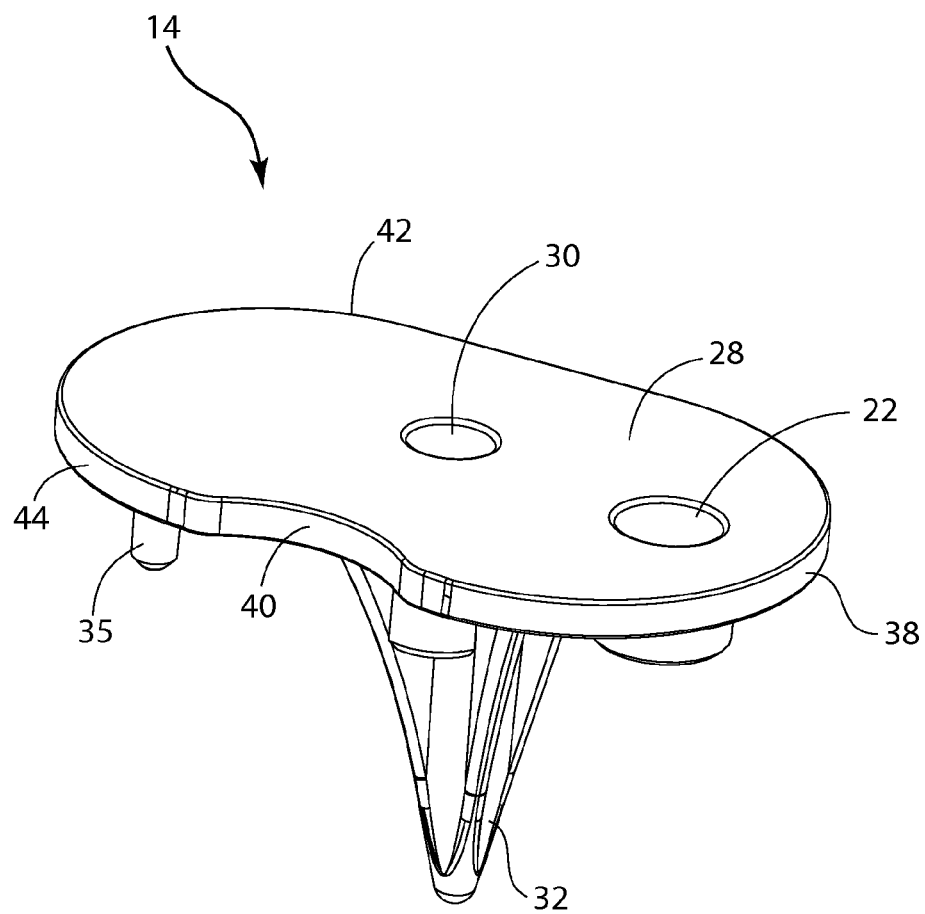
FIG. 6 illustrates a perspective top view of a different embodiment of the tibial baseplate of FIG. 1 with the tibial baseplate aperture and a tibial baseplate cam post aperture on a tibial baseplate bearing surface, a keel and at least one peg.
Figure 6:
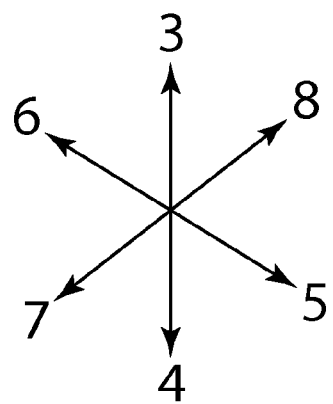
Figure 7:
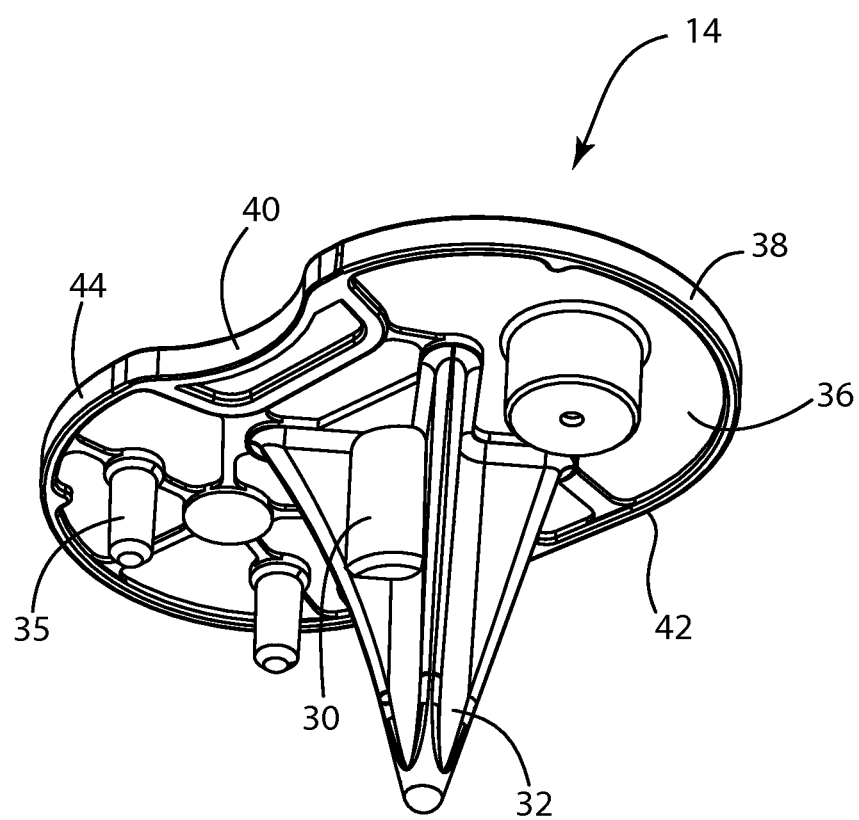
FIG. 7 illustrates a perspective bottom view of the tibial baseplate of FIG. 6 with the at least one peg, the keel, the tibial baseplate aperture and the tibial baseplate cam post aperture.
Figure 7:
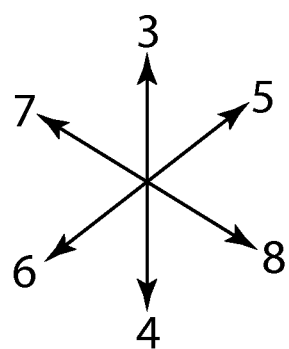

Referring to FIGS. 6 and 7, an alternate embodiment of the keel 32 is present with at least one peg 35. In this and other embodiments of the invention the size, shape and placement of the keel 32 may vary. The pegs 35 may not need to be present at all. Likewise, the tibial baseplate notch 40 can vary in size, shape and placement as well.

Figure 8:
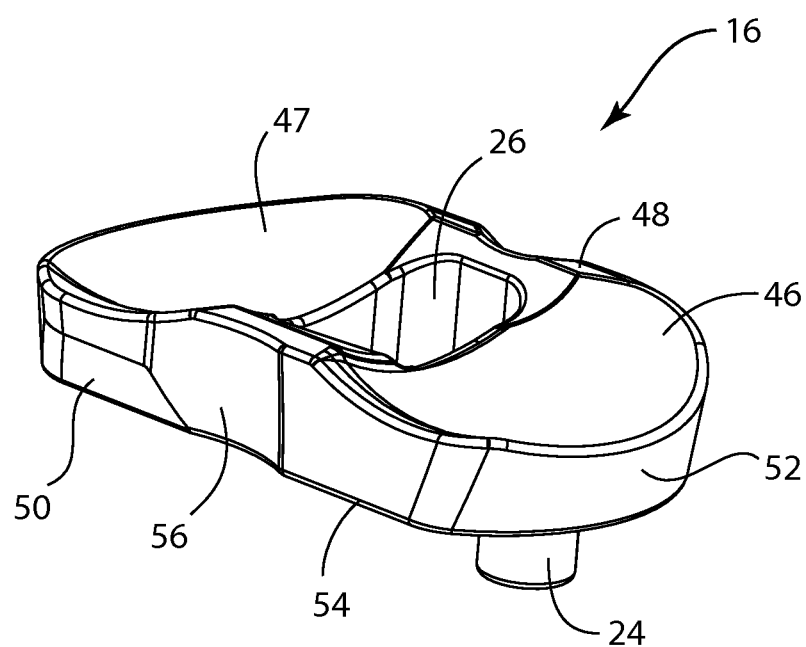
FIG. 8 illustrates a perspective top view of the tibial insert of FIG. 1 with articulating surfaces, a tibial insert notch on the posterior side to allow retention of the posterior cruciate ligament (PCL), a boss and a tibial insert channel.
Figure 8:
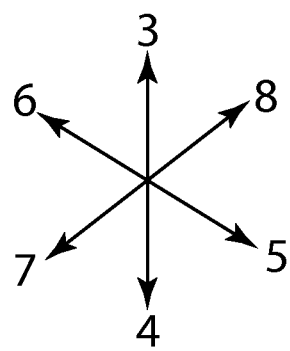

Referring to FIG. 8, the tibial insert 16 comprises a tibial baseplate facing side 54, a femoral implant facing side 55, a tibial insert periphery 52 extending around the tibial insert 16 and a tibial insert channel 26. The periphery 52 may also comprise an anterior facing portion 48 and a posterior facing portion 50. The tibial insert channel 26 may be arc-like shaped and may be generally centrally located extending from the femoral implant facing side 55 to the tibial baseplate facing side 54 and is shaped to slidably fit over the cam post 19. The tibial channel 26 is large enough and shaped to allow some arc-like rotation of the tibial insert 16 after being positioned over the cam post 19. The femoral implant facing side 55 may comprise a first articulating surface 46 and a second articulating surface 47 positioned opposite the tibial insert channel 26. The first articulating surface 46 may be positioned substantially medial to the insert channel 26 and extend from the insert channel 26 to the tibial insert periphery 52. The second articulating surface 47 may be positioned substantially lateral to the insert channel 26 and extend to the tibial insert periphery 52. The articulating surfaces 46, 47 are shaped and curved to align with the femoral implant 12 for when the prosthetic knee 10 is implanted in the patient.

Figure 9:
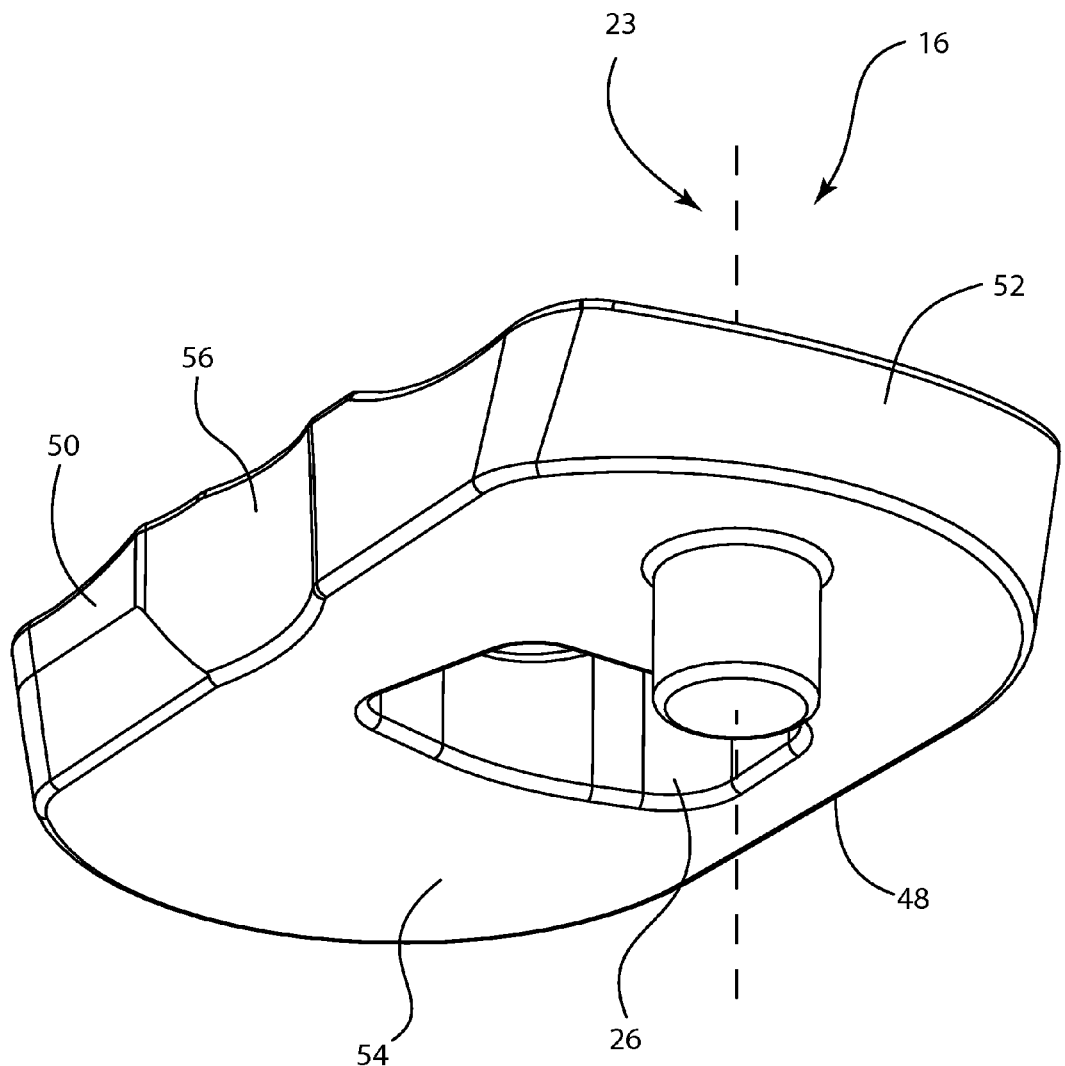
FIG. 9 illustrates a perspective bottom view of the tibial insert of FIG. 8 with the tibial insert channel, the boss, the tibial insert notch, a baseplate facing surface and an axis of rotation generally in the center of the boss.
Figure 9:
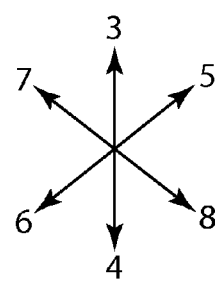

Referring to FIG. 9, the tibial baseplate facing side 54 may be substantially flat with the exception of a boss 24 extending inferiorly, positioned toward the medial side of the tibial baseplate 16 but apart from the tibial insert periphery 52. The flat tibial baseplate facing side 54 may align with the flat superior surface 28 of the tibial baseplate 14 with the boss 24 positioned within the cavity 22 of the tibial baseplate 14. The cavity 22 provides a rotation axis of the tibial insert 16 allowing for some amount of pivot rotation along this rotation axis which allows the tibial insert to perform an arc-like rotation in relation to the tibial insert channel 26 and the cam post 19. The rotation of the tibial insert 16 is constrained by the tibial insert channel 26 positioned over the cam post 19. The tibial insert 16 can be comprised of many biocompatible materials. Polymers may be preferred but metals and ceramics may also be used.

Figure 10:
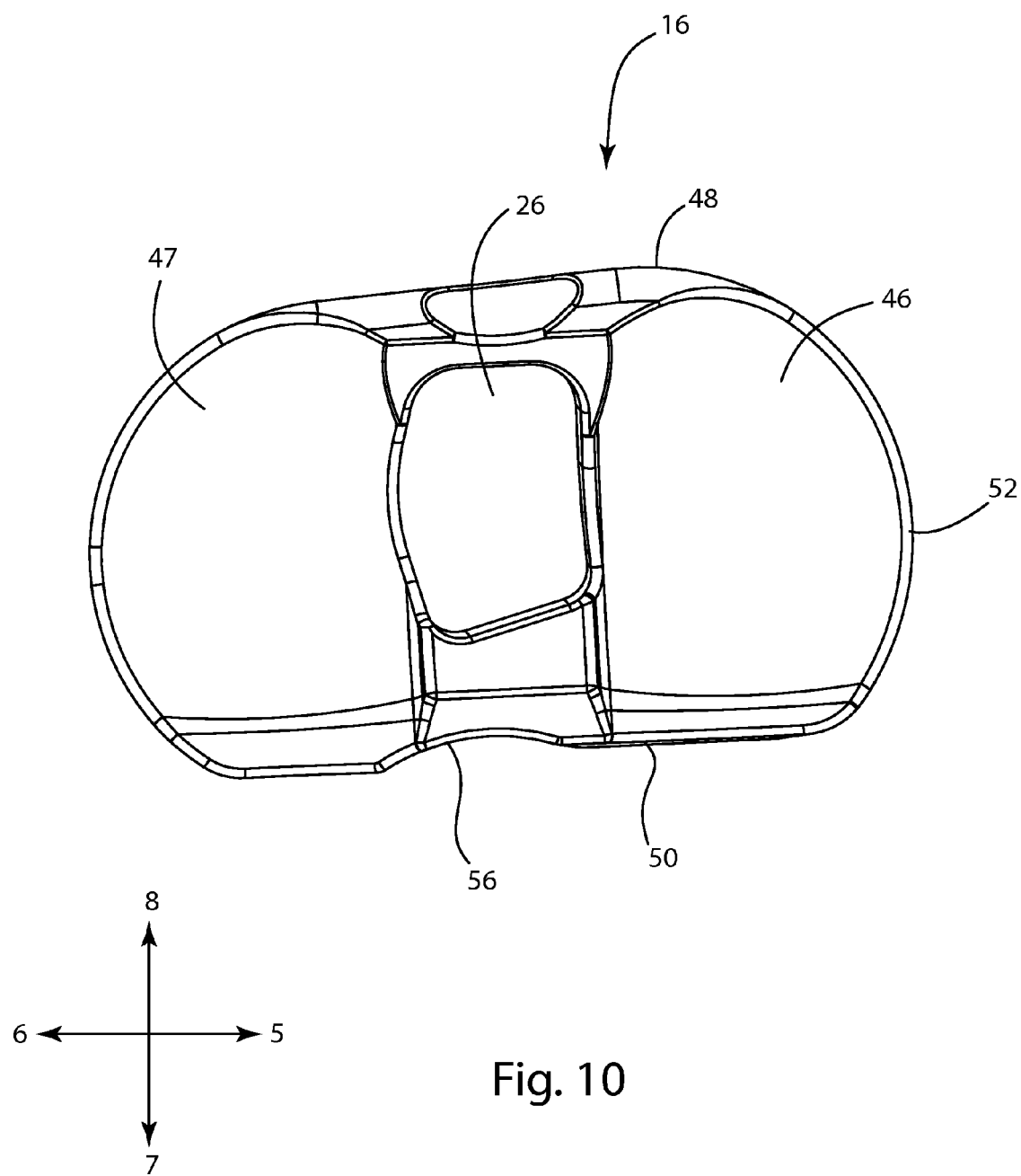
FIG. 10 illustrates a top view of the tibial insert of FIG. 8 with the articulating surfaces, the notch and the channel.

Referring to FIG. 10, a tibial insert notch 56 may be positioned along the tibial insert periphery 52 toward the posterior end of the tibial insert 16. The tibial insert notch 56 may be aligned with the tibial baseplate notch 40 and may allow room for retention of the posterior cruciate ligament (PCL) or another ligament behind the tibial baseplate 14 and the tibial insert 16.

Figure 11:
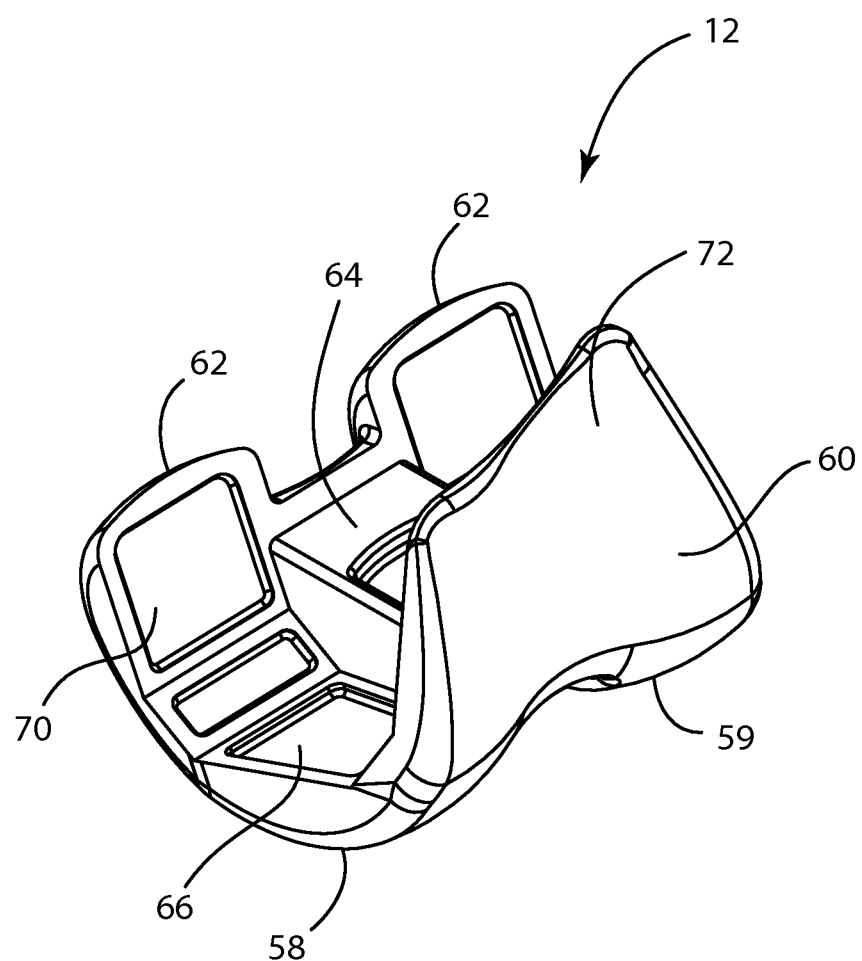
FIG. 11 illustrates a perspective front view of the femoral implant of FIG. 1 with condyles for articulation with the tibial baseplate, a cam feature for interaction with the cam post and a trochlear notch.
Figure 11:
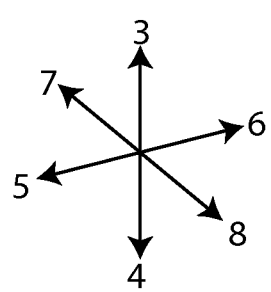

Referring to FIG. 11, the femoral implant 12 has a bone-facing side 70, a trochlear groove 72 on an anterior end 60 end of the femoral implant 12, and a cam feature 64. The trochlear groove 72 adjoins a first condyle 58 and a second condyle 59 extending posteriorly to a posterior end 62 of the femoral implant 12. The cam feature also adjoins the first and second condyles 58, 59. The first condyle and second condyles 58, 59 may curve cephalically, to match the contours of a natural distal end of a femur and are shaped to align with the first articulating surface 46 and the second articulating surface 47 of the tibial insert 16 respectively. The radius of curvature of the condyles 58, 59 may relatively match the same curvature of the articulating surfaces 46, 47 of the tibial insert 16. The condyles 58, 59 may be polished to minimize wear between the condyles 58, 59 and the articulating surfaces 46, 47 of the tibial insert 16. If the tibial insert 16 is also made of metal, including those metals named herein, it may also be polished to minimize wear.

The bone-facing side 70 may have a bone-facing surface 66 which may comprise a porous material to encourage bone in-growth. A gap 68 between the condyles 58, 59 is generally a fixed height, but the condyles 58, 59 may be of various widths, sizes and curvatures depending on the specific anatomy of the patient or tibial insert 16. The surface curvature of the condyles 58, 59 may also vary to match the curvature of the specific tibial insert 16 chosen for the patient's mobility requirements.

Figure 12:
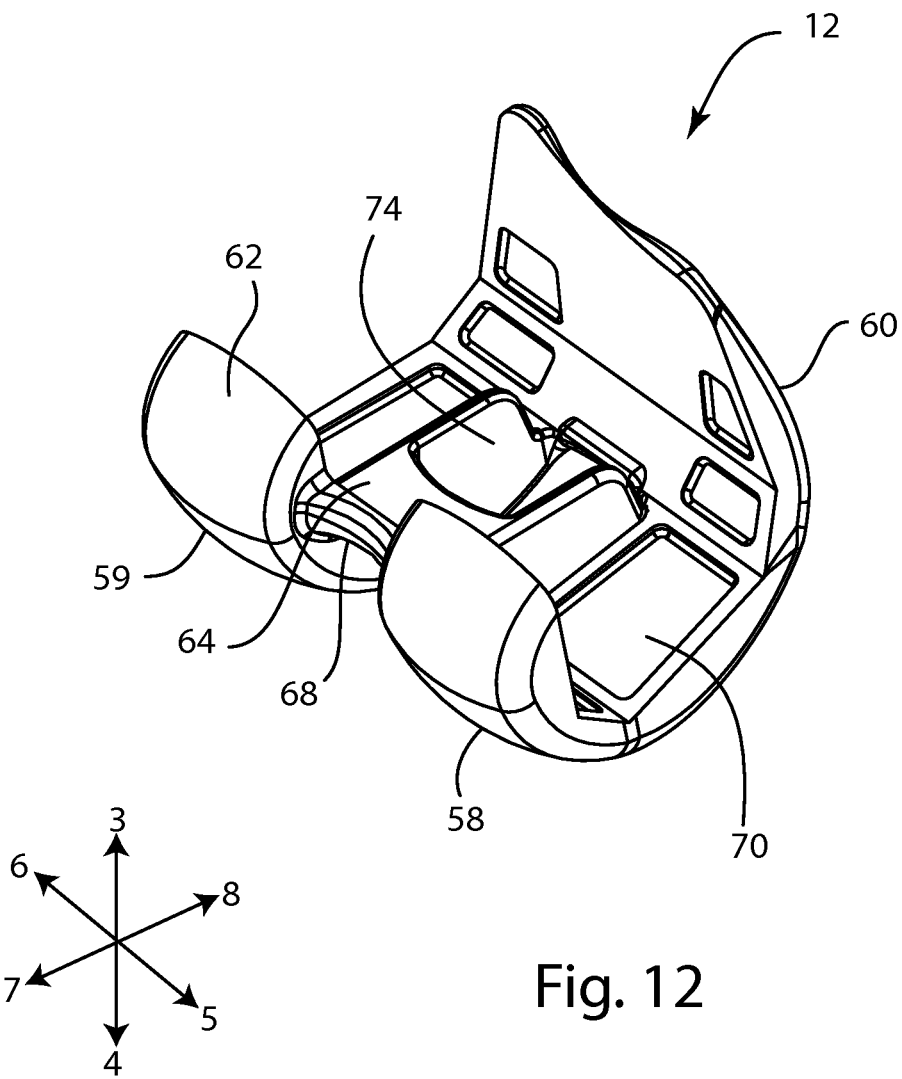
FIG. 12 illustrates perspective back view of the femoral implant of FIG. 11 with a femoral implant opening for engagement with the cam post, a condyle gap between the condyles and condyles.

Referring to FIG. 12, the femoral implant 12 may further comprise an opening 74 shaped and positioned to receive the cam post 19. The cam post 19 slidably inserts into the opening 74 and a posterior side of the cam post 19 engages the cam feature 64 on an anterior side of the cam feature 64 during knee flexion.

Figure 13:
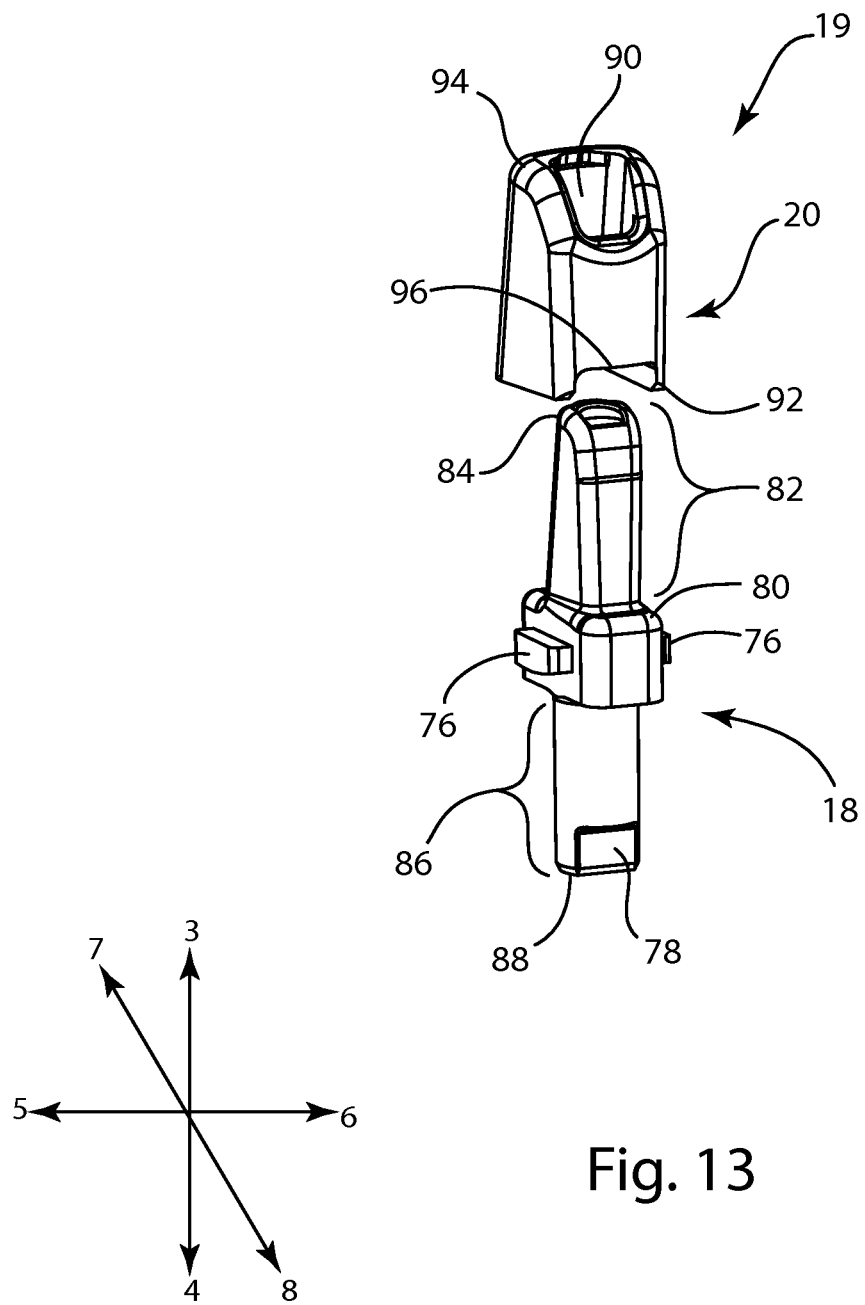
FIG. 13 illustrates an exploded perspective view of the cam post of FIG. 2 with a cam post core and an outer sleeve.

Referring to FIG. 13, the cam post 19 has the cam post core 18 and the outer sleeve 20. The cam post core 18 has an inferior end 88, a superior end 84, a superior portion 82, an inferior portion 86 and an intermediate portion 80 between the superior and inferior portions 82, 86. The intermediate portion 80 may of greater width than the inferior and superior portions 82, 86, and may comprise wings 76 extending laterally and medially and are positioned as a stop to engage the outer sleeve 20. Toward the inferior end 88 the cam post core may have a Morse taper or similar taper or pin which engages in the tibial baseplate hole 30 and a core notch 78 which may act like a key fit. The intermediate portion may also vary in height (superiorly to inferiorly) depending on variations of the patients anatomy.

Figure 14:
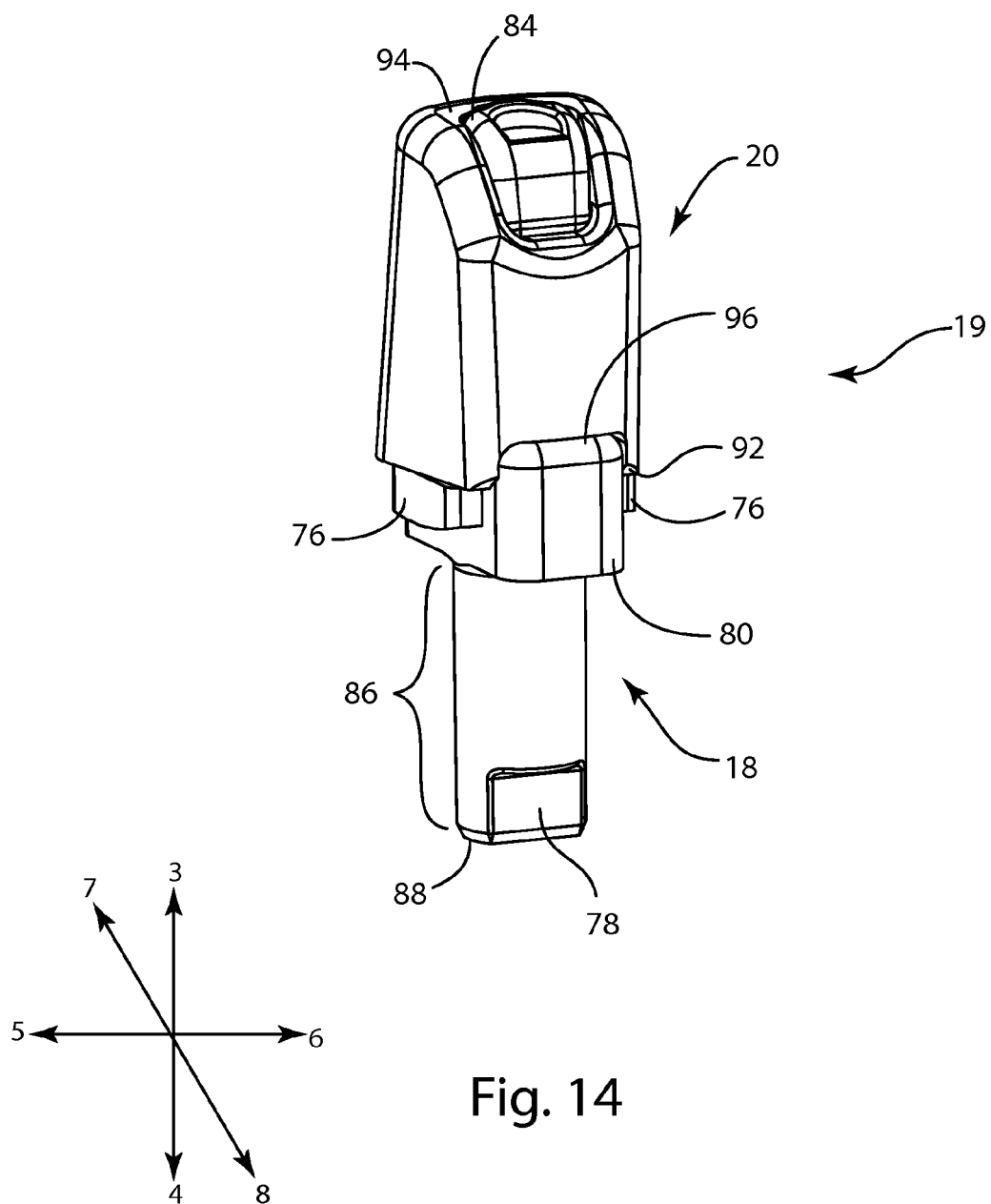
FIG. 14 illustrates the cam post of FIG. 13 with the outer sleeve at least partially encircling the cam post core.

Referring to FIGS. 13 and 14, the superior portion 82 is shaped to slidably receive the outer sleeve 20. The outer sleeve 20 has a sleeve channel 90, a superior end 94 and an inferior end 92. The sleeve channel 90 is shaped to slide over the superior portion 82 at least partially surrounding the superior portion 82. The outer sleeve is positioned around the superior portion 82 and slides onto the superior portion 82 until the sleeve inferior end 92 engages the wings 76 of the intermediate portion 80 of the cam post 19. The outer sleeve 20 may comprise a sleeve notch 96 toward the inferior end 92 of the outer sleeve 20 which may communicate with the intermediate portion 80 and receive a portion of the intermediate portion 80 within the sleeve notch 96, providing greater stability and fixation of the cam post core 18 to the outer sleeve 20. The sleeve notch 96 may also provide rotational stops so the sleeve is unable to rotate when snapped into engagement with the cam post core 18. The outer sleeve 20 may be secured to the cam post core 18 through snap fit features. After the outer sleeve 20 is positioned around the superior portion 82 of the cam post core 82 the cam post core superior end 84 and the outer sleeve superior end 94 may be flush.

The cam post core 18 may be made of cobalt-chrome or its alloys, titanium or its alloys, stainless steel or any other biocompatible metal, ceramic or polymer. The outer sleeve 20 may be preferably made of polymer; however, it may also be comprised of many other biocompatible materials including ceramics and metals. In addition the cam post core 18 and the sleeve 20 may be one piece instead of two pieces.

Referring back to FIG. 3, the tibial baseplate 14 is secured to the resected tibia 2. The cam post 19 may be secured to the tibial baseplate 14 using a Morse taper or similar taper or pin feature (the core notch 78 of the cam post core 18). The tibial insert 16 is positioned over the cam post 19 and the boss 24 of the tibial insert 26 is positioned within the cavity 22 of the tibial baseplate providing an axis of rotation 23. The tibial insert channel 26 may contain a metal band lining the channel 26. The sleeve 20 of the cam post 19 may be polyethylene and may extend from the sleeve superior end 94 to the tibial baseplate 14 when the cam post 19 is correctly positioned in the baseplate 14. This feature of the metal band and extension of the polyethylene sleeve 20 may minimize stresses on the tibial insert 16 when it contacts the cam post 19 and stops.

The femoral implant 12 is secured to the resected femur 1. The cam post is then positioned within the opening 74 of the femoral implant 12 engaging the cam feature 64 during knee flexion. The cam feature 64 provides rollback and femoral external rotation during knee flexion. The cam post 19 after engaging the cam feature 64 allows two fully guided rotational axes and provides anterior and posterior stabilization features. The cam post 19 engages the cam feature 64 resisting posterior tibial translation. The cam post 19 also engages the tibial insert channel 26 to restrict anterior displacement of the tibial insert and the tibia as well.

One fully guided rotational axis is between the femoral implant 12 and the tibial insert 16 by engagement of the condyles 58, 59 with the articulating surfaces 46, 47. A second fully guided rotational axis is between the tibial insert 16 and the tibial baseplate 14 by aligning the tibial baseplate facing side 54 with the flat superior surface 28 of the tibial baseplate 14. The second rotational axis is accomplished by the positioning of the boss 26 within the cavity. The first and second rotational axes closely match the motion of the natural knee and are suitable for hard-on-hard bearing contact surfaces, such as the use of cobalt-chrome, ceramic, composite or other hard materials for the femoral implant 12, tibial insert 16 and tibial baseplate 14, which may lead to longer durability of the prosthetic knee. The potential advantage of using exclusively hard materials is that polyethylene debris can be eliminated and wear particle generation can be reduced, reducing the chance of osteolysis and implant loosening. However, to be able to use exclusively hard materials requires a fully guided motion conforming mobile bearing design—meaning a design in which relative motion between any two parts occurs along only one path.

Cobalt-chrome and its alloys are not the only hard-on-hard material that may be used, other examples include, but are not limited to, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, and many other biocompatible materials and coatings.

Another advantage of the features recited herein is that this design provides knee motion during flexure closer to the natural knee. Two other benefits of these novel features is that (1) the cam post 19 can provide both anterior and posterior rotational stops for the tibial insert 16, and (2) the cam post 19 can independently provide anterior and posterior translation stops for the femoral implant 12. These benefits of the design contribute to the overall stability of the prosthetic knee, eliminating the risk of bearing spin out, and limiting anterior tibial translation which is provided by the anterior cruciate ligament in the normal knee 10.

In alternative embodiments, the various components shown and described herein may have different sizes, configurations (such as size of the keel, shape and size of the cam post, the width of tibial insert, and the like) material properties, and other variations to adapt them to variations in patient anatomy. If desired, multiple versions of each of the femoral implant, tibial baseplate, and tibial insert components may be provided together in a single kit to enable a surgeon to select the best set of components for a patient.

Figure 15:
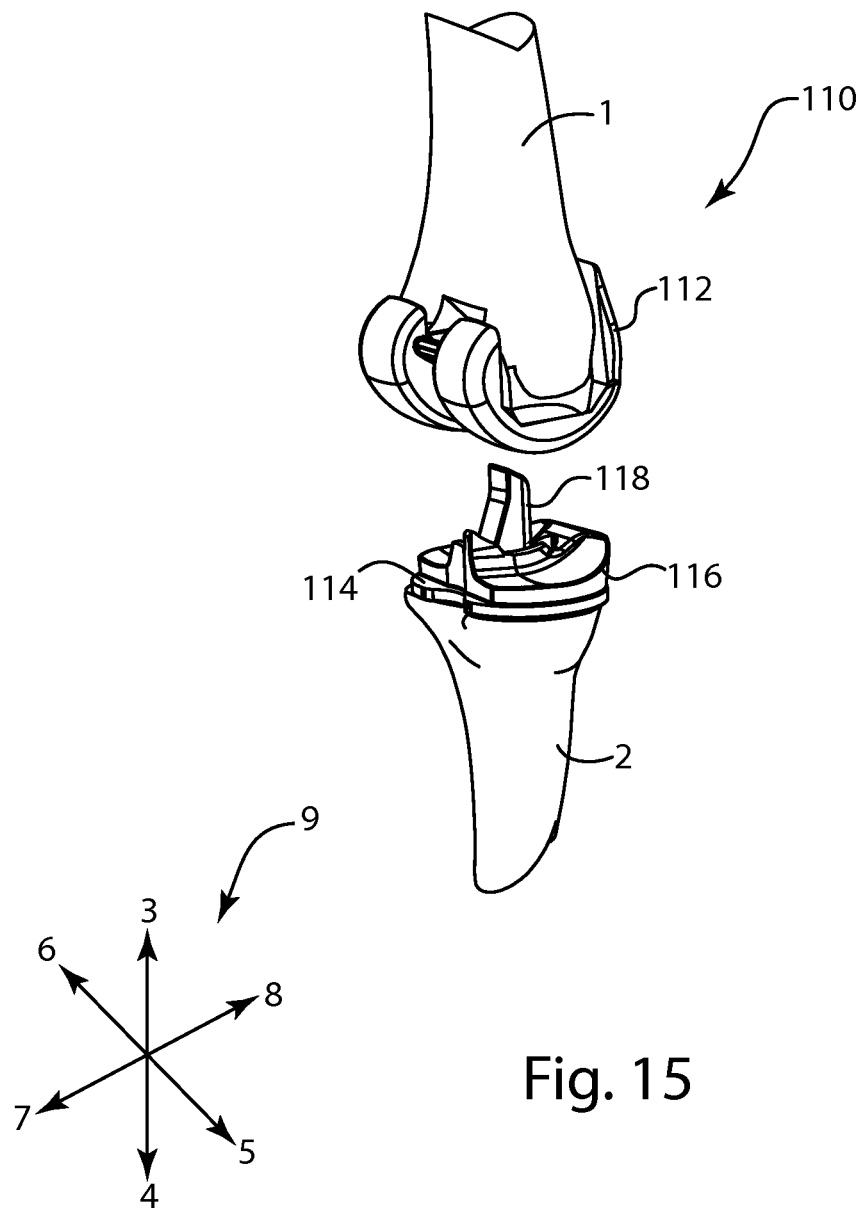
FIG. 15 illustrates a perspective view of an alternate embodiment of the prosthesis with a femur, a tibia, femoral implant, a cam post a tibial insert and a tibial baseplate.

Referring to FIG. 15, an alternate embodiment of a prosthetic knee 110 includes a femoral implant 112, a tibial baseplate 114, a tibial insert 116 and a cam post 118. The interaction between each of the components is similar to the previous embodiment.

Figure 16:
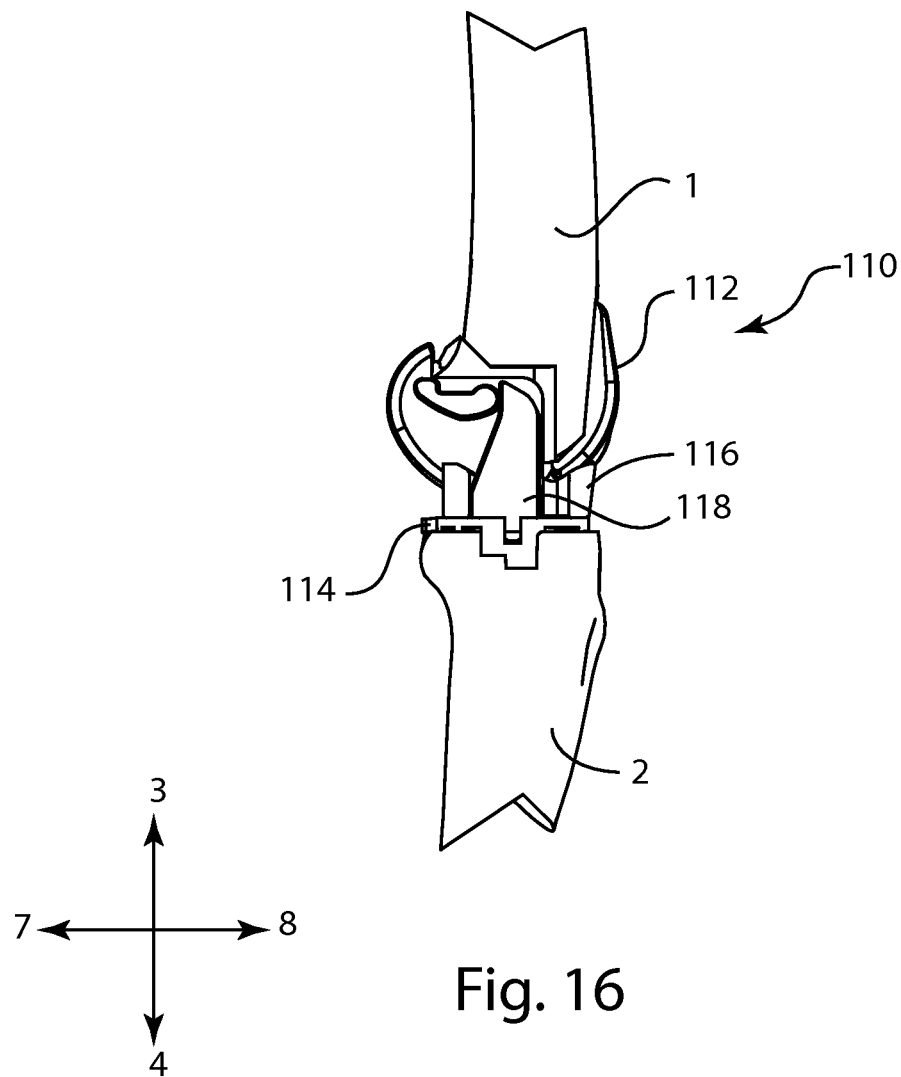
FIG. 16 illustrates a cross sectional side view of the prosthesis of FIG. 15 with the femoral implant the cam post, the tibial insert and the tibial baseplate.

Referring to FIG. 16, similar to the previous embodiment the femoral implant 112 engages the tibial insert 116 and the cam post 118 may engage a cam feature 120 during flexion of the knee providing anterior and posterior translational stops for the femoral implant. The cam post 118 is fixed to the tibial baseplate 114 and passes through a tibial insert channel 130 (better depicted in FIGS. 19 and 20). The cam post 118 provides anterior and posterior rotational stops for the tibial insert 116.

Figure 17:
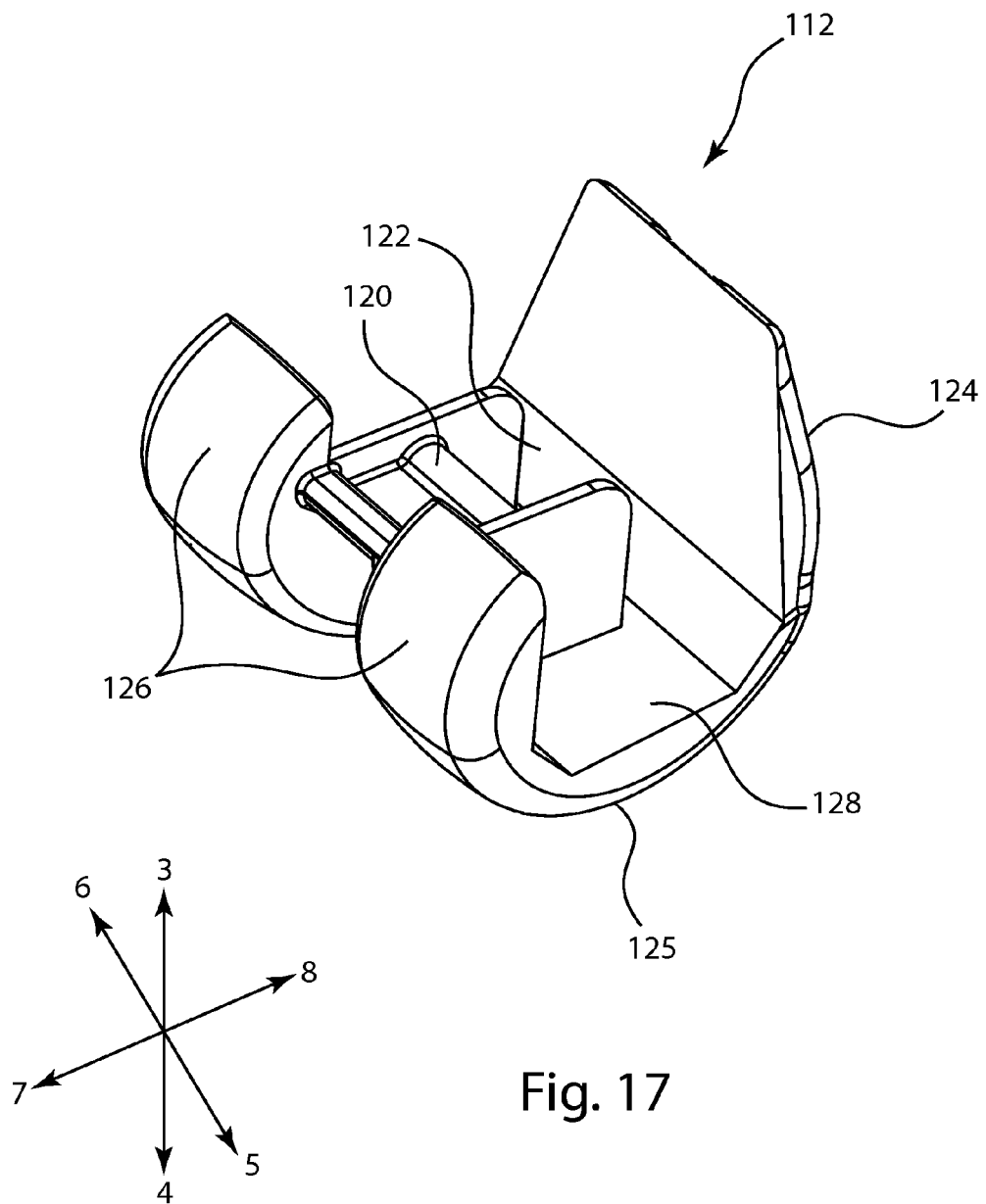
FIG. 17 illustrates a perspective back view of the femoral implant of FIG. 15 with a cam feature, condyles, and a femoral opening.

Referring to FIG. 17, the femoral implant 112 includes condyles 125 which interact with and are highly conforming with the tibial insert 116. The femoral implant also includes a bone facing side 128 that is configured to engage a resected femur. Between an anterior end 124 and a posterior end 126 lies a femoral implant opening 122 shaped to receive the cam post 118 and immediately posterior to the opening 122 is a cam feature 120 which is positioned and shaped to engage the cam post 118 during flexion of the prosthetic knee 110. The cam feature 120 provides rollback and femoral external rotation during knee flexion.

Figure 18:
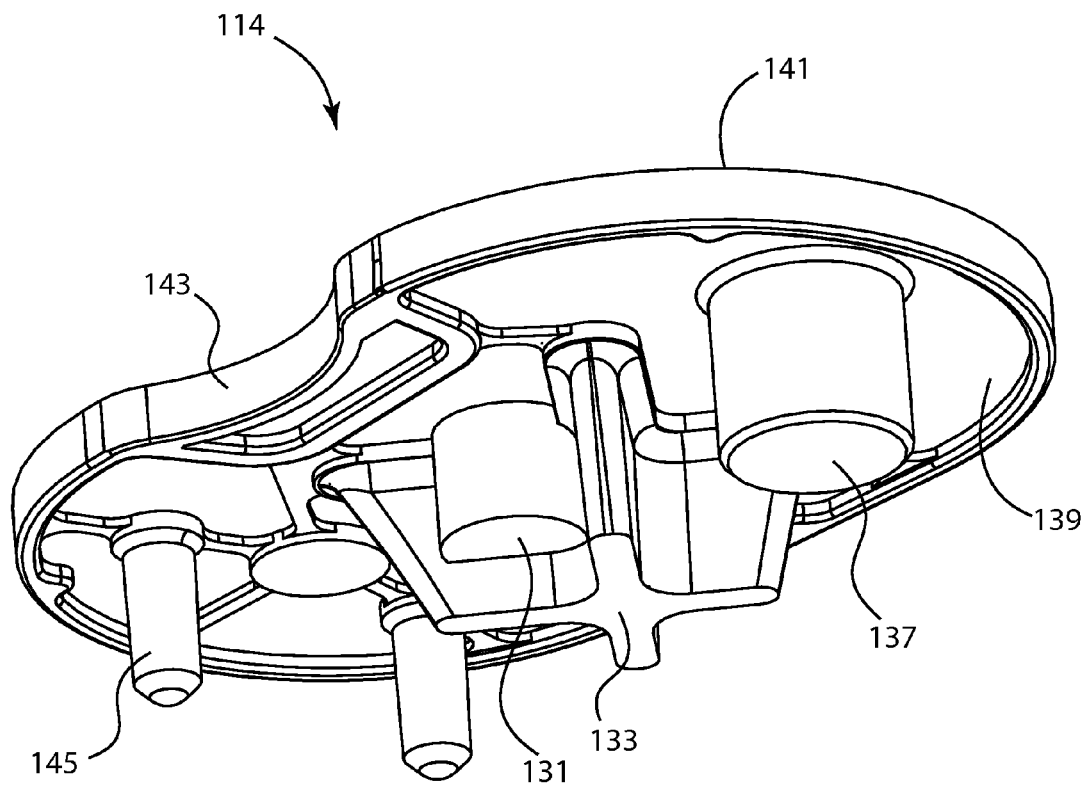
FIG. 18 illustrates a perspective bottom view of the tibial baseplate of FIG. 15 with a keel (smaller than the keels of FIGS. 4-7), at least one peg, a cavity to receive a boss of the tibial insert and tibial facing side and a notch on the posterior side for retention of the PCL.
Figure 18:
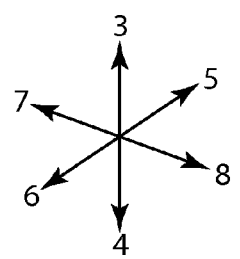

Referring to FIG. 18, the tibial baseplate 114 is similarly shaped to the previous embodiment's baseplate 14. However, a keel 133 may be shorter. The tibial baseplate 114 may comprise the same elements of the previous embodiment and they may carry out the same functions of the previous embodiment as well. The parts of the tibial baseplate which may mirror the previous embodiment include a tibial baseplate hole 131 to engage the cam post 118, a tibial baseplate cavity 137 to engage a boss 132 (depicted in FIG. 19), a tibia facing surface 137 configured to engage the resected tibia 2. The features may also include at least one peg 145 extending from the tibia facing surface 137 to engage the tibia 2. A tibial baseplate superior surface 141 is generally flat allowing for interaction with the tibial insert 116 similar to the previous embodiment. The tibial baseplate may also further comprise the tibial baseplate notch 143 which may allow room for retention of the posterior cruciate ligament (PCL) or another ligament behind the tibial baseplate 114 and the tibial insert 116.

Figure 19:
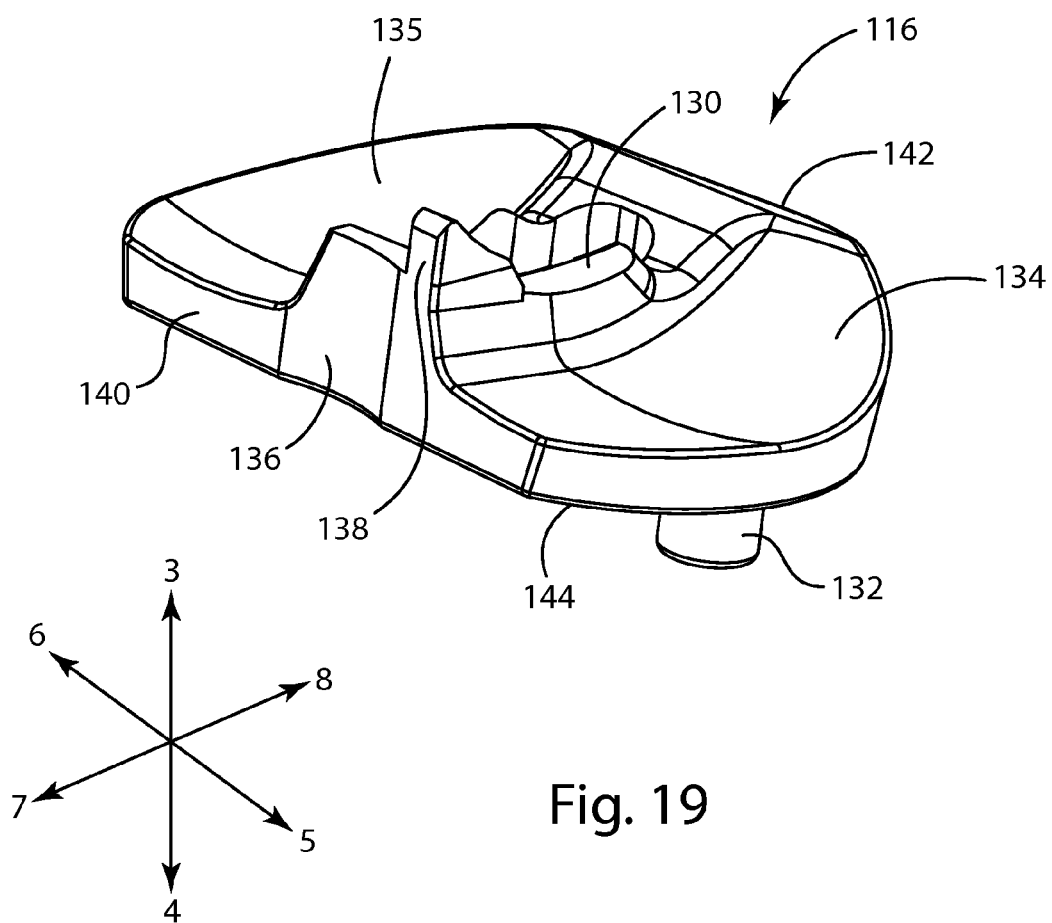
FIG. 19 illustrates a perspective top view of the tibial insert of FIG. 15 with articulating surfaces to interact with the condyles of the femoral implant of FIG. 17, a boss to interact with the cavity of the tibial baseplate of FIG. 18, a medial peak, a tibial insert channel for passage of the cam post, and a notch on the posterior side of the tibial insert for retention of the PCL.
Figure 20:
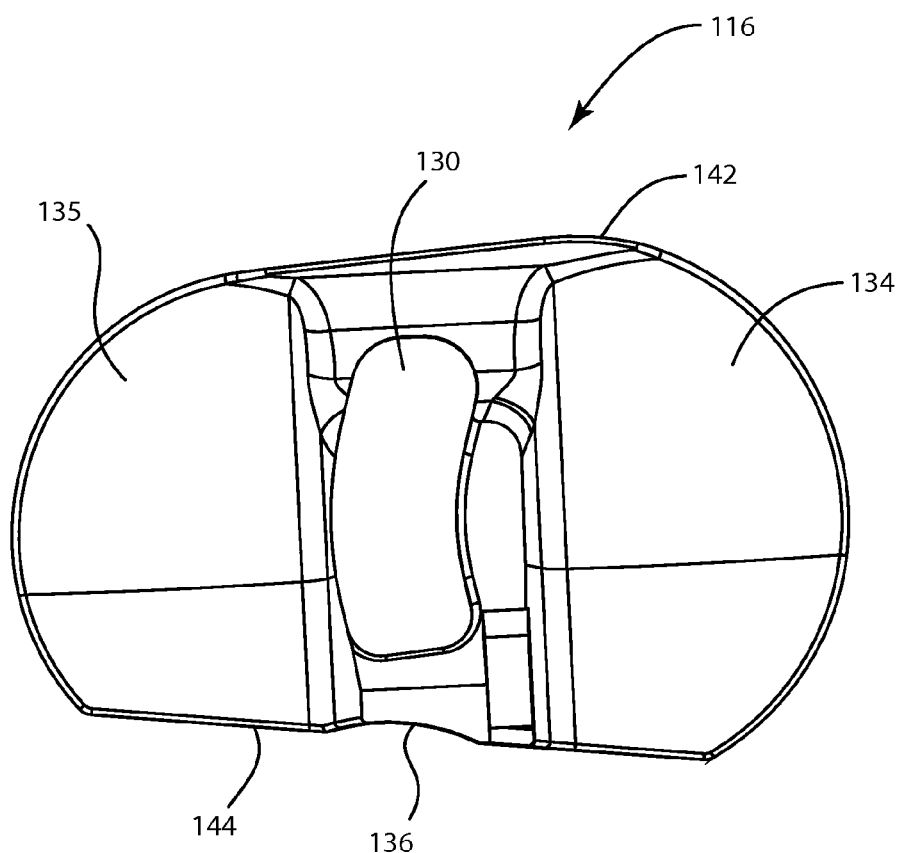
FIG. 20 illustrates a top view of the tibial insert of FIG. 19 with a channel, a notch and articulating surfaces.
Figure 20:
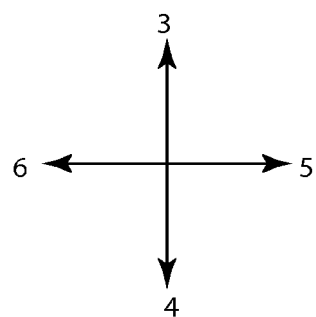

Referring to FIGS. 19 and 20, the tibial insert 116 may comprise many of the same elements with the same function and design as the previous embodiment. However, an anterior end 142 may have a greater height than a posterior end 140 of the tibial insert 116. In addition a peak 138 may extend superiorly and may be positioned toward the posterior end 140 of the tibial insert 116 to interact between, and are highly conforming with, the condyles 125 of the femoral implant 112. The other characteristics of the tibial insert 116 include medial and lateral articulating surfaces 134, 135 sculpted and curved to align with the condyles 125 of the femoral implant, as well as the tibial insert channel 130 which may be somewhat arc shaped (Refer to FIG. 17), and which is large enough to slidably receive the cam post 118 and allows for anterior posterior rotation along the arced channel 130. Furthermore the tibial insert 116 includes the tibial insert baseplate facing surface 144 which is generally flat configured to align with the generally flat tibial baseplate superior surface 144, and the boss 132 shaped to align and be received within the cavity 137 to provide a rotational axis for the anterior posterior rotation of the tibial insert 116. The tibial insert 116 also includes the tibial insert notch 136 which may allow room for retention of the posterior cruciate ligament (PCL) or another ligament behind the tibial baseplate 114 and the tibial insert 116.

Figure 21:
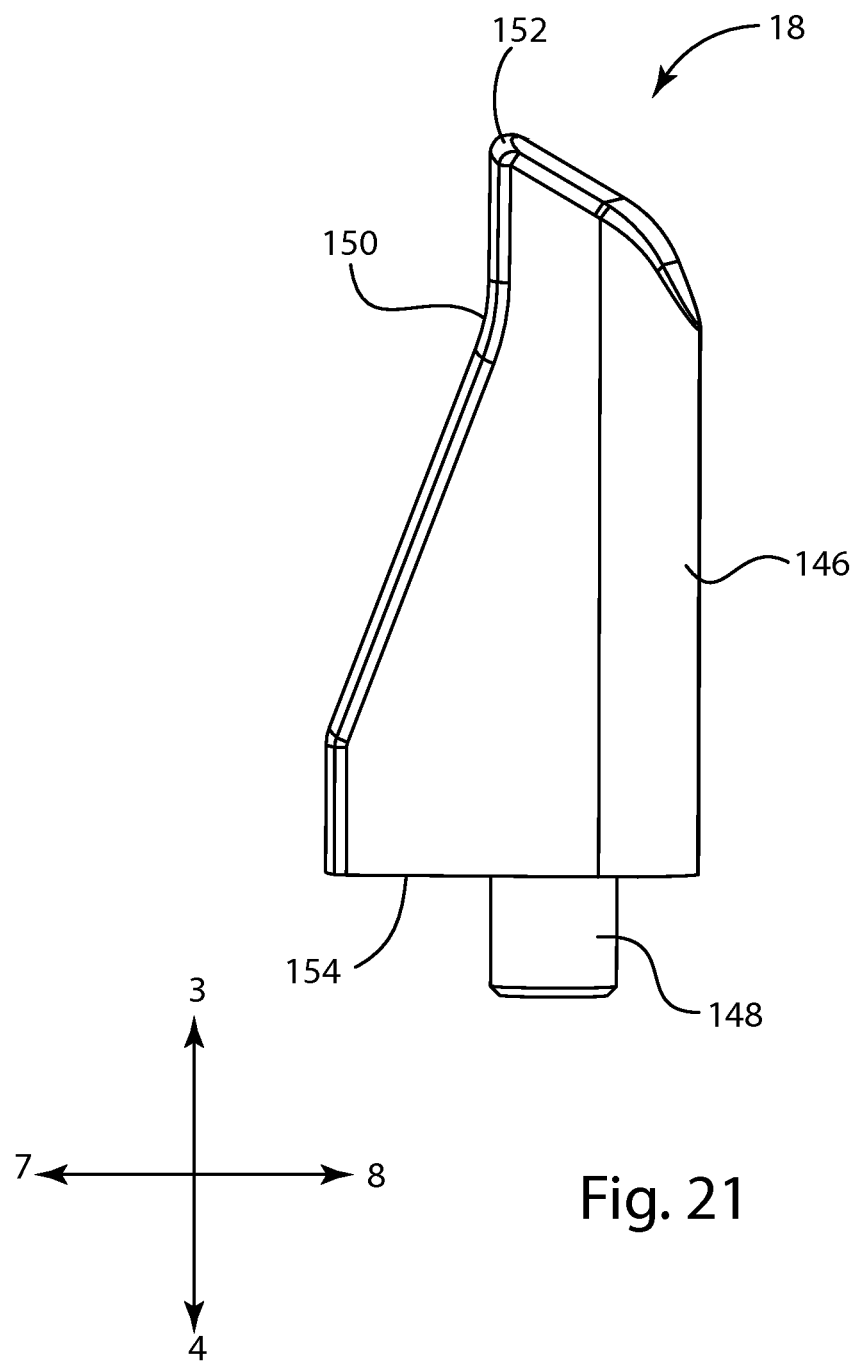
FIG. 21 illustrates a side view of the cam post of FIG. 15 with a cam post body superior end and an inferior end with a groove between the superior and inferior ends and a cam post boss extending inferiorly from the inferior end of the cam post.
Figure 22:
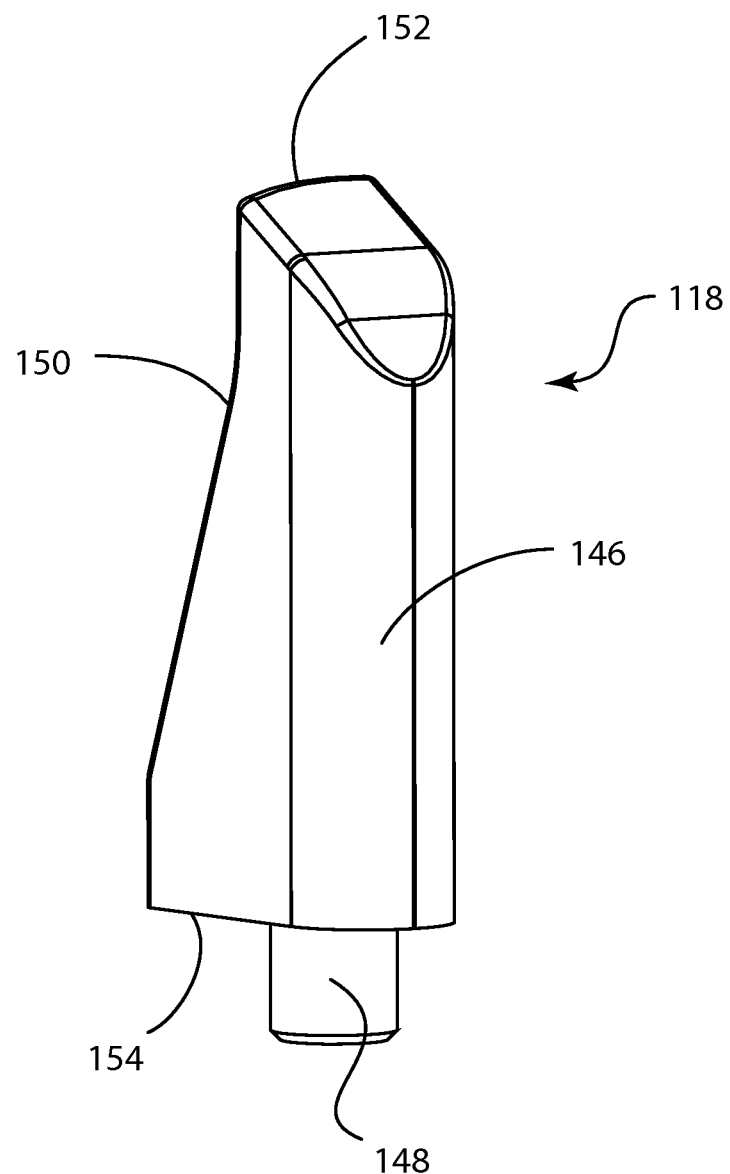
FIG. 22 illustrates a perspective front view of the cam post of FIG. 21.
Figure 22:
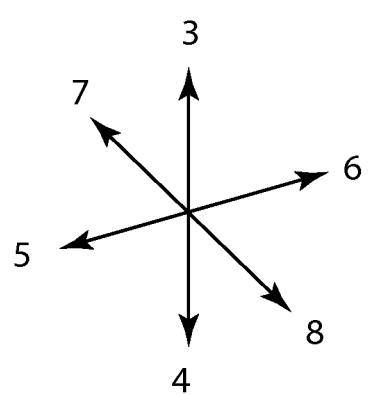

Referring to FIGS. 21 and 22, the cam post 118 includes a cam post body 146 with a wider inferior end 154 than a superior end 152 and a cam post boss 148 extending inferior shaped to engage the tibial baseplate hole 131. The cam post 118 is fixed to the tibial baseplate 114 through the interaction between the tibial baseplate hole 131 and the cam post boss 148.

The cam post 118 decreases in width from the inferior end 154 to the superior end 152. Between the superior end 152 and the inferior end 154 is a groove 150 shaped to engage the cam feature 120 of the femoral implant 112 during flexion of the prosthetic knee 110.

The interaction each of the components is generally similar to the previous embodiment with differences in structure only (refer to FIG. 13). The features recited herein are that this design provides knee motion during flexure closer to the natural knee. Benefits of these novel features include the same features as previously recited which are (1) the cam post 118 can provide both anterior and posterior rotational stops for the tibial insert 116, and (2) the cam post 118 can independently provide anterior and posterior translation stops for the femoral implant 112. These benefits of the design contribute to the overall stability of the prosthetic knee 110.

Figure 23:
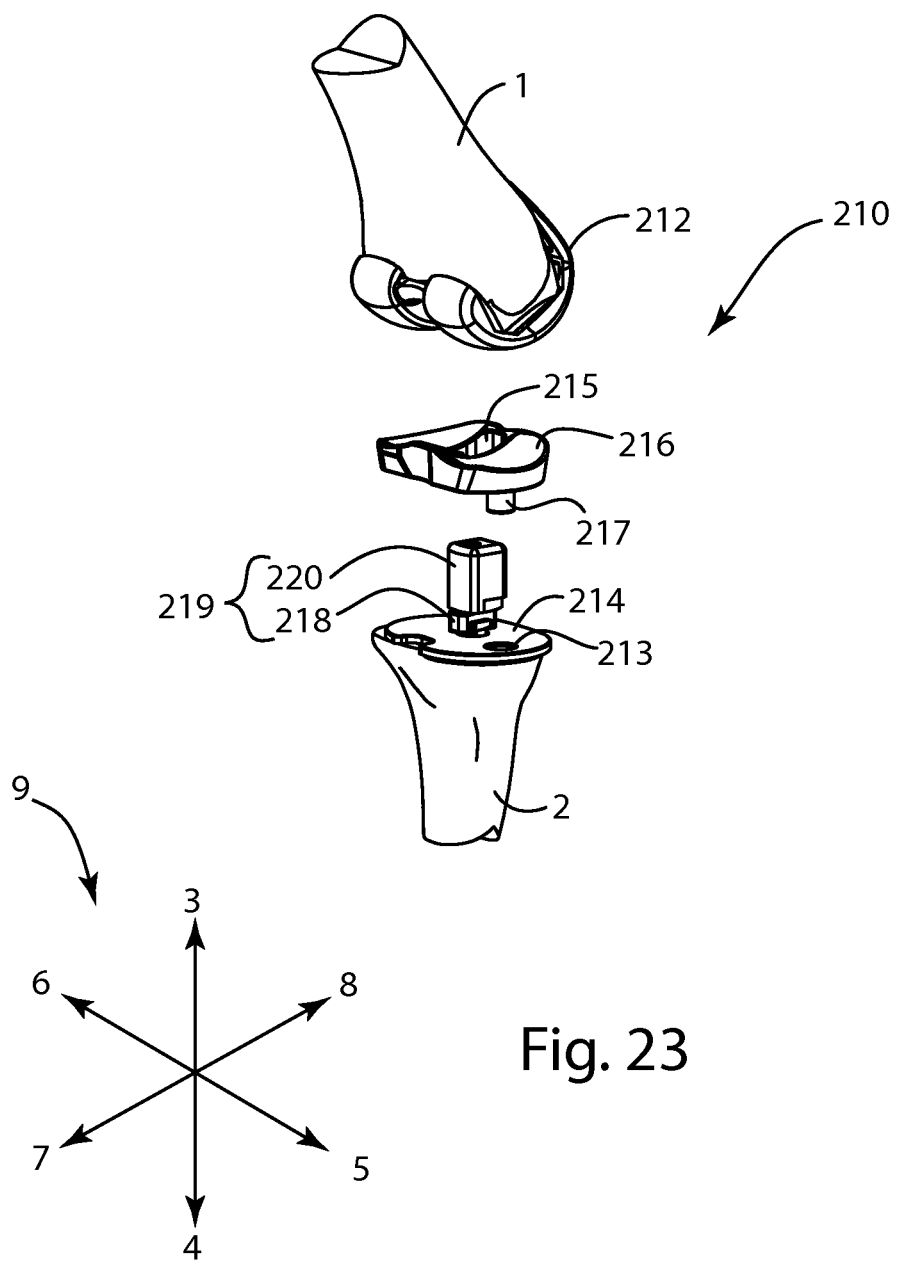
FIG. 23 illustrates an exploded perspective back view of an alternate embodiment of the prosthesis of FIG. 1 with a femur, a tibia, femoral implant, a cam post, a tibial insert and a tibial baseplate.
Figure 24:
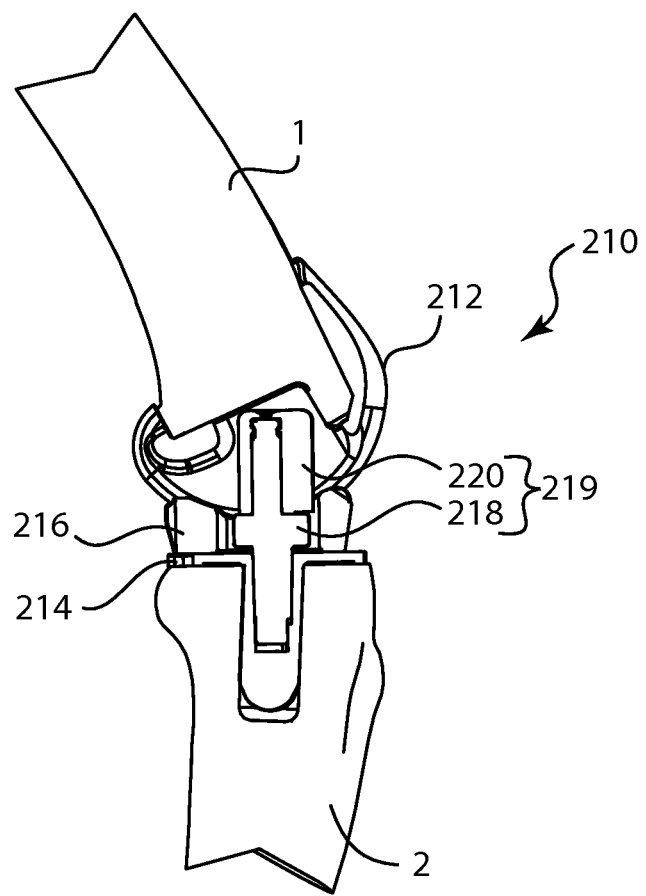
FIG. 24 illustrates a cross sectional side view of the prosthesis of FIG. 23 with a femoral implant, a cam post, a tibial insert and a tibial baseplate.
Figure 24:
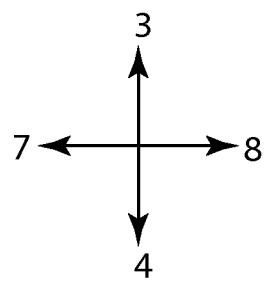

Referring to FIGS. 23 and 24, another alternate embodiment of a prosthetic knee 210 includes the same or similar components of the previous embodiments with a femoral implant 212, a tibial baseplate 214, a tibial insert 216 and a cam post 219 comprising a cam post core 218 and a sleeve 220. This specific embodiment is intended to prevent varus/valgus displacement and may be more suitable for those patients who have insufficient, lax or absent medial or lateral stabilizing ligaments. The tibial insert has a tibial insert channel 215 (similar to those channels 26 and 130 in the two previous embodiments) and a boss 217 (similar to those bosses 24 and 132 of the previous embodiments). The tibial baseplate 214 has a cavity toward the medial side 213.

Figure 25:
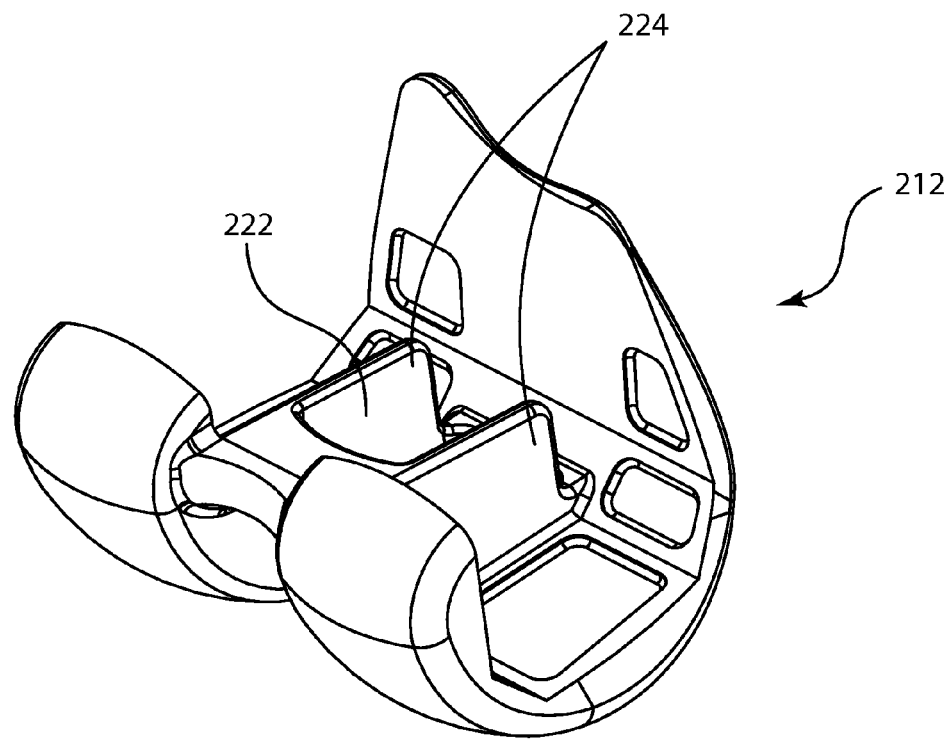
FIG. 25 illustrates a perspective back view of a femoral implant with a femoral opening engaging the cam post and opening walls for stabilization of the cam post and the prosthesis.
Figure 25:
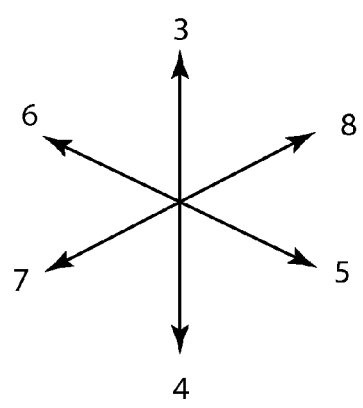

The components are substantially similar to the previous embodiments. The tibial insert has a tibial insert channel 215 (similar to those channels 26 and 130 in the two previous embodiments) and a boss 217 (similar to those bosses 24 and 132 of the previous embodiments). However, referring to FIG. 25, the femoral implant 212 which has a femoral opening 222 may also comprise opening walls 224 which engage the cam post sleeve 220 of the cam post 219 preventing varus/valgus distraction and provide greater medial/lateral stabilization (refer to FIG. 23).

Figure 26:
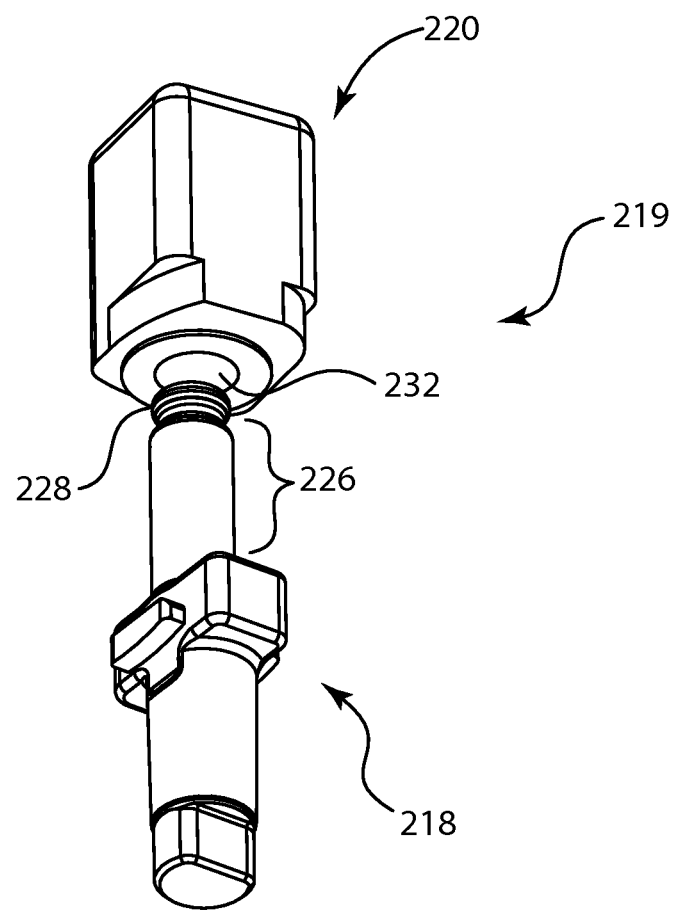
FIG. 26 illustrates a perspective view of the cam post of FIG. 23 with a cam post core with a snap feature for engaging a cam post sleeve.
Figure 26:
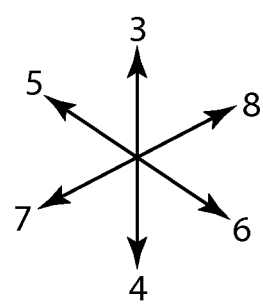

Referring to FIG. 26, the cam post core 218 comprises most of the same features of the cam post core 18 of FIGS. 13 and 14; however, a cam post core superior portion 226 may be substantially circular in cross section with a snap feature 228 on the superior end shaped to snap into engagement with the sleeve 220. The sleeve 220 may be substantially rectangular in cross section, however any shape that would enable engagement with the femoral implant 212 opening walls 224 is sufficient. The sleeve 220 has a cylindrical bore 232 passing longitudinally therethrough and a taper 230 toward the inferior end of the sleeve 220 to prevent any obstruction of the sleeve with the tibial insert channel 215. The superior portion 226 is at least partially inserted into the sleeve 220 until the two components snap into engagement. The sleeve 220 may rotate around the center axis of cam post core 218 after the sleeve is positioned around the superior portion 226. The cam post core 218 may be polished to minimize wear between the cam post core 218 and the sleeve 220. Internal stops (not shown) may be added to prevent complete rotation of the sleeve around the center axis of the cam post core 218.

Figure 27:
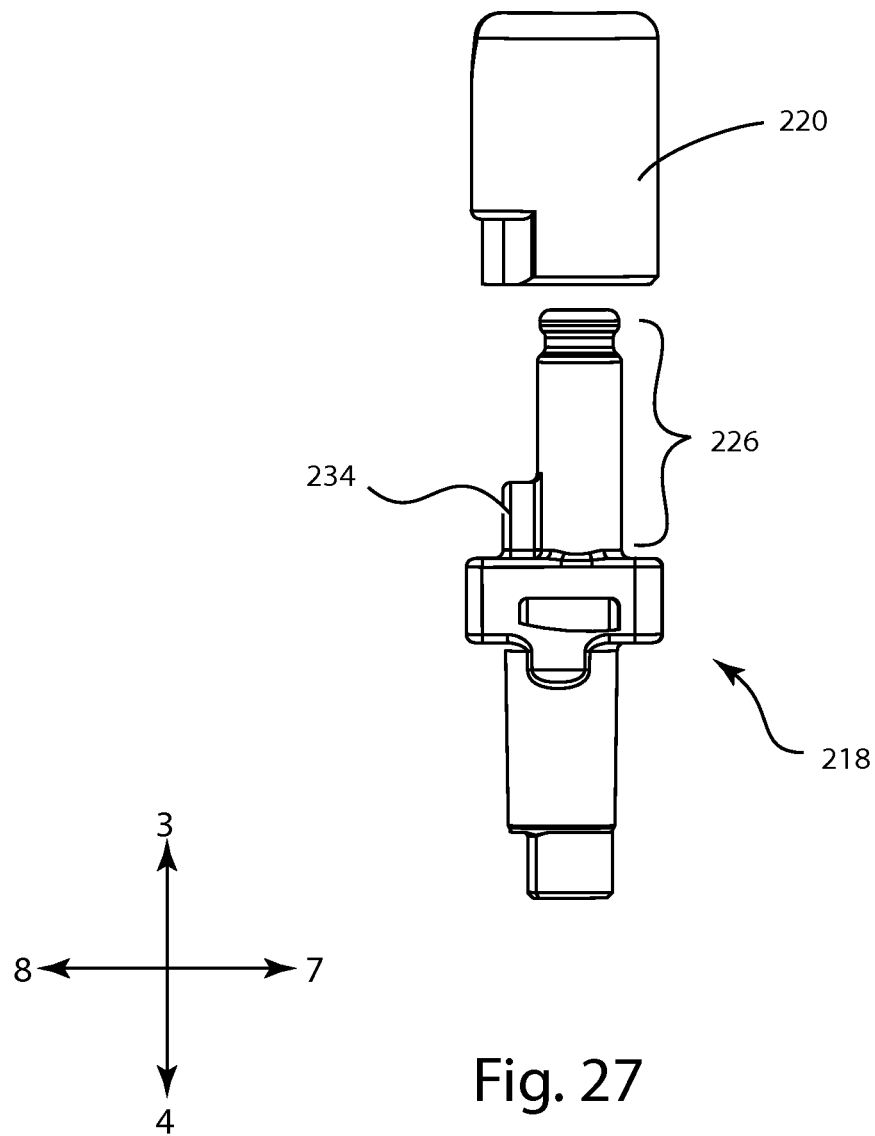
FIG. 27 illustrates a side view of an alternate embodiment of a cam post of FIG. 26 with a cam post sleeve and a cam post core the cam post core having a ridge to prevent movement of the cam post sleeve after it engages the cam post core.
Figure 28:
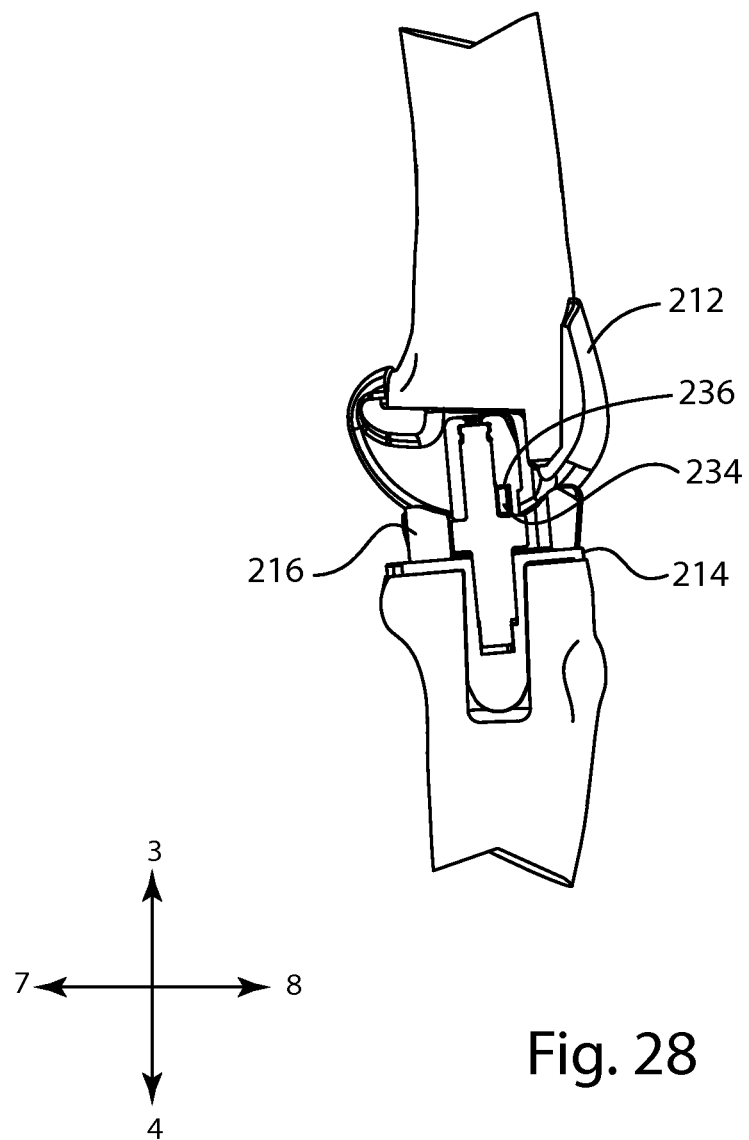
FIG. 28 illustrates slightly different embodiment of the prosthesis of FIG. 23 (the only difference is in the cam post of FIG. 26) showing the cam post of FIG. 27.

Referring to FIGS. 27 and 28, an alternate embodiment of the cam post core 218 may have a ridge 234 which may extend either posteriorly or anteriorly from the superior portion 226 of the cam post core 218. The sleeve 220 may provide a complimentary fit shaped bore 236 that concentrically fits the superior portion 226 with the ridge 234 of the cam post core 218. This ridge 234 prevents any rotational movement of the sleeve 220. Any other means may be used to prevent rotational movement of the sleeve 220 around the cam post core 218. Again, the cam post core 218 and the sleeve 220 may be one piece instead of two pieces.

Figure 29:
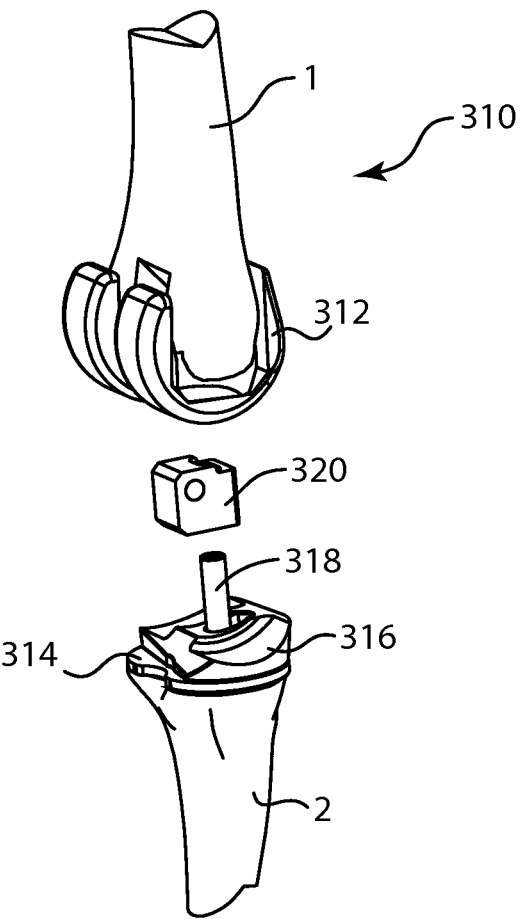
FIG. 29 illustrates an exploded perspective back view of an alternate embodiment of the prosthesis of FIG. 1 with a femur, a tibia, a femoral implant, a tibial insert, a tibial baseplate, a cam post and a hinge block which slides around the cam post.
Figure 29:
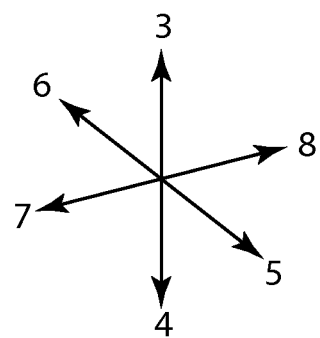
Figure 30:
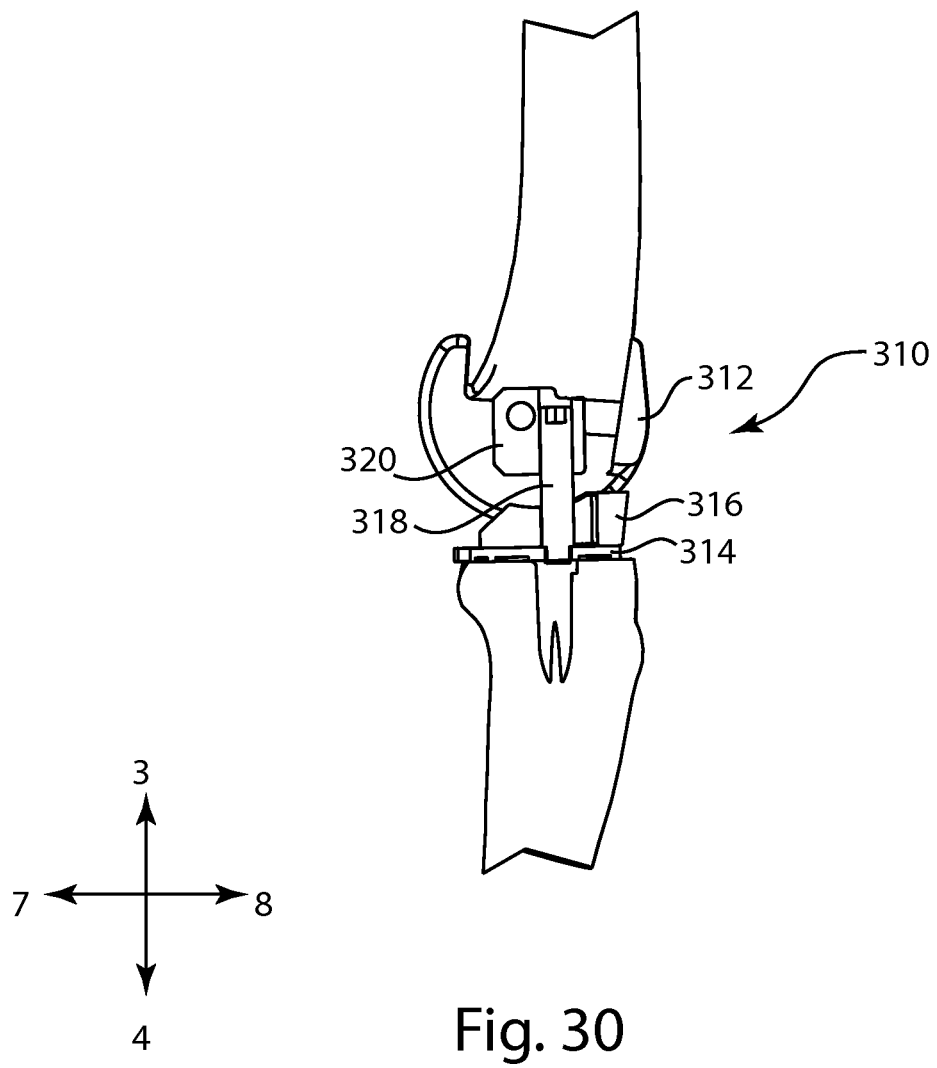
FIG. 30 illustrates a cross section side view of the prosthesis of FIG. 29 with the femoral implant secured to the femur, the femoral implant engaging the hinge block, the hinge block around the cam post, the condyles of the femoral implant articulating against the tibial insert, the tibial insert engaging the tibial baseplate and the tibial baseplate secured to the tibia.
Figure 31:
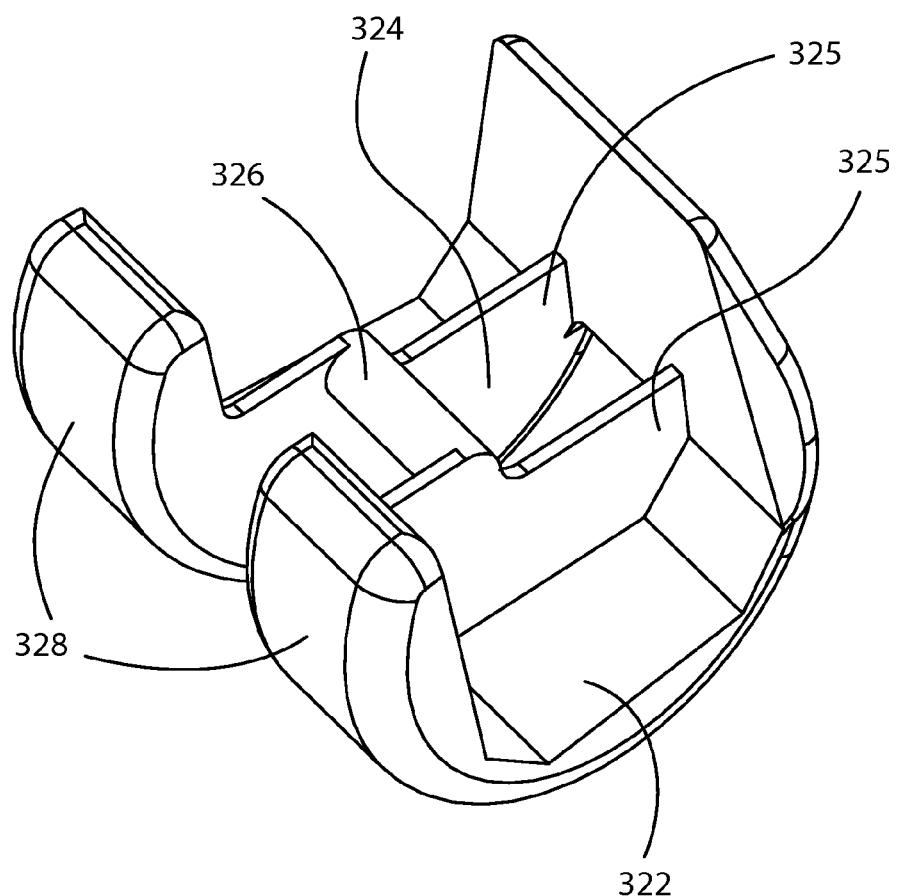
FIG. 31 illustrates a perspective back view of the femoral implant of FIG. 29 with condyles, an opening, opening walls to restrain varus/valgus movement, and an eccentric pin to pass through an opening in the hinge block to stabilize the hinge block (and the prosthesis) within the femoral implant.
Figure 31:
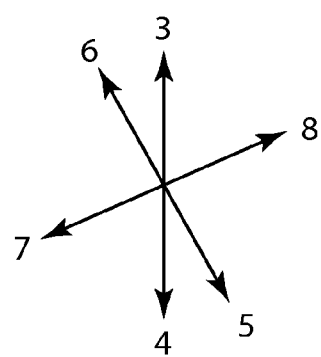

Referring to FIGS. 29 and 30, a further embodiment of a prosthetic knee 310 includes a femoral implant 312, a tibial baseplate 314, a tibial insert 316, a cam post 318 and a hinge block 320. The tibial baseplate 314 and the tibial insert may substantially mirror any of the previous embodiments recited herein with the medial rotational axis. Referring to FIG. 31, the femoral implant 312 is similar to the previous embodiments recited herein with a femur facing side 322, a femoral implant opening 324 and condyles 328 match the curvature of the specific tibial insert 316 chosen for the patient's mobility requirements. However, the femoral implant 312 also includes an eccentric pin 326 which is insertable into the hinge block 320 and opening walls 325 which engage the hinge block and help in preventing varus/valgus displacement and axial distraction, and provide greater medial/lateral stabilization (refer to FIG. 29).

Figure 32:
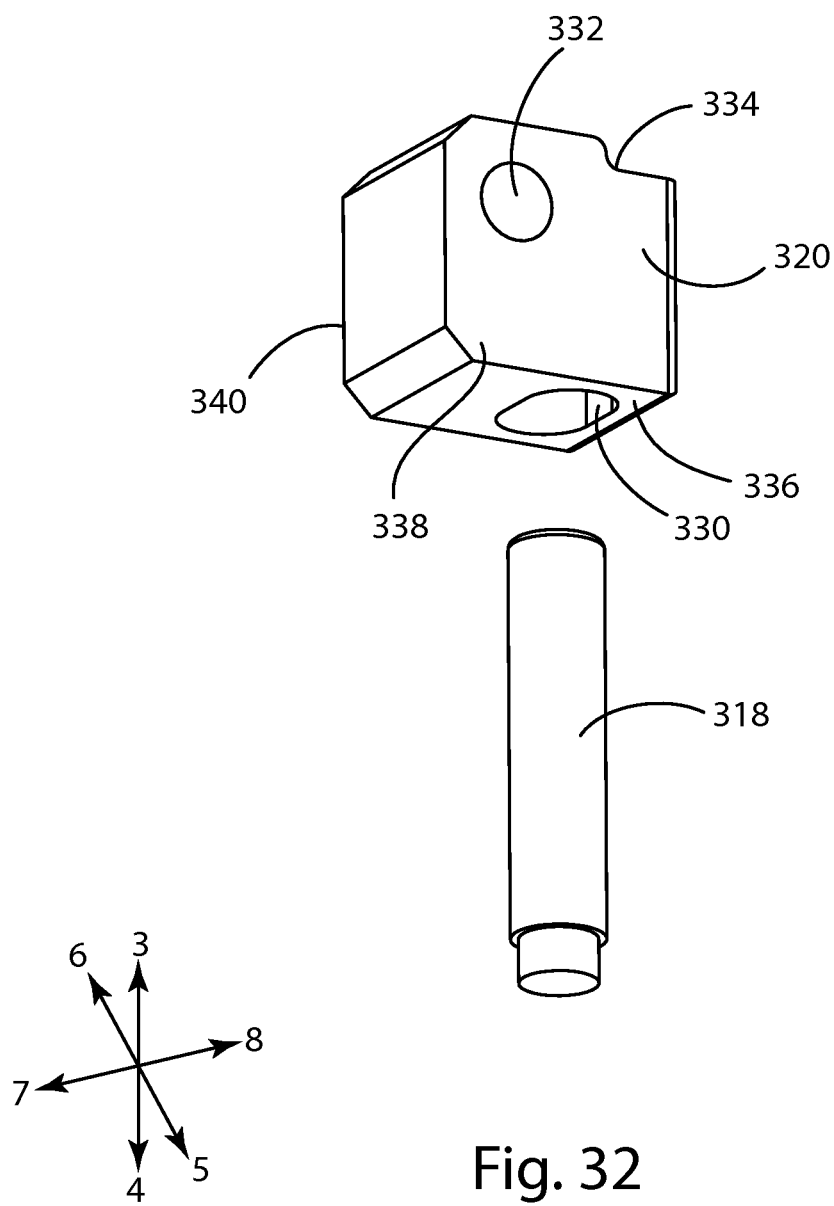
FIG. 32 illustrates a perspective view of the hinge block and cam post of FIG. 29 with the hinge block with a first bore running superiorly/inferiorly for engaging the cam post and a second bore running medial/laterally for engaging the eccentric pin of the femoral implant.

Referring to FIG. 32, the cam post 318 may be substantially circular in cross section with a Morse taper or similar taper toward the inferior end. The hinge block 320 may be substantially rectangular in cross section and may include a first bore 330 extending superiorly/inferiorly through the block from the superior end 334 to the inferior end 336. The first bore 330 is positioned toward the anterior end of the block 320 while the second bore is positioned near the posterior end and superior end 334. The first bore 330 is shaped to slidably receive the cam post 318. The hinge block may also include a second bore 332 extending laterally/medially through the block 320 from the medial end 338 to the lateral end 340. The second bore is positioned and shaped to receive the eccentric pin 326 of the femoral implant 312. The eccentric pin 326 and the opening walls 325 of the femoral implant 312 provide greater medial/lateral stabilization and prevent varus/valgus distraction. The two bores 330, 332 of the hinge block 320 do not intersect. This embodiment may be preferred for those patients that have insufficient, lax or absent medial or lateral stabilizing ligaments.

One method that may be used in placing the prosthetic knee 10 (any of the embodiments will be similar) is to attach the femoral implant 12 and tibial baseplate 14 first to the resected femur 1 and tibia 2 respectively. The order in which either of these is done is left to the preference of the surgeon. After each of the femoral implant 12 and tibial baseplate 14 is secured a trial tibial insert (not shown) with an attached trial cam post (not shown) is positioned on the tibial baseplate to determine the correct size of post and tibial insert to provide for the patients anatomy. The trial cam post is not rigidly connected to the trial insert and can move within the trial tibial insert channel. The trial tibial insert and cam post are removed and the tibial insert 316 is attached to the tibial baseplate through use of the tibial insert boss 24 and the tibial baseplate cavity 22. The knee is the hyper-flexed to allow the cam post 19 to be passed through the tibial insert channel 26 and secured to the tibial baseplate 14 in the tibial baseplate hole 30. The knee is then extended to position cam post 19 in the femoral implant opening 74.

While this method may be the preferred method, other methods may also be performed such as first attaching cam post 19 to the tibial baseplate 14 and then passing the tibial insert 16 over the cam post 19. The tibial insert 16 may then be secured to the tibial baseplate 14 and the knee extended to engage the cam post 19 with the femoral implant opening 74.

FIGS. 33-51 depict trial systems and guide assemblies which may be selectively utilized during implantation procedures to determine the optimally sized and shaped tibial insert for implantation. These systems may also provide a cutting guide for placement of cuts into the tibia for receiving anchoring features of a tibial baseplate, and may further provide guidance for positioning of the baseplate on the tibia. The trial systems disclosed herein may include components movable relative to one another, components which may be articulated in situ during the trialing process. This articulation may match the motion of the final prosthetic implant, providing an opportunity for the surgeon to observe the motion during the implantation process and thus select implants and positioning to more closely match the motion of the natural knee than would be provided by non-articulating trials.

Referring to FIG. 33A, a trial system 400 is shown assembled with tibial baseplate 14 and femoral implant 12. In the example shown, trial system 400 may be trialing, or substituting for, tibial insert 16 during the trialing process. Trial system 400, which may also be called an articular insert, comprises a tibial insert trial 402 and a cam post trial 404. In this embodiment the cam post trial 404 is securely captive to the tibial insert trial 402 and the tibial insert trial can slide on a guided pathway relative to the cam post trial 404.

Trial system 400 is shown alone in FIG. 33B. Tibial insert trial 402, which may also be referred to as an insert body, includes a first or superior side 406, a second or inferior side 408, with a periphery 410 extending between the first and second sides. A first boss 412 projects from the inferior side 408. Cam post trial 404, which may also be referred to as an insert post, may include a second boss 414 which projects inferiorly from the cam post trial 404. When the cam post trial 404 is operatively assembled with the tibial insert trial 402 as in FIGS. 33A and 33B, the second boss 414 also projects from the inferior side 408 of the tibial insert trial 402. In the embodiment shown, the first boss 412 is medially offset from the second boss 414. In other embodiments, the first boss 412 may be laterally offset from the second boss 414, and various anterior/posterior juxtapositions of the first and second bosses are also contemplated within the scope of the invention.

The knee and trial system shown are a left knee and left trial system. It is understood that any of the trials and implants disclosed herein may be shaped and configured for a left knee, and/or a mirror image trial or implant can be shaped and configured for a right knee. The trial systems disclosed herein may be permanently marked with information such as trial dimensions (medial/lateral and/or anterior/posterior), trial height or thickness, left/right, selected coloring, and/or notifications that the system is a trial and should not be implanted.

Figure 34A:
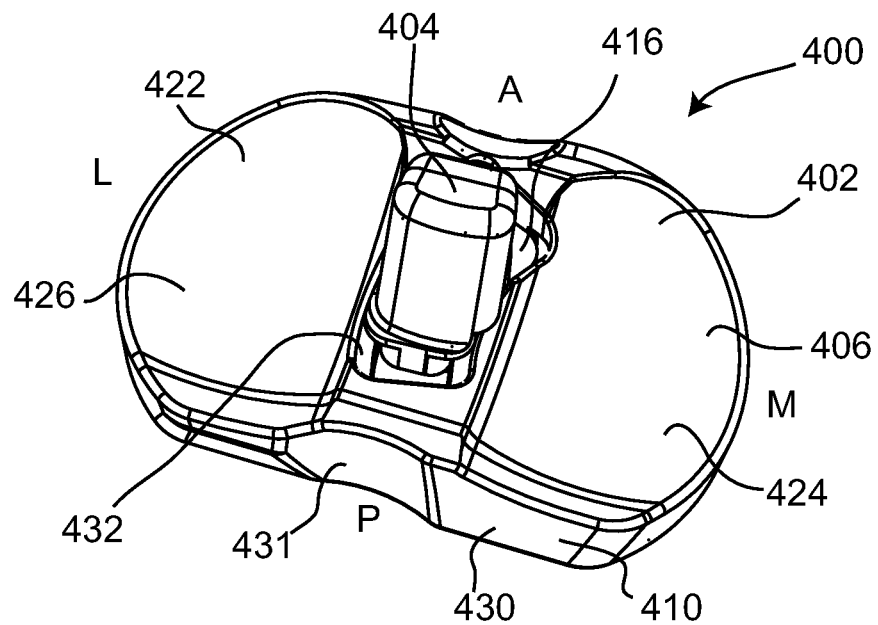
FIG. 34A is a postero-superior perspective view of the trial system of FIG. 33A.
Figure 34B:
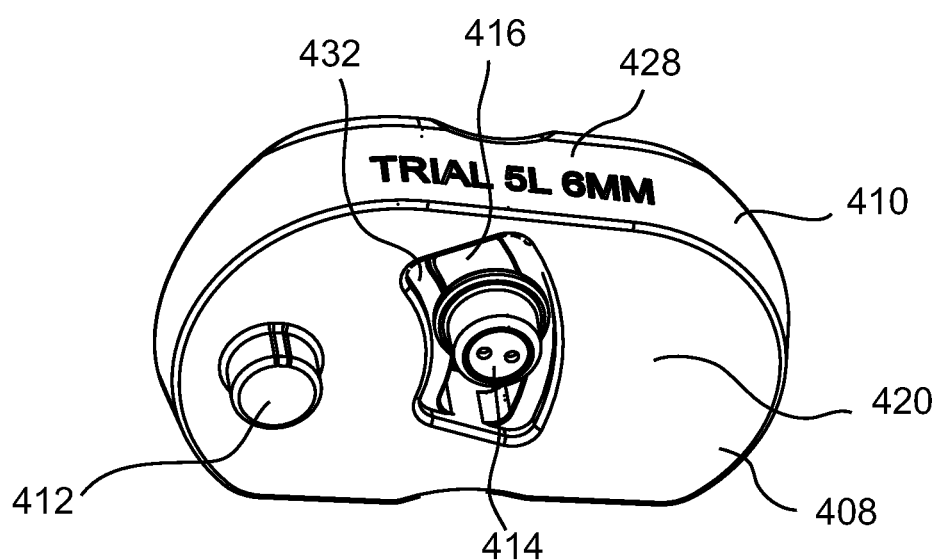
FIG. 34B is an antero-inferior perspective view of the trial system of FIG. 33A.

Superior and inferior views of the trial system 400 are shown in FIGS. 34A and 34B. Tibial insert trial 402 may be ovoid in footprint, to match a resected proximal tibia. The peripheral footprint of the tibial insert trial 402 may match that of the implant baseplate it is intended to be assembled with; alternately, the footprint may be smaller or larger than the baseplate. The tibial trial insert 402 may match tibial insert 16 in dimensions, shaping and features. An aperture, or insert trial channel 416 extends through the body of the insert 402 in communication with the superior and inferior sides 406, 408.

The inferior side 408 of tibial insert trial 402 may include a planar first insert articular surface 420. When assembled with a baseplate such as tibial baseplate 14 as in FIG. 33A or trial baseplates as disclosed below, the first insert articular surface may face and slide along an independent articular surface formed on the tibial baseplate 14 or trial baseplate. The superior side 406 of tibial insert trial 402 may include a second insert articular surface 422, which may be shaped to form an articulating joint with another independent articular surface. For example, as also seen in FIG. 33A the second insert articular surface 422 articulates with the condylar articular surfaces of femoral implant 412. Second insert articular surface 422 may further comprise a medial articular surface 424 and a lateral articular surface 426, located on opposing sides of the insert trial channel 416. The medial articular surface 424 may be positioned medial to the insert trial channel 416 and extend from the insert trial channel 416 to the insert trial periphery 410. The lateral articular surface 426 may be positioned lateral to the insert trial channel 416 and extend to the insert trial periphery 410. The articular surfaces 424, 426 are shaped and curved to align with the femoral implant 12 when the femoral implant and trial system 400 are operatively assembled as in, for example, FIG. 33A.

The insert trial 402 may vary in height or thickness along any of its directions. For example, as seen in FIGS. 34A and 34B, an anterior-facing periphery 428 of the insert 402 may be taller than a posterior-facing periphery 430. Similar height variation may occur medial-laterally. A notch 431 may be formed in the posterior-facing periphery 430 to allow room for the PCL.

The insert trial channel 416 may be arc-shaped and may be centrally located in the tibial insert trial 402, extending generally anterior-posteriorly. It is sized and shaped to slidably receive the cam post trial 404. The insert trial channel 416 is large enough and shaped to allow some arc-like rotation of the tibial insert trial 402 relative to the cam post trial 404. The interaction of the cam post trial 404 with anterior and posterior ends of the channel 416 may form stops to limit relative motion between the cam post trial 404 and the tibial insert trial 402. A track feature may be formed along at least a portion of the insert trial channel 416, and may comprises a tab, protuberance, rail, lip, groove or other guiding feature known in the art. In the embodiment shown, track feature 432 cooperates with the cam post trial 404 to both retain the cam post trial 404 in the insert trial channel 416 and guide translation of the tibial insert trial 402 relative to the cam post trial 404. Specifically, the tibial insert trial 402 may translate relative to the cam post trial 404 along an arc as limited by the insert trial channel 416. The motion of either of the two components 402, 404 is relative to one another, thus, cam post trial 404 may translate relative to tibial insert trial 402 along an arc-shaped pathway defined by the insert trial channel 416. It is appreciated that the insert trial channel 416 may comprise a shape other than an arc; in some embodiments the channel 416 may be straight and oriented directly anteriorly-posteriorly; in some embodiments the channel 416 may be straight and oriented at an angle relative to the anterior-posterior direction; in some embodiments the channel 416 may be arced in a different direction and/or have a different radius; and/or in some embodiments the channel 416 and track 432 may change elevation between the anterior and posterior ends.

Figure 35:
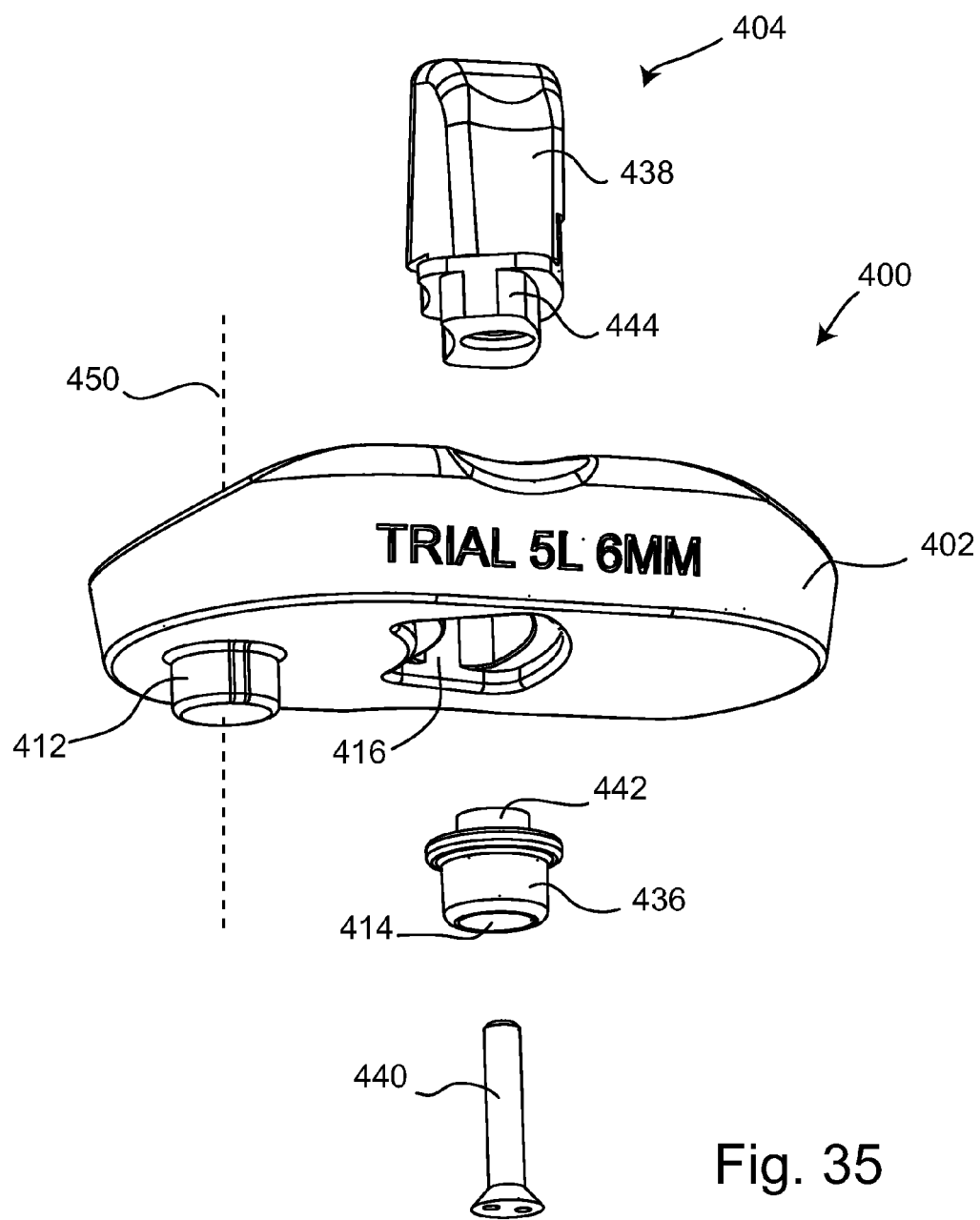
FIG. 35 is an anterior exploded view of the trial system of FIG. 33A.

Referring to FIG. 35, an exploded view of trial system 400 is shown. In this embodiment, cam post trial 404 comprises a retainer or first post portion 436, a second post portion 438, and a fastener 440 which lockably fastens the first and second post portions 436, 438 together. When operatively assembled as in FIG. 33B, a first connection feature 442 of the first post portion 436 is received in channel 416, the track feature 432 preventing the first post portion 436 from passing entirely through the channel. A second connection feature 444 of the second post portion 438 is received in the channel 416 from the opposite direction as the first post portion. The first and second connection features 442, 444 engage with one another to form first and second post portions 436, 438 into a unitary post. Fastener 440 engages both the first and second connection features 442, 444 to lock the first and second post portions 436, 438 in what can be a rigid engagement. Because the track feature 432 is positioned between the first and second post portion 438, fastening the first and second post portions together also makes the cam post trial 404 captive to the tibial trial insert 402. Although the first and second post portions 436, 438 are locked together, sufficient clearance remains between the first and second post portions 436, 438 and the track feature 432 to allow free movement of the tibial insert trial 402 relative to the cam post trial 404, constrained and guided by the channel 416. This movement may take the form of rotational translation between the tibial insert trial 402 and the cam post trial 404.

The cam post trial 404 may be shaped like cam post 19 and may interact with femoral implant 12 in the same manner as described for cam post 19. In other embodiments, the cam post trial may be shaped like any one of the other cam posts (118, 219, 318, as examples) disclosed herein.

Figure 36:
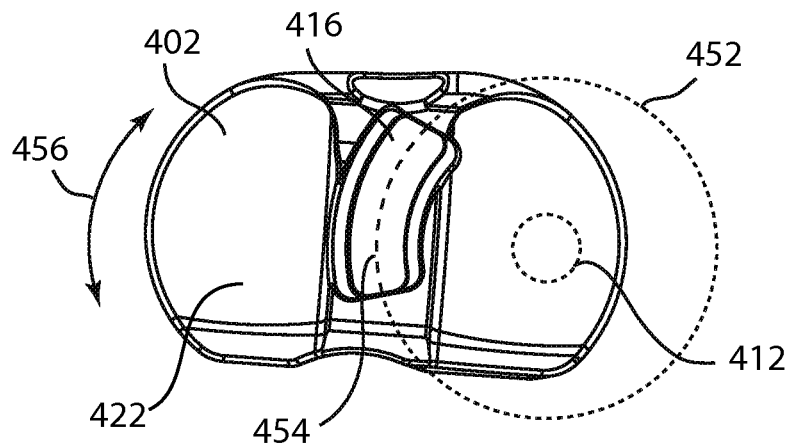
FIG. 36 is an inferior view of the tibial insert trial of FIG. 33B, and an arc illustrating a rotational pathway of the cam post trial.
Figure 37A:
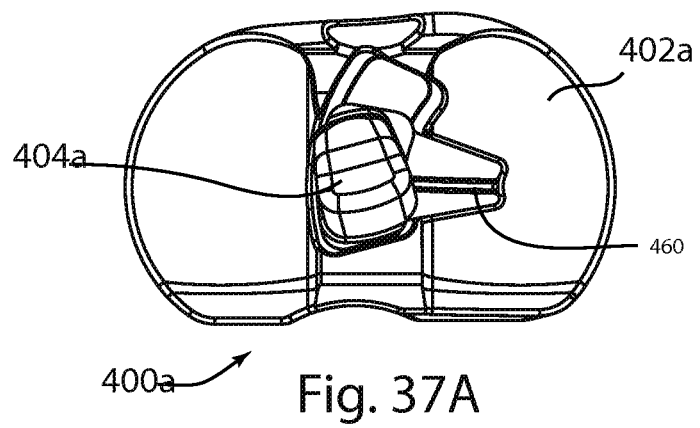
FIG. 37A is a superior view of an alternate embodiment of a tibial insert trial with a flexible element, the trial in a knee extended position.
Figure 37B:
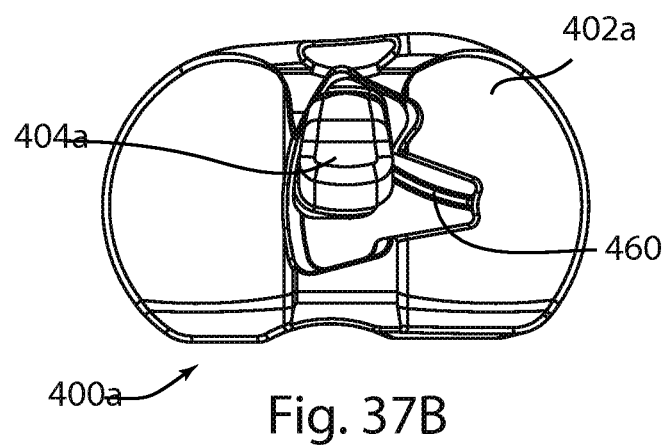
FIG. 37B is the trial of FIG. 37A with the trial in a knee flexed position.

For trial system 400, rotational translation between tibial insert trial 402 and cam post trial 404 occurs about an axis 450 extending perpendicularly through first boss 412, along a pathway defined by the channel 416. Referring to FIG. 36, a dashed small circle shows the location of first boss 412 on tibial insert trial 402. A dashed larger circle 452 depicts a circle formed which has as its center the center of first boss 412, with a radius that causes it to pass along the center of channel 416. A pathway 454 is defined by the curvature of channel 416, and is seen to be an arc of circle 452, the arc approximately 60 degrees. When operatively assembled, tibial trial insert 402 can rotate relative to cam post trial 404 along the pathway 454 bidirectionally, as shown by indicator arrow 456. In some embodiments, the arced pathway defines an arc having a range of 0 degrees to 180 degrees. In some embodiments, the arced pathway defines an arc having a range of 0 degrees to 90 degrees. In some embodiments, the arced pathway defines an arc having a range of 0 degrees to 45 degrees.

In one method of use, trial system 400 may be used with tibial baseplate 14 and femoral implant 12 to temporarily emulate insertion of a tibial articular insert with the baseplate and femoral components. The temporary emulation may allow selection of a properly sized and shaped tibial articular insert for the patient's specific anatomy, and may allow the surgeon to determine if physiologically correct flexion and extension of the joint can occur with the selection of the particular tibial articular insert. For example, the tibial insert trialing procedure can help the practitioner determine the correct thickness of the finally implanted tibial insert. Also, the trialing procedure allows allow the surgeon to move the prosthetic knee assembly, as seen in FIG. 33A, throughout its range of motion to confirm that the knee articulates without excessive looseness or binding. A series or kit of tibial systems 400 and tibial articular inserts and/or cam posts of varying dimensions may be provided, to allow temporary insertion and removal of various trials until the properly sized and shaped trial is determined. Then a tibial articular insert and cam post, for example tibial insert 16 and cam post 18, can be selected which matches the properly sized and shaped trial, and implanted.

Figure 38:
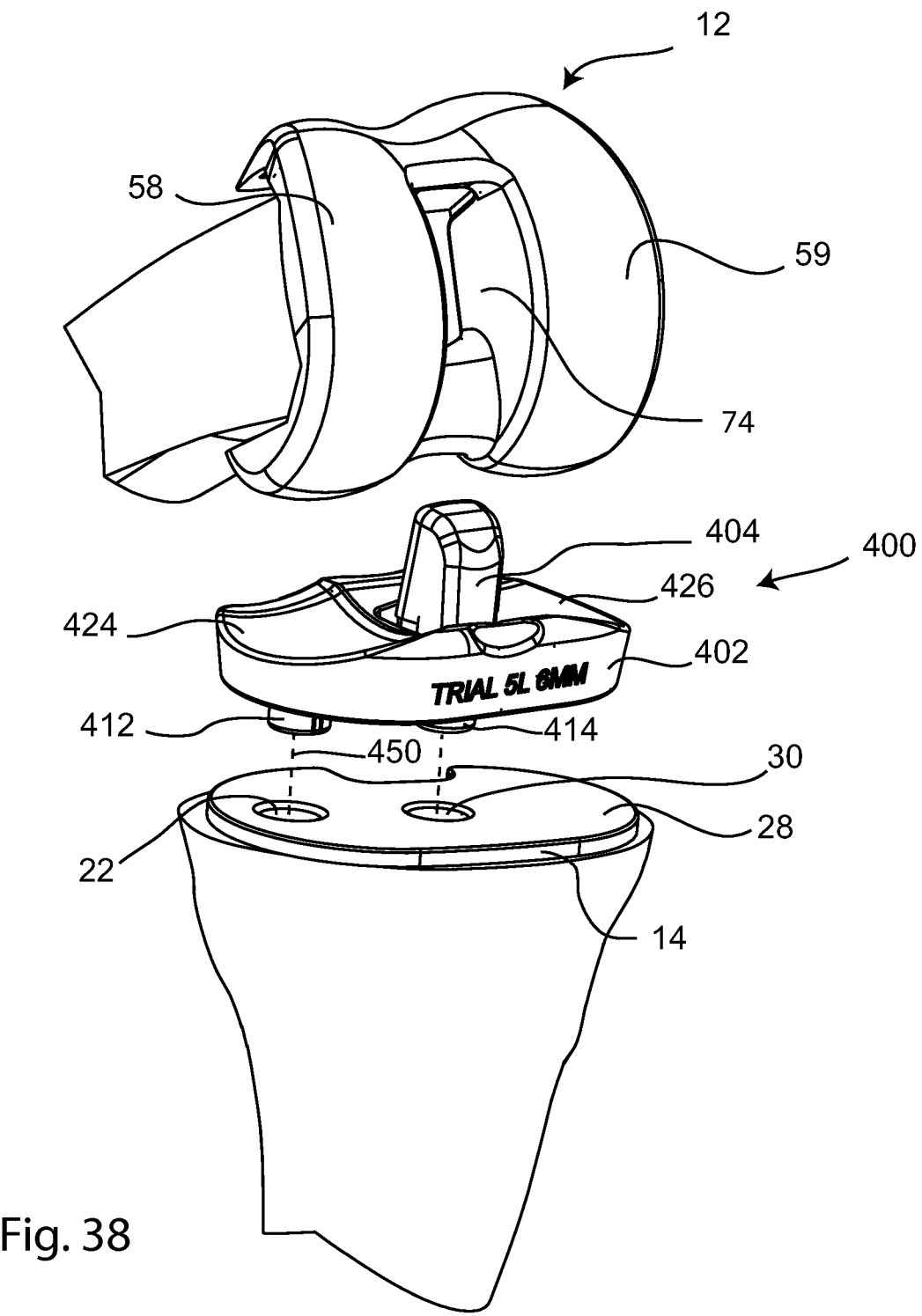
FIG. 38 is a perspective exploded view of the knee joint, femoral and tibial components, and trial system of FIG. 33A.

During the trialing procedure, the baseplate 14 and femoral implant 12 may be implanted as described herein. Referring to FIG. 38, trial system 400 comprising tibial insert trial 402 and cam post trial 404 may be mounted into direct engagement with baseplate 14. First boss 412 fits into cavity 22, and second boss 414 fits into hole 30. First boss 412 is sized so that when it is engaged in cavity 22, there is sufficient room between the boss and the cavity walls to allow rotation, or pivoting, of the tibial insert trial relative to the baseplate 14 about axis 450. It is appreciated that in this embodiment axis 450 is coaxial with rotation axis 23 shown in FIGS. 4 and 5. Second boss 414 may fit more snugly into hole 30, so that cam post trial 404 does not move unintentionally relative to baseplate 14 during the trialing procedure.

After trial system 400 is mounted onto the baseplate 14, the femoral implant 12 is placed in engagement with the trial system, with cam post trial 404 extending through opening 74, and condyles 58, 59 abutting articular surfaces 424, 426. The joint may then be urged through flexion and extension, during which the tibial trial insert 402 may pivot, or rotate about axis 450. The first insert articular surface 420 translates along the superior surface 28 of the baseplate 14. The cam post trial 404 provides anterior and posterior rotational stops for the tibial insert trial 402. In an alternate method of use, the cam post trial 404 may first be engaged with femoral implant 12, then the trial system 400 is mounted onto the baseplate 14. As set forth previously, after placing the trial system 400 into engagement with the femoral implant 12 and baseplate 14, the joint may be flexed and extended to determine if the motion provided by the tibial trial insert matches the natural motion of the joint. If so, the trial system 400 may be removed and an articular insert and cam post matching those of the trial may implanted. If not, trial systems 400 of other dimensions may be substituted until the correct size and shape is selected which most closely matches the natural motion of the knee, or which most closely matches the motion preferred by the practitioner. The tibial insert and cam post matching those of the finally selected trial may be implanted.

In alternative embodiments, the cam post trial 404 may be attached to the tibial insert trial 402 with or without use of a separate fastener by an interlocking mechanism, press fit, snap fit, adhesive bonding, ultrasonic welding or other methods of attachment known in the art. In some embodiments, a flexing element may connect the cam post trial and the tibial insert trial, the flexing element comprising a thin piece of metal or metal alloy, plastic, silicone or other rubber, or other flexible biocompatible material. In an alternative embodiment of a tibial insert trial 400a shown in FIGS. 37A and 37B, the cam post trial 404a may be connected to insert trial 402a by a flexing element 460 that flexes to allow the cam post to rotate relative to the tibial insert. Cam post trial 404a, insert trial 402a and flexing element 460 may be formed as a single piece. Cam post trial 404a, insert trial 402a and flexing element 460 may formed of the same, or differing constituent materials.

In alternative embodiments, the thickness, or height of the tibial insert trial 402 between the superior and inferior sides may be adjustable, as may the height of the cam post trial 404. In alternative embodiments, the range of motion between the cam post trial and the tibial insert trial may be adjustable, for example, by providing an adjustable length channel 416. In an alternative embodiment, the tibial insert trial may be symmetric across its coronal midline (a medial-lateral plane extending across the center of the insert), allowing the same tibial trial assembly to be used on either the left or right knee, simply by rotating it 180 degrees.

Another trial system includes a temporary baseplate trial and a cutting guide, the cutting guide adjustable relative to the baseplate along one or more directions. The trial system may be using during an implantation procedure to determined optimal placement of an implanted tibial baseplate. The trial system may further include a tibial insert trial which may be translatable relative to the baseplate trial and cutting guide, and provide guidance for selection of an implantable tibial insert. The adjustability of the trial may allow the surgeon to more accurately position the final implant components. This more accurate final position will lead to more natural motion of the knee joint in use, and less stress on the mating interface between the prosthetic components and the resected bone(s) to which these components are mounted. Ultimately, this may result in better implant performance and longer implant life.

Figure 39:
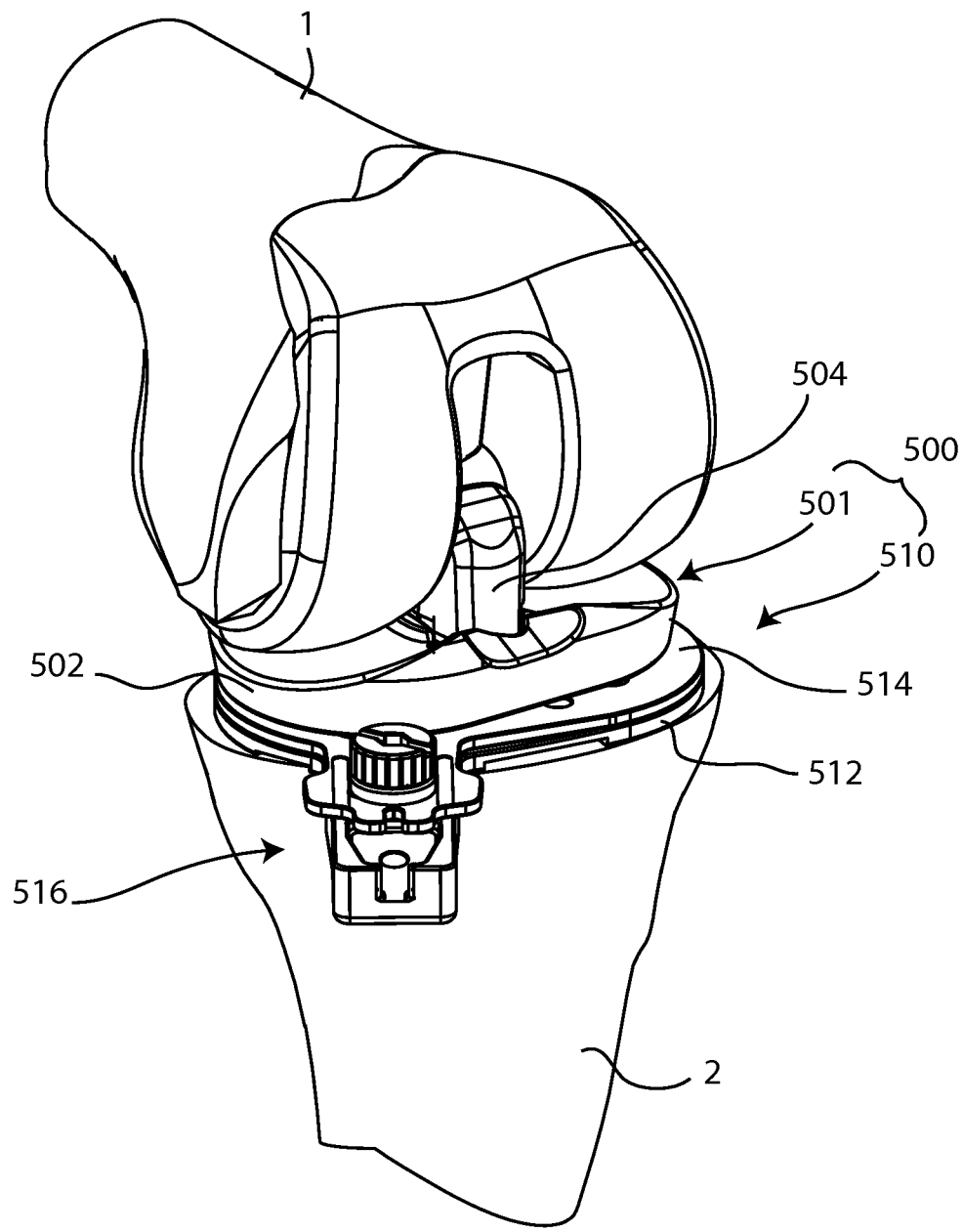
FIG. 39 is a perspective view of a knee joint in a flexed position, with femoral component and a trial system including an articulating trial insert and a rotationally adjustable guide assembly.

Referring to FIG. 39, trial system 500 comprises a guide assembly 510 and a tibial insert assembly 501. Tibial insert assembly 501 comprises a tibial insert trial 502 and cam post trial 504, which may be the same as tibial insert trial 402 and cam post trial 404. Guide assembly 510 includes a tibial baseplate trial 512 and a guide plate trial 514, and may further include an adjustment mechanism 516, which may be called a rotational adjustment mechanism. Tibial baseplate trial 512 may be temporarily affixed to a resected proximal tibia. Guide plate trial 514 may be attached to the tibial baseplate trial 512 to form guide assembly 510, and the guide plate trial 514 rotated relative to the tibial baseplate trial 512 while attached. Tibial insert assembly 501 may be mounted on the guide assembly 510 and the tibial insert trial 502 rotated relative to the guide assembly independently of rotation of the guide plate trial to the baseplate trial.

Figure 40A:
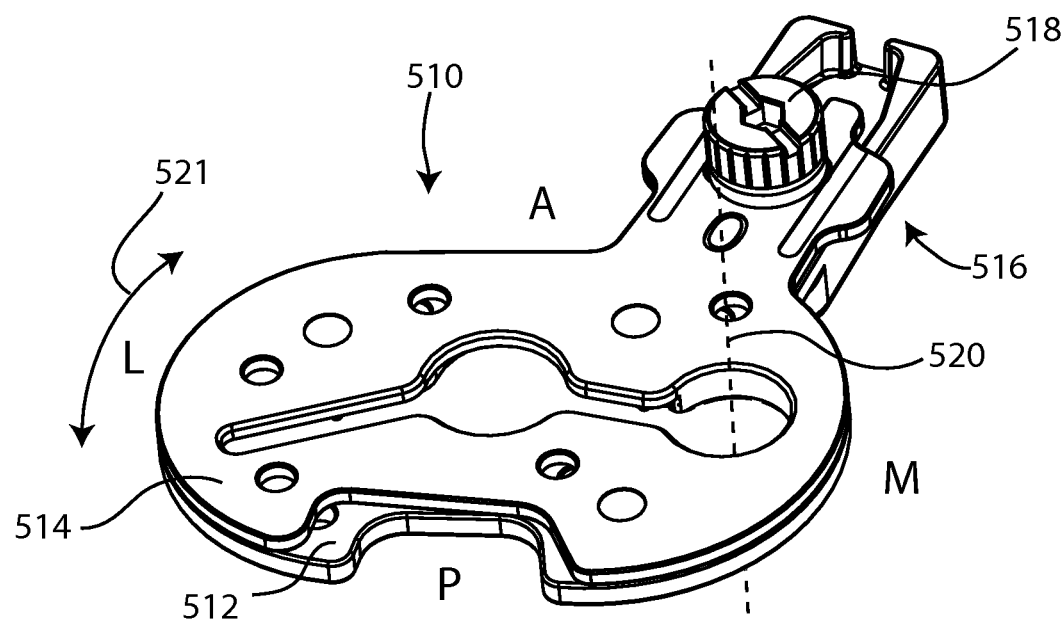
FIG. 40A is a postero-superior view of the guide assembly of FIG. 39.

Referring to FIG. 40A, a posterior perspective view of guide assembly 510 is shown. As operatively assembled, guide plate trial 514 lies against tibial baseplate trial 512, and a screw 518 fastens the plates 512, 514 together at a selected juxtaposition. When screw 518 is loosened, guide plate trial 514 may rotate relative to tibial baseplate trial 512 about a rotation axis 520 and as shown by indicator arrow 521. It is appreciated that in other embodiments, another fastener known in the art may adjustably fasten plates 512 and 514 together. Such fasteners may include screws, bolts, nails, brads, rivets, sutures, wires, cords, elastic elements, and clamps, among others. Pegs 522 protruding from an inferior side of tibial baseplate trial 512 may be used to temporarily affix the guide assembly 510 to a resected bone surface.

Rotation axis 520 is medially located relative to the approximate center of guide plate trial 514 to permit use of the guide assembly with a medially pivoting or rotating tibial insert trial such as trial 502, in preparation for a medially rotating tibial insert such as insert 16, 116 or 216. Rotation axis 520 is located medially of the sagittal midline of guide plate trial 514. When guide assembly 510 is mounted to a resected tibia as in FIG. 39, the rotation axis 520 is medial to the sagittal midline of the resected tibia. The rotation axis may be positioned closer to the medial periphery of the guide plate trial 514 than to the sagittal midline. In varying embodiments, the rotation axis 520 may be located on, anterior to, or posterior to, the coronal midline of the resected tibia and/or guide plate trial 514. In still other embodiments the rotation axis may be centrally located on the resected tibia and/or guide plate trial.

Figure 40B:
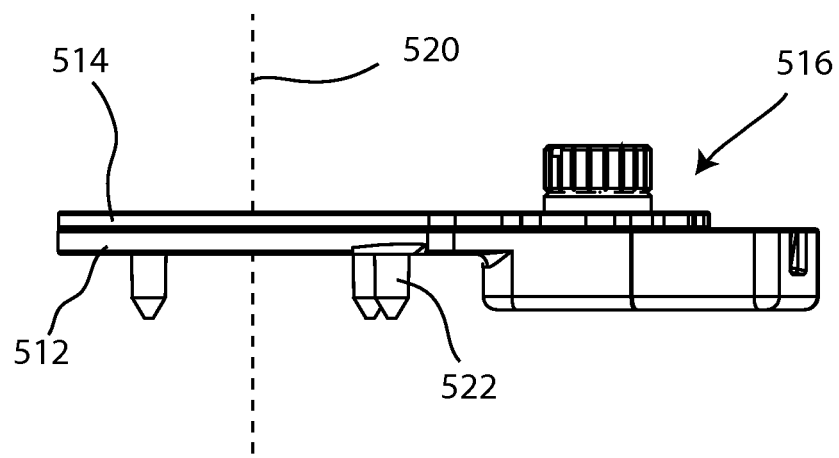
FIG. 40B is a side view of the guide assembly of FIG. 39B.
Figure 41:
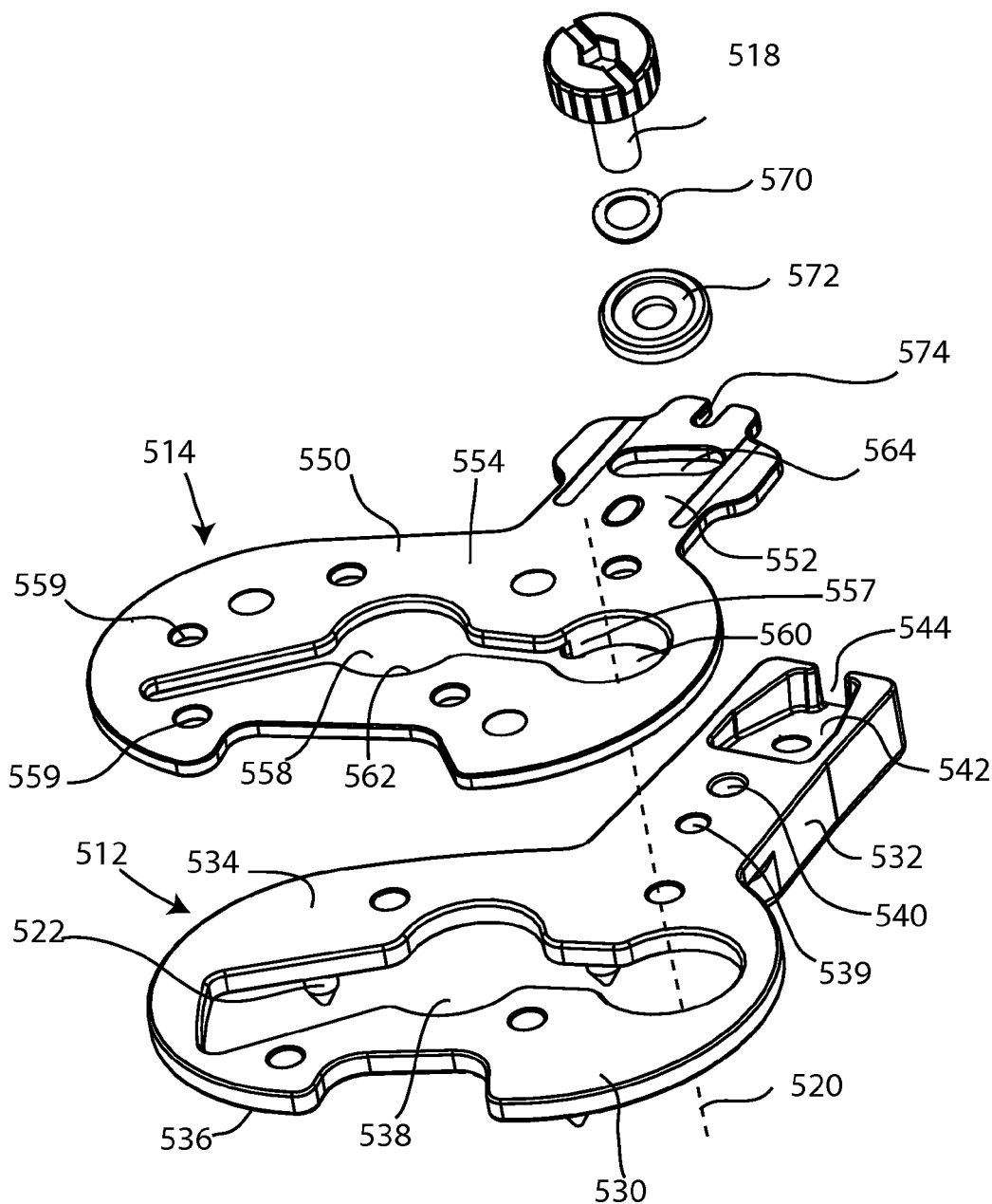
FIG. 41 is an exploded superior view of the guide assembly of FIG. 39, the guide assembly including a baseplate, a guide plate, and an adjustment mechanism that controls relative rotation between the guide plate and the baseplate.
Figure 42:
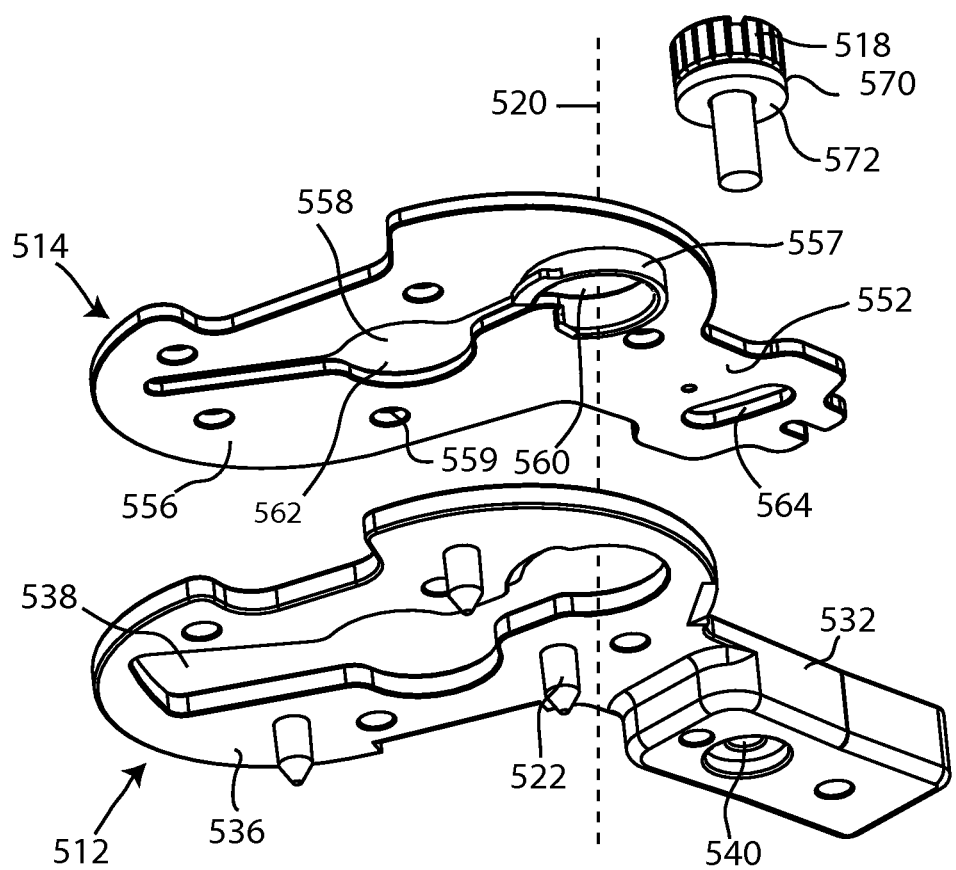
FIG. 42 is an exploded inferior view of the guide assembly of FIG. 39.

FIG. 40B shows a side view of the guide assembly. FIG. 41 shows guide assembly 510 in a posterior, top-down exploded view, while FIG. 42 shows guide assembly 510 in a posterior, bottom-up exploded view. Tibial baseplate trial 512 includes an ovoid baseplate body 530, from which a baseplate extension 532 extends anteriorly. The tibial baseplate trial includes a superior side 534, and an inferior side 536 from which the pegs 522 protrude. A baseplate aperture 538 perforates the baseplate body 530, extending between the superior side 534 and the inferior side 536. A plurality of additional holes 539 may also extend through the tibial baseplate trial 512. Baseplate extension 532 includes a passage 540 through which screw 518 may be threaded to connect the plates 512, 514. Baseplate extension 532 may further include a cavity 542 having an access portal 544, which may allow access to the cavity and the adjustment mechanism 516.

The guide plate trial 514 may be shaped similarly to the tibial baseplate trial 512, and has a guide plate body 550 from which a guide plate extension 552 extends. The guide plate trial includes a superior side 554, and an inferior side 556. A guide plate aperture 558 perforates the guide plate body 550, extending between the superior side 554 and the inferior side 556. The guide plate aperture 558 may be similarly shaped to the baseplate aperture 538, but the baseplate aperture 538 is larger in most dimensions so that when the guide plate trial 514 is operatively assembled with the baseplate trial 512, clear passage may be obtained through both apertures regardless of the rotational juxtaposition of the plates 512, 514. Guide plate aperture 558 may include a first port 560 and a second port 562, which may be shaped to receive first and second bosses formed on tibial insert trial 502. A collar 557 may be formed around the first port 560 of guide plate aperture 558. When guide plate 514 is positioned in an overlapping arrangement with baseplate 512, collar 557 may mate with a portion of baseplate aperture 538 to directly connect guide plate 514 to baseplate 512 while allowing rotation of guide plate 514 relative to baseplate 512. A plurality of additional holes 559 may also extend through the guide plate trial 514.

In the context of this disclosure, overlapping refers to a juxtapositional arrangement in which one plate is positioned to lay directly over the other plate, with a majority of one plate overlaid on a majority of the other. This overlapping arrangement can be seen in at least FIGS. 39, 43, and 44, in which guide plate 514 and baseplate 512 are arranged such that the plates are in planes parallel to one another, with guide plate 514 overlaying baseplate 512. Overlapping does not refer to a tangential arrangement in which, for example, one plate is turned 90 degrees relative to the other such that only a narrow edge of one plate touches the broadly planar surface of the other.

Guide plate extension 552 includes a slot 564 which receives screw 518 to adjustably fasten guide plate trial 514 to baseplate trial 512. Slot 564 is arc-shaped and positioned to guide rotation of guide plate trial 514 to baseplate trial 512 about axis 520 while the guide plate trial 514 is connected to the baseplate trial 512. Adjustment mechanism 516 may include screw 518 and guide plate extension 552, with slot 564. When screw 518 is loosened, but not removed from the guide assembly, guide plate extension 552 can be moved to translate slot 564 relative to screw 518 while screw 518 remains in passage 540. When screw 518 is tightened, the guide plate trial 514 and baseplate trial 512 are compressed toward one another and may be locked together. A wave washer 570 allows the practitioner to control the amount of friction in the rotation of plates 512 and 514; a flat washer 572 distributes the force from the screw 518 to plates 512 and 514. When screw 518 is fully tightened, guide plate 514 will not rotate with respect to baseplate 514. The flat washer 572 may be counterbored to prevent the wave washer 570 from being compressed past its recommended minimum thickness. Guide plate extension 552 may function as a lever to urge rotation of guide plate 512 relative to baseplate 514. A notch 574 or other feature may receive an instrument which exerts force on guide plate extension 552 to rotate guide plate 512. Alternatively, guide plate extension 552 may be manually shifted to rotate guide plate 514.

A ball plunger (not shown) may be mounted into a hole 539 on the baseplate extension 532 to contact the guide plate extension 552, providing a tactile indication to the practitioner when the guide plate trial 514 moves into or away from a midpoint position or another selected position. Indicia may also be located on at least one of the trial and guide plates to provide visual indication of the rotational juxtaposition of the plates.

Figure 43:
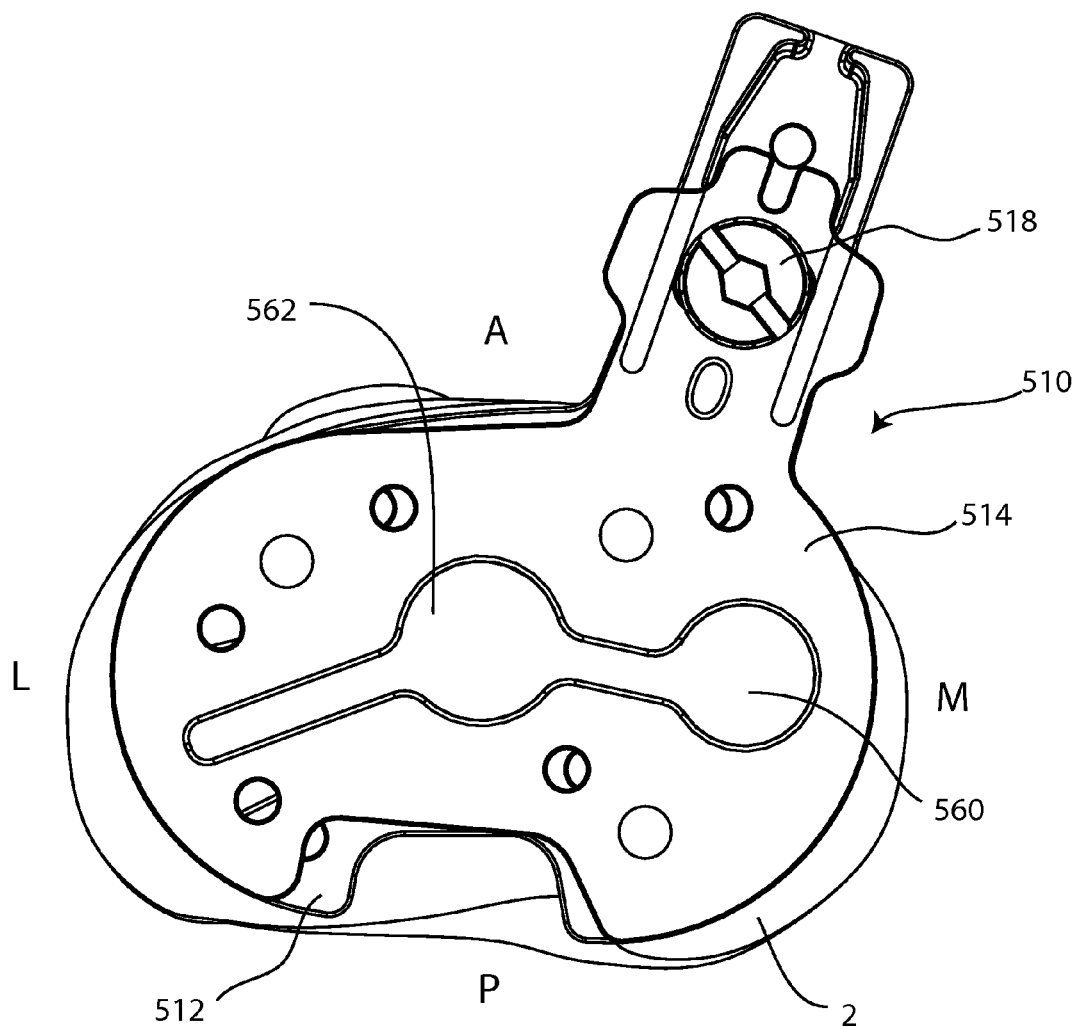
FIG. 43 is a superior view of the guide assembly of FIG. 39 mounted on a resected tibia.
Figure 44:
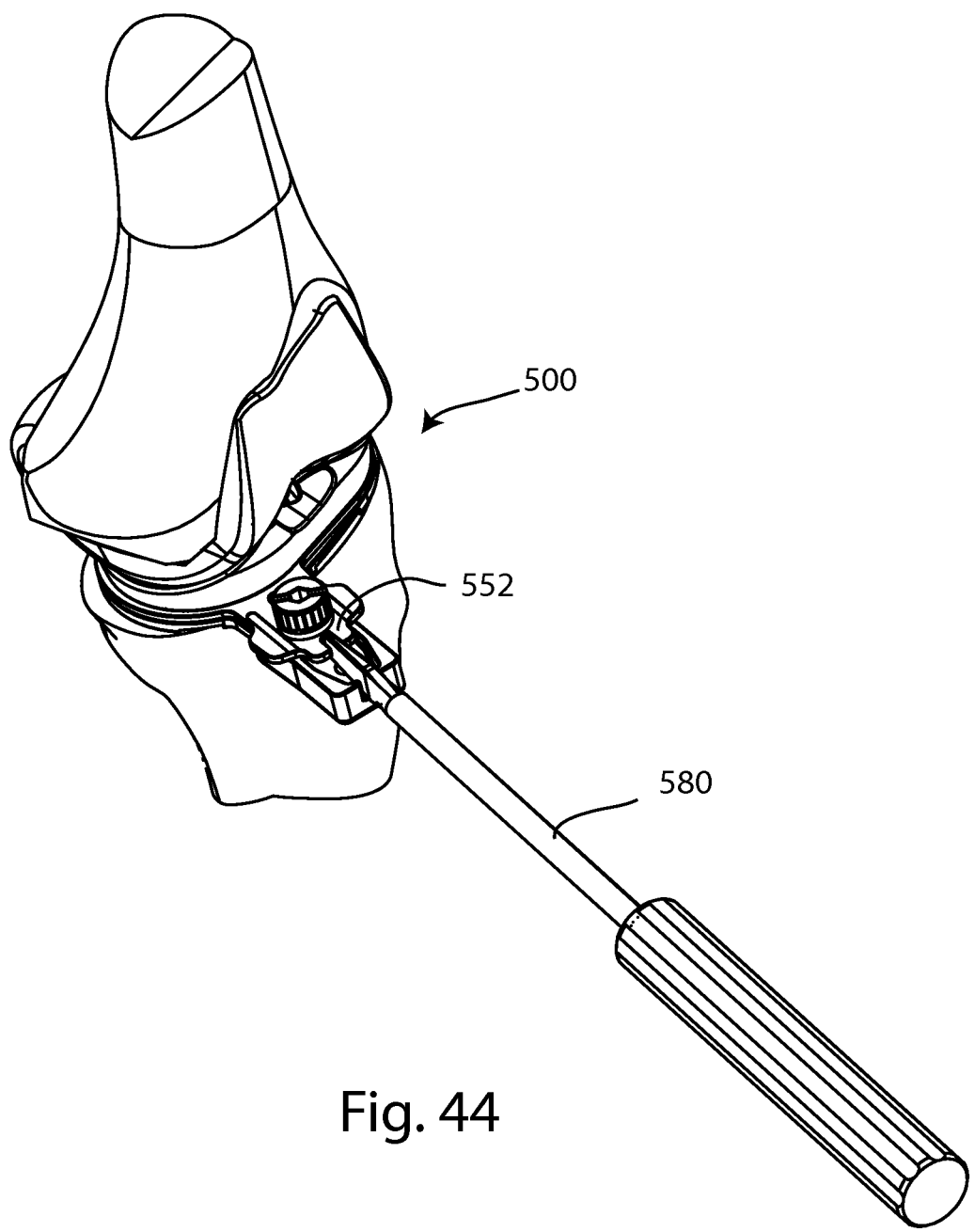
FIG. 44 is a perspective view of the knee joint, articulating trial insert and guide assembly of FIG. 39, showing adjustment of the relative rotation between the guide plate and the baseplate.
Figure 45:
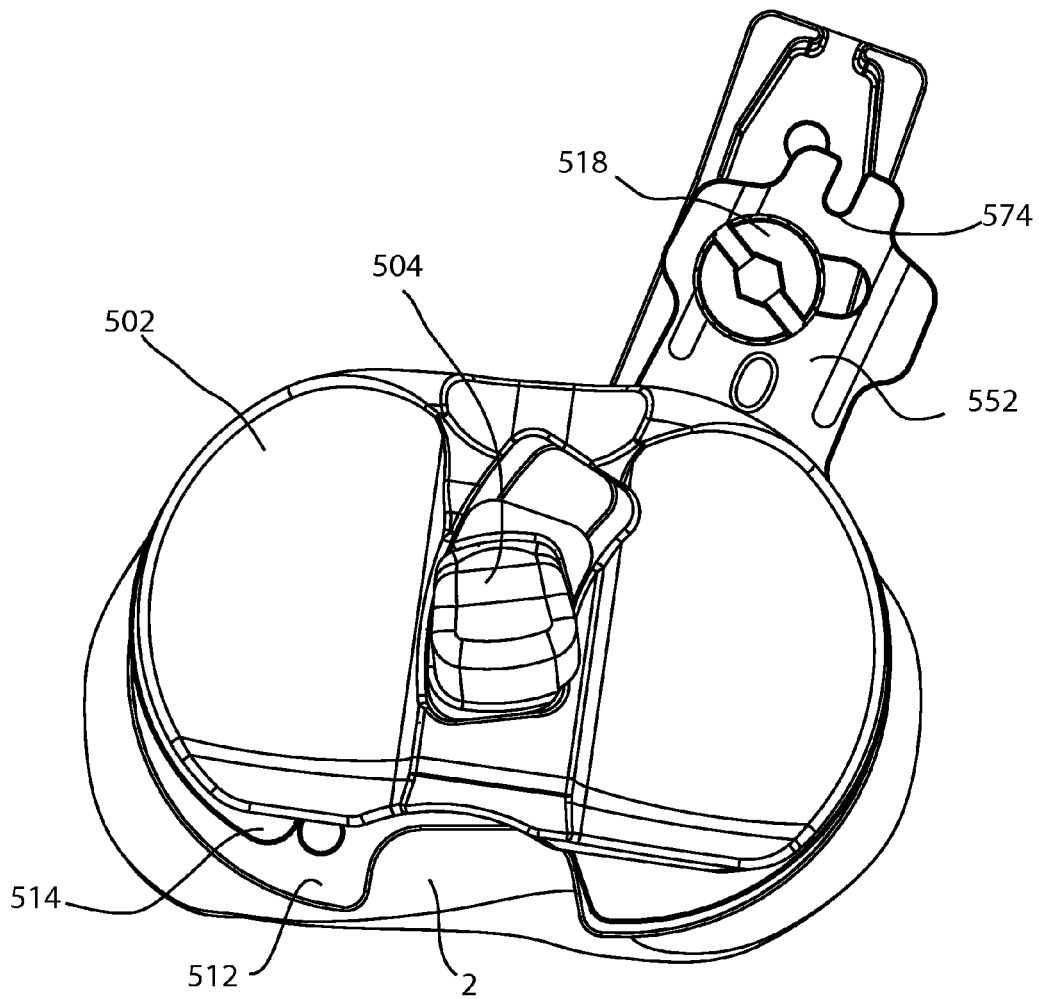
FIG. 45 is a superior view of the trial system and guide assembly of FIG. 39 mounted on a resected tibia, with the guide plate rotated medially relative to the baseplate and the articulating trial insert in a joint extended position.

In one method of use, the bone surfaces of the tibia and femur are first resected per normal implant procedures. With reference to FIGS. 39 and 43, the guide assembly 510 is prepared by placing the guide plate 514 in a central, or midpoint position relative to the baseplate 512. Screw 518 is tightened to lock the plates in the midpoint juxtaposition. The guide assembly 510 is mounted on the resected proximal tibia 2 with the baseplate 512 centered on the resected tibial surface. Pegs 522 may help secure the baseplate 512 to the resected tibial surface. A femoral component and trial tibial insert assembly 501 may then be installed as seen in FIG. 39, with a first boss of tibial insert trial 502 received in first port 560 and a second boss of cam post trial 504 received in second port 562, so that tibial insert trial 502 may rotate about rotation axis 520 relative to guide assembly 510. Locking screw 518 may then be loosened, and the knee flexed and then extended. With the knee extended, the surgeon can first confirm proper femoral contact with the trial tibial insert 501, and then rotate the guide plate 514 to place the trial cam post 504, which will move with second port 562, in a desired position. Rotation of guide plate 514 may be accomplished manually, and/or by inserting a tip of a screwdriver 580 or other instrument into notch 574 to lever guide plate extension 552, as seen in FIG. 44. Guide plate 514 may be rotated so that the trial cam post 504 is in the knee-extended position as shown in FIG. 45. In this position the cam post 504 may be at the posterior extreme of the arced pathway. With the guide plate 514 and the trial cam post 504 in the desired positions, locking screw 518 is then tightened to lock the plates 512, 514 in the selected juxtaposition, and the trial tibial insert assembly 501 removed. Locking screw 518 may be actuated manually or using screwdriver 580 or another instrument. Using the guide plate aperture 558 as a guide, drills and punches can then be used to cut the tibial bone for the final prosthetic tibial implant keel and fins, for example those seen on baseplate 14 in FIGS. 4 and 5. The trial system 500 may then be removed, and implantation of the prosthetic knee can proceed per standard techniques.

While directly connected to baseplate 512, guide plate 514 may be rotated within a twelve degree range, that is, from zero to six degrees in either direction from the midpoint configuration. FIG. 45 shows guide plate 514 rotated medially, or clockwise; in another embodiment of use it may be rotated laterally, or counter-clockwise. In other embodiments, the guide plate may be rotated relative to the baseplate within a range of up to 180 degrees in either direction from the midpoint configuration.

This ability to rotationally adjust the trial device is particularly important when implanting prosthetic knee implants of a mobile bearing design. In these designs, there is relative motion between the tibial insert and tibial baseplate. This relative motion allows prosthetic knee motion which more closely matches the motion of the normal knee. For best kinematic performance of the mobile bearing design, the initial rotational between tibial and femoral components should be accurately controlled, to within an estimated ±3 degrees.

Figure 46:
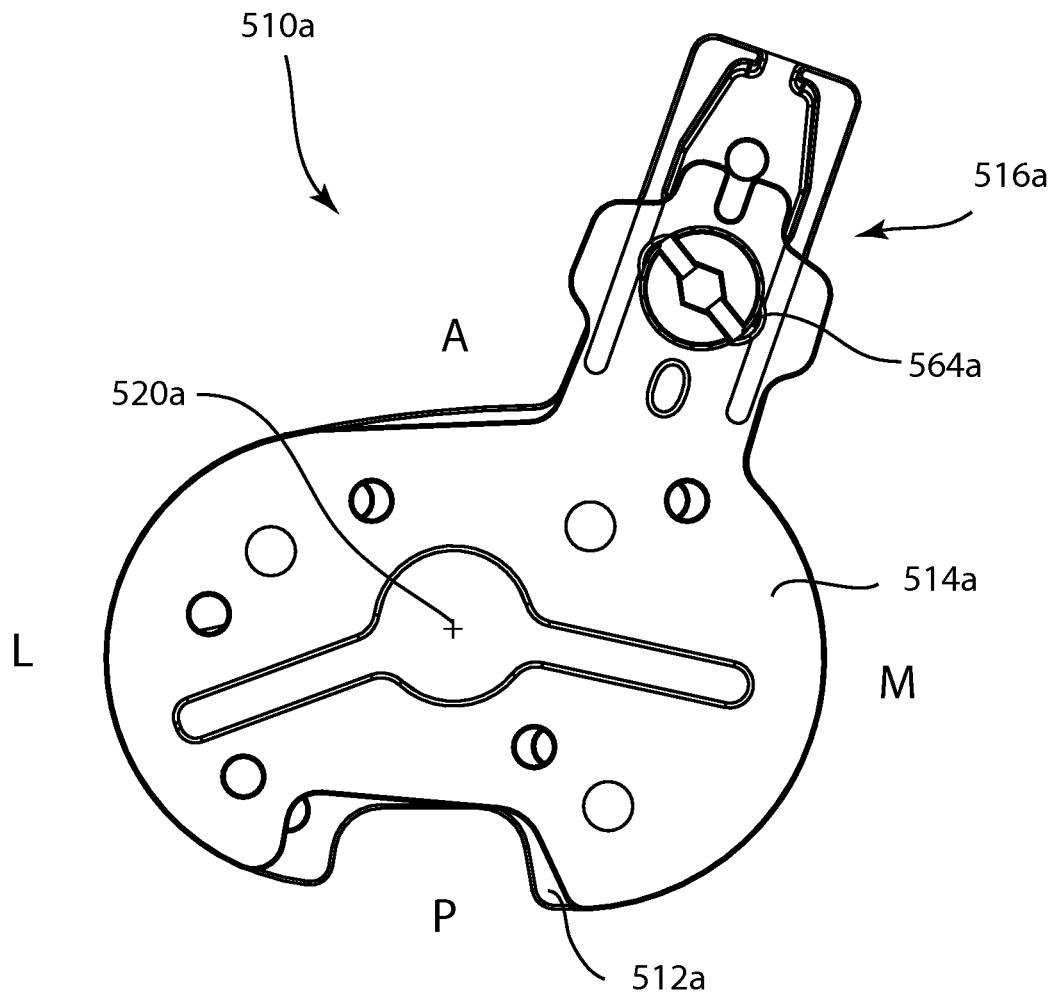
FIG. 46 is a superior view of an alternate embodiment of a guide assembly having a centrally located rotation axis.

An alternative embodiment of a guide assembly is configured so that the relative rotation point is located at the approximate center of the guide plate and guide plate aperture. FIG. 46 illustrates guide assembly 510a, which includes tibial baseplate trial 512a, guide plate trial 514a, and adjustment mechanism 516a. Guide plate trial 514a is rotatable relative to base plate trial 512a about centrally located axis 520a, which is shown as a point in FIG. 46. A slot 564a is oriented to allow rotation about the central axis 520a, in comparison with the orientation of slot 560 and medial axis 520 of guide assembly 510. Rotation axis 520a is approximately centrally located, and may pass through the sagittal midline of guide plate trial 514a. Guide assembly 510a may be used in a trialing and implantation procedure for a mobile bearing knee prosthesis or trial having a centrally located rotation or pivot axis. Tibial inserts and/or tibial insert trials known in the art which rotate relative to a tibial component about a central axis may be used in conjunction with guide assembly 510a.

Another embodiment includes a trial system which allows adjustment of the relative rotation and/or relative anterior-posterior position between the tibial and femoral implant components prior to final implantation. Trial system 600, depicted in FIGS. 47-51, includes a guide plate and a baseplate, the guide plate selectively translatable relative to the baseplate along the anterior-posterior direction, and independently rotatable relative to the baseplate about a rotation axis. The addition of the anterior-posterior adjustment capability enables the surgeon to more accurately align the femur and tibia during a knee replacement procedure. This more accurate placement will lead to more natural motion of the knee joint in use, and less stress on the mating interface between the prosthetic components and the resected bone(s) to which the implanted components are mounted.

Trial system 600 includes a guide assembly 610 and a trial tibial insert assembly 601. Assembly 601 includes a tibial insert trial 602, and a cam post trial 604, which include the same features as described for tibial insert trials 402, 502, and cam post trials 502, 504. Guide assembly 610 includes baseplate trial 612 which may be directly, and temporarily, mounted to a resected tibial surface, and guide plate trial 614, which may be directly connected to the baseplate trial in an overlapping arrangement. A first adjustment mechanism 616, which may be called a translational adjustment mechanism, may connect the guide plate 614 and baseplate trial 612 to allow the guide plate trial to translate relative to the baseplate trial along at least one direction. More specifically, the first adjustment mechanism 616 is selectively actuable to control translation of the guide plate relative to the baseplate along a straight path. When the guide assembly is mounted on a resected tibial surface as in FIG. 47, the first adjustment mechanism 616 can be actuated to control translation of guide plate trial 614 relative to baseplate trial 612 along an anterior-posterior path. A second adjustment mechanism 618, which may be called a rotational adjustment mechanism, is actuable to control the juxtaposition of the baseplate trial 612 relative to the guide plate trial 614 about a rotation axis. Other embodiments may include any or none of the translational and rotational adjustment mechanisms 516, 616, 618, or other adjustment mechanisms known in the art to accomplish the same purpose.

Figure 48:
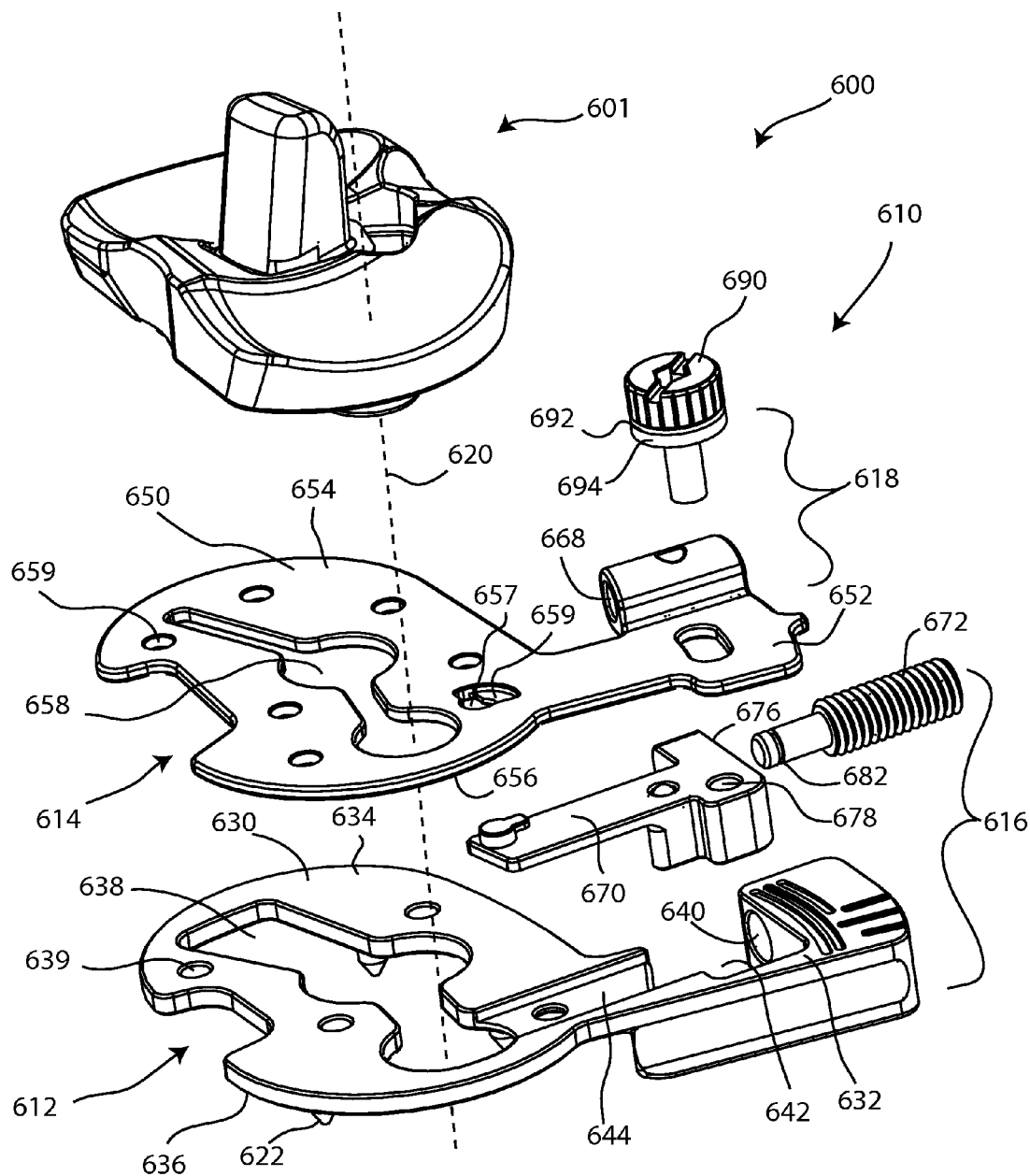
FIG. 48 is an exploded view of the trial system of FIG. 47, the trial system including the articulating trial insert, and the guide assembly which includes a guide plate, a baseplate, a first adjustment mechanism which controls translation between the guide plate and the baseplate, and a second adjustment mechanism which controls rotation between the guide plate and the baseplate.
Figure 49:
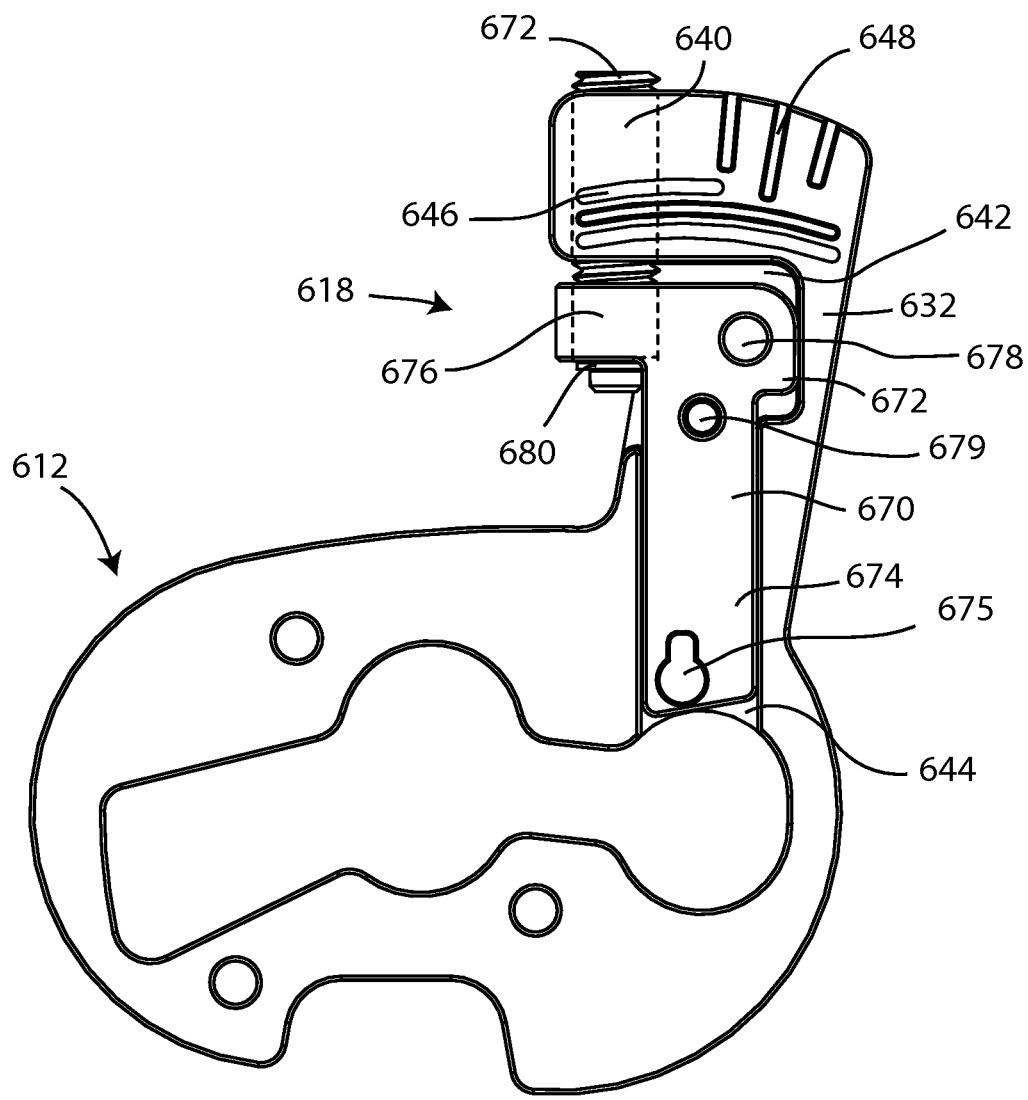
FIG. 49 is a superior view of the baseplate and first adjustment mechanism of FIG. 48.

Referring to FIGS. 48 and 49, baseplate trial 612 may be shaped similarly to tibial baseplate trial 512 and share similar features, as may guide plate trial 614 with guide plate trial 514. Baseplate trial 612 includes a flat ovoid baseplate body 630, from which a baseplate extension 632 extends generally anteriorly. The baseplate trial 612 includes a superior side 634, and an inferior side 636 from which pegs 622 may protrude. A baseplate aperture 638 perforates the baseplate body 630, extending between the superior side 634 and the inferior side 636, and may be irregularly shaped. A plurality of additional holes 639 may also extend through the baseplate trial 612. Baseplate extension 632 includes a passage 640 configured to receive an adjustment fastener, and a cavity 642 shaped to receive a slide. A groove 644 extends across a portion of the baseplate trial 612, from the baseplate body 630 onto the extension 632. The groove 644 may define a track which provides a straight path for translation of the guide plate trial 614 relative to the baseplate trial 612. Translation indicia 646 and rotation indicia 648 are provided to indicate the relative position of the guide plate to the baseplate. Indicia 646, 648 may include markings, writing, numbers, slots, grooves, bumps, ridges or other indicia known in the art, or combinations thereof.

Figure 50:
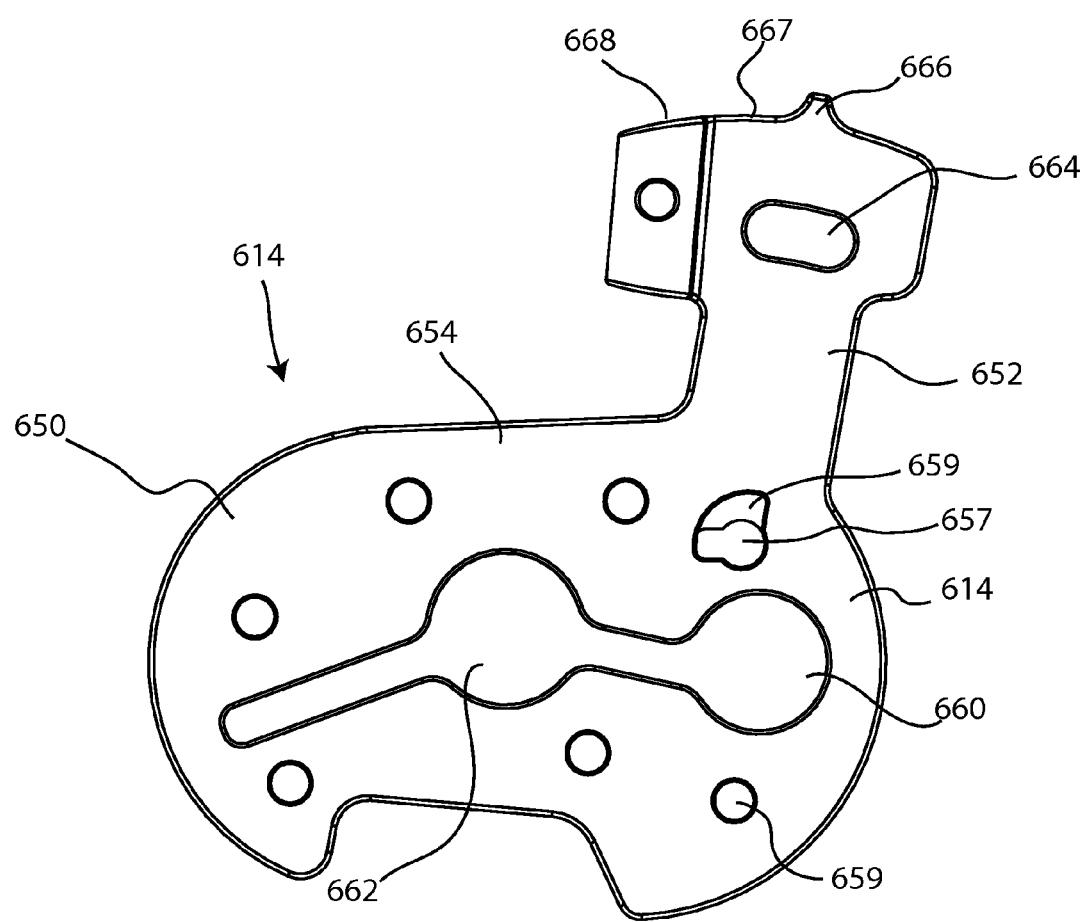
FIG. 50 is a superior view of the guide plate of FIG. 48.

Referring to FIGS. 48 and 50, the guide plate trial 614 may be shaped similarly to the baseplate trial 612, and has a guide plate body 650 from which a guide plate extension 652 extends. The guide plate trial 614 includes a superior side 654, and an inferior side 656. A guide plate aperture 658 perforates the guide plate body 650, extending between the superior side 654 and the inferior side 656. The guide plate aperture 658 may be similarly shaped to the baseplate aperture 638, but the baseplate aperture 638 is larger in most dimensions so that when the guide plate trial 614 is operatively assembled with the baseplate trial 612, clear passage may be obtained through both apertures regardless of the rotational or translational juxtaposition of the plates 612, 614. Guide plate aperture 658 may include a first port 660 and a second port 662, which may be shaped to receive first and second bosses formed on a tibial insert trial. A rotation axis 620 passes through base plate trial 612, and first port 660 of guide plate trial 614, in a medial location which may be the same as that described previously for rotation axis 520.

A keyway or latching feature 657 may be shaped as an opening with a retainer 659 to cooperate with a key or latch. A plurality of additional holes 659 may also extend through the guide plate trial 614. A slot 664 allows passage of a fastener for connection to a baseplate and/or slide. A tab 666 may form part of an indicator which shows the relative rotation of the guide plate to the baseplate, and an edge 667 of the extension may indicate the relative A/P position of the plates. A slot, or bore 668, may be located on the extension 652 to receive a tool to enable rotation of the guide plate.

Referring to FIGS. 48 and 49, a slide 670 and fastener 672 may be connected to baseplate trial 612 and guide plate trial 614 to connect the plates together and provide controlled translational adjustment of the guide plate relative to the baseplate. Slide 670 includes a body 672 and a tongue 674, the body 672 shaped to fit with clearance into cavity 462 and the tongue shaped to fit closely into groove 644. A latch or tab 675 protrudes from the tongue 674, and is shaped to be received in latching feature 657. A first passage 676 which may be parallel to and/or offset from the tongue 674 extends through the slide, as does a second passage 678 which may be perpendicular to the tongue and the first passage. When slide 670 is properly fitted into cavity 642 and groove 644, extension passage 640 axially aligns with slide first passage 676. Fastener 672, which may be threaded, is shaped to extend through passages 640, 676, which may also be threaded. A split washer 680 may be slid onto fastener 672 and fit into a retaining groove 682 on the fastener, thus retaining fastener 672 axially in passages 640, 676. A ball plunger 679 as described above may be mounted into an opening on the baseplate trial as a tactile indicator. Baseplate trial 612 may be provided pre-assembled with slide 670, fastener 672 and washer 680.

Figure 47:
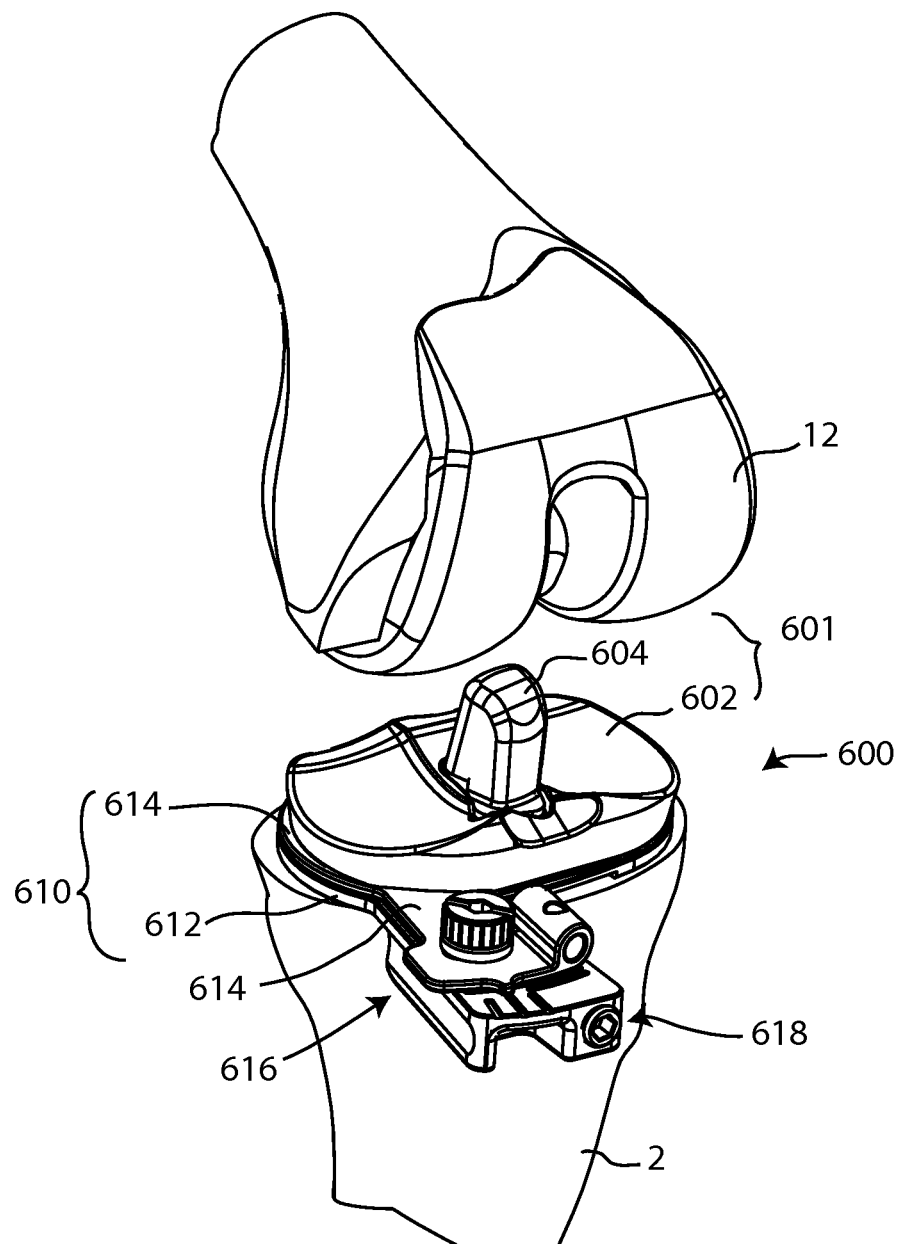
FIG. 47 is a perspective view of a knee joint knee joint in a flexed position, with a trial system positioned between a femoral component and a rotationally adjustable guide assembly.
Figure 51:
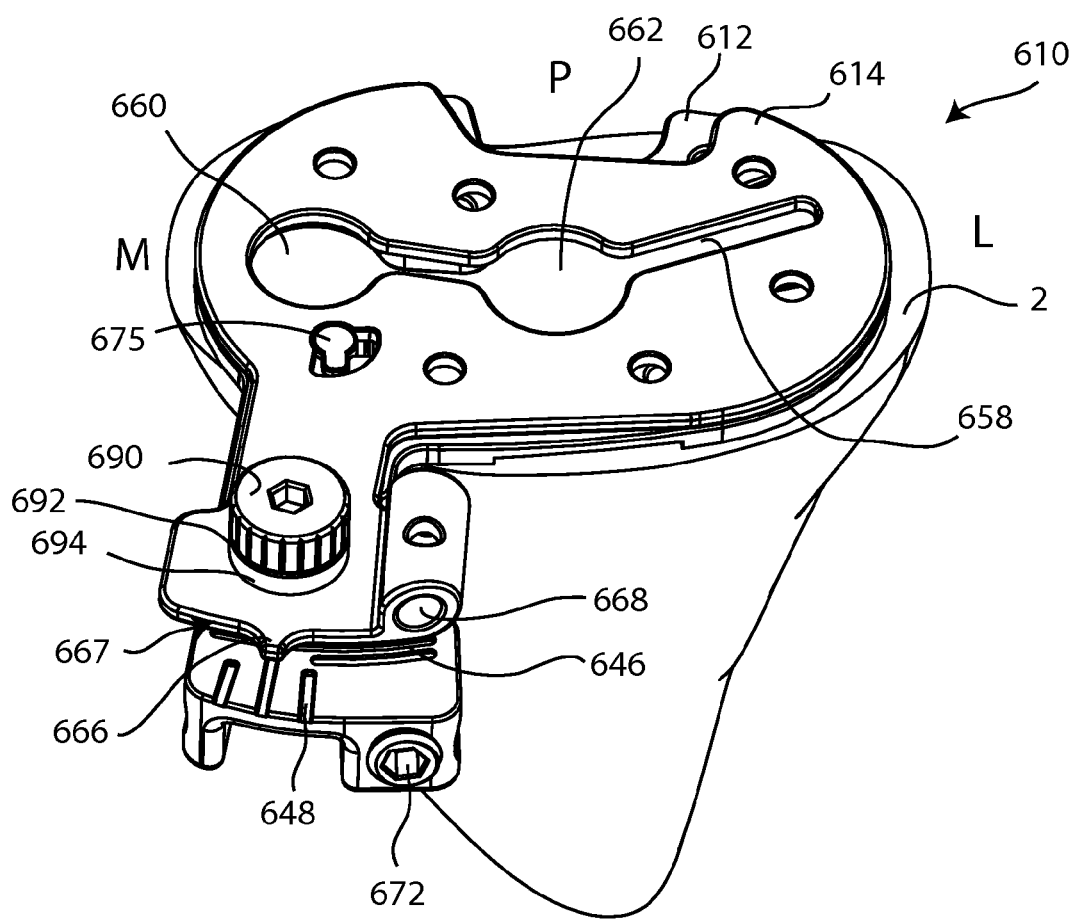
FIG. 51 is an antero-superior view of the guide assembly of FIG. 48 mounted on a resected tibia, with the guide plate in a rotationally and translationally centered position relative to the baseplate.

In one method of use, guide assembly 610 is assembled as seen in FIGS. 49 and 51. Slide 670 is assembled with baseplate trial 612 as described above. Guide plate trial 614 is placed on baseplate trial 612, positioned so that tab 675 fits through latching feature 657, and then rotated so that tab 675 overlaps the retainer 659 of latching feature 657, thus latching the guide plate trial 614 to the baseplate trial 612, but allowing relative rotation between the two without separation. A locking screw 690, with wave washer 692 and flat washer 694 as described previously, is inserted through slot 664 and into passage 678. Guide plate trial 614 is positioned with tab 666 and edge 667 in central positions as indicated by the indicia 646, 648. The locking screw 690 is tightened down. The guide assembly 610 is installed in a centered position on the resected tibial surface. A femoral component 12 and trial tibial insert assembly 601 are installed as seen in FIG. 47, with a boss of trial insert 602 received in first port 660, and a boss of cam post trial 604 received in second port 662, allowing rotation of insert 602 relative to the guide assembly 610 about rotation axis 620. The femoral component 12 is positioned with cam post trial 604 engaged in opening 74. Locking screw 690 is loosened, and the knee flexed and then extended. The surgeon can confirm proper tibiofemoral alignment during this flexion and extension. When the proper alignment is determined, fastener 672 may be actuated to move slide 670 and urge attached guide plate trial 614 anteriorly and/or posteriorly along a straight path to match the alignment. Trial insert assembly 601 may be carried along with guide plate trial 614 during translation and rotation of the guide plate. The anterior/posterior translation may be constrained by the movement of slide body 672 within cavity 642 of baseplate trial 612, and the movement of tongue 674 in groove 644. Guide plate trial 614 may also be rotated about rotation axis 620 by manually moving extension 652, or by inserting a tool into bore 668 to rotationally lever the guide plate. The rotational movement may be constrained by slot 664 around screw 690. It is appreciated that a single tool, for example a hex driver, may be used to actuate locking screw 690, lever extension 652, and/or actuate fastener 672. As guide plate trial 614 is adjusted, indicia 646 cooperate with edge 667 to indicate the relative A/P position of the guide plate, and indicia 648 cooperate with tab 666 to indicate the relative rotational position of the guide plate. Ball plunger 679 may provide tactile indication when the guide plate trial 614 is rotated or translated out of either central position. After the guide plate trial 614 has been translated and/or rotated to a selected alignment, the locking screw 690 is again tightened down to lock the juxtaposition of the guide plate trial 614 relative to the baseplate trial 612. The trial tibial insert assembly 601 is removed. Using the aperture 658 as a guide, standard drills and punches can then be used to cut the tibial bone for the final prosthetic tibial baseplate keel and fins. A properly sized and configured tibial insert 16 and cam post 19 can be chosen, based on the trial tibial insert assembly 601 and information gleaned during the trialing process. The guide assembly 610 can then be removed, and implantation of the prosthetic knee can proceed per standard techniques.

Any of the trial baseplates and guide plates disclosed herein may be made of materials with high strength and suitability for short-term patient contact. Suitable materials include biocompatible metals or metal alloys including stainless steel, cobalt chrome, titanium alloy; plastics including polyetherimide, polypropylene, acetal, polycarbonate, polyetheretherketone (PEEK); or combinations thereof. Reinforcing material such as glass fiber or carbon fiber can be added to a plastic embodiment to add strength and dimensional stability. In other embodiments, a trial baseplate and guide plate may be formed as a single piece, incorporating a flexible material to provide the intended rotational and/or translational articulation.

Any of the tibial insert and cam post trials disclosed herein may be made of synthetic materials with good biocompatibility and ability to be sterilized. Suitable synthetic materials include PEEK polyetherimide, polypropylene, acetal, polycarbonate or ABS. Alternatively, the trial components could be made of metal or ceramic, and/or be either uncoated or coated to reduce friction and/or wear. Any single component may be made of a combination of metal(s), synthetic(s), and/or ceramic(s). Although the insert and cam post trials can be made in any color, it is preferred that they be different in color from the final implants.

Any of the components disclosed herein may include surface treatments or additives in one or more of the component materials to provide beneficial effects such as anti-microbial, analgesic or anti-inflammatory properties.

In the embodiments depicted in FIGS. 39-51, the trial guide assemblies include extensions and adjustment mechanisms which are anteriorly oriented, in order to provide convenient access for practitioners during an anterior access procedure. Of course, in other embodiments the extensions and/or adjustment mechanisms may be located posteriorly, medially and/or laterally or any orientation therebetween to provide alternative access. In addition, in other embodiments the extensions and/or adjustment mechanisms may not be coplanar with the trial and guide plates but may be at selected angle(s) relative to the guide assembly. A first adjustment mechanism may be located at one orientation while a second adjustment mechanism may be co-located with the first adjustment mechanism, or may be offset. For example a first adjustment mechanism may be positioned at an anterior-medial orientation, while a second adjustment mechanism is positioned at an anterior-lateral orientation.

In the embodiments depicted in FIGS. 39-51, the trial systems are configured to provide cutting guidance and articulating trial components for a knee joint replacement. Other embodiments within the scope of the invention may be configured to provide cutting guidance and/or trial components for other joints, including but not limited to: hip, ankle, wrist, elbow, finger, thumb, toe, and intervertebral joints. In the case of an intervertebral joint, using a trial which has rotational articulation will allow confirmation of correct rotational alignment between the vertebrae prior to final implantation. Trial systems 500 and 600 are configured so that the guide plate trial and/or tibial insert trial are rotatable about a medially located rotation axis. It is appreciated that in other embodiments, including other joint embodiments, the rotation axis may be medially, centrally, or laterally located, and may also be centered anterior-posteriorly, or offset in any anterior-posterior orientation.

The tibial insert trial, trial baseplates, and trial guide plates disclosed herein may be formed in varying footprint shapes including ovoid, rectangular, circular, square, polygonal, and may be bilaterally symmetrical from a medial-lateral, superior-inferior, and/or anterior-posterior perspective, or bilaterally asymmetrical from one or more of those perspectives.

In an alternative embodiment, trial system 500 or 600 or other joint embodiments may further include a medial/lateral adjustment mechanism. This mechanism may be configured similarly to the anterior/posterior adjustment mechanism 618, but positioned to provide controlled medial/lateral adjustment of the trial guide plate relative to the trial baseplate. Another embodiment may include anterior/posterior adjustment and medial/lateral adjustment, but not rotational adjustment.

The present invention may be embodied in other specific forms without departing from its spirit or essential characteristics. It is appreciated that various features of the above described examples and embodiments may be mixed and matched to form a variety of other combinations and alternatives; for example, using the cam post 19 with the tibial insert 116, using trial systems 400 or 400a with any of the tibial baseplates, femoral implants, or guide assemblies disclosed herein, or providing the translational adjustment mechanism of trial system 600 to trial system 500. It is also appreciated that this system should not be limited simply to total knee prosthesis. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A knee joint trial system, the system comprising:
    a baseplate trial comprising a flat baseplate body having a baseplate trial superior surface, a baseplate trial inferior surface and a baseplate trial aperture extending between the baseplate trial superior surface and the baseplate trial inferior surface, the baseplate trial aperture comprising a baseplate trial port aligned along a medially-displaced axis, and an elongated baseplate trial opening extending laterally from the baseplate trial port, the baseplate trial inferior surface shaped to be positioned on a resected tibial surface;
    a guide plate trial comprising a flat guide plate body having a guide plate trial superior surface, a guide plate trial inferior surface and a guide plate trial aperture extending between the guide plate trial superior surface and the guide plate trial inferior surface, the guide plate trial aperture comprises a guide plate trial port aligned along the medially-displaced axis, and an elongated guide plate trial opening extending laterally from the guide plate trial port, the guide plate trial lying directly on the baseplate trial with the guide plate trial inferior surface overlaying the baseplate trial superior surface;
        a femoral implant comprising a cam feature, a pair of condyles and a femur facing surface;
    a tibial insert trial comprising guide plate trial facing side, a femoral implant facing side, a lateral articulating surface, and a medial articulating surface, and wherein the guide plate trial facing side defines a boss positioned medially on the guide plate trial facing side that is rotatable within the guide plate trial port to enable a pivotal articulation of the guide plate trial facing side with the guide plate trial superior surface about the medially-displaced axis, wherein each of the medial and lateral articulating surfaces are shaped and positioned to articulate with the pair of condyles;
    the tibial insert trial further comprising an arc-shaped channel passing through the guide plate trial facing side of the tibial insert trial, the arc-shaped channel tibial being concave toward the medial articulating surface; and
    a post assembled with the tibial insert trial and passing through the arc-shaped channel into the guide plate trial aperture, wherein the pivotal articulation is provided at least partially by contact of an anterior side of the cam feature with a posterior side of the post during articulation of the pair of condyles with the medial and lateral articulating surfaces;
    wherein the baseplate trial is rotatable relative to the guide plate trial about the medially-displaced axis to confirm proper contact between the femoral implant and the tibial insert trial.

2. The system of claim 1, wherein the baseplate trial aperture is larger than the guide plate trial aperture in at least one dimension.

3. The system of claim 2, wherein the guide plate trial superior and inferior surfaces are planar.

4. The system of claim 3, wherein the baseplate trial superior and inferior surfaces are planar.

5. The system of claim 1, wherein the baseplate trial, guide plate trial and tibial insert trial each have an ovoid footprint shape.

6. The system of claim 1, wherein the baseplate trial includes an outer periphery and the guide plate trial includes an outer periphery, wherein a posterior portion of the baseplate trial outer periphery includes a notch recessed toward a center of the baseplate trial, and wherein a posterior portion of the guide plate trial outer periphery includes a notch recessed toward a center of the guide plate trial, and wherein the guide plate trial notch is wider medial-laterally than the baseplate trial notch.

7. The system of claim 6, wherein the baseplate trial has a plurality of circular holes extending between the baseplate trial superior surface and the baseplate trial inferior surface, the holes positioned between the baseplate trial aperture and the baseplate trial outer periphery.

8. The system of claim 6, wherein the guide plate trial has a plurality of circular holes extending between the guide plate trial superior surface and the guide plate trial inferior surface, the holes positioned between the guide plate trial aperture and the guide plate trial outer periphery.

9. The system of claim 1, wherein at least one of the tibial insert trial, and guide plate trial is available in a variety of dimensions to allow selection of a tibial insert.

* * * * *

UNITED STATES PATENT AND TRADEMARK OFFICE
CERTIFICATE OF CORRECTION

PATENT NO. : 9,095,453 B2  
APPLICATION NO. : 12/949103  
DATED : August 4, 2015  
INVENTOR(S) : Michael D. Ries et al.

Page 1 of 1

It is certified that error appears in the above-identified patent and that said Letters Patent is hereby corrected as shown below:

In the claims

In column 23, line 58, claim 1, after "comprising" please insert --a--.

Signed and Sealed this
Twenty-fourth Day of November, 2015

Michelle K. Lee
*Director of the United States Patent and Trademark Office*